(12) United States Patent
Cheng et al.

(10) Patent No.: US 7,951,366 B2
(45) Date of Patent: May 31, 2011

(54) PHARMACEUTICAL PREPARATION AND METHOD OF TREATMENT OF HUMAN MALIGNANCIES WITH ARGININE DEPRIVATION

(75) Inventors: Ning Man Cheng, Hong Kong (CN); Yun Chung Leung, Hong Kong (CN); Wai Hung Lo, Hong Kong (CN)

(73) Assignee: Bio-Cancer Treatment International Limited, Central (HK)

( * ) Notice: Subject to any disclaimer, the term of this patent is extended or adjusted under 35 U.S.C. 154(b) by 0 days.

(21) Appl. No.: 10/518,223

(22) PCT Filed: Jun. 20, 2003

(86) PCT No.: PCT/GB03/02665
§ 371 (c)(1),
(2), (4) Date: Dec. 15, 2004

(87) PCT Pub. No.: WO04/000349
PCT Pub. Date: Dec. 31, 2003

(65) Prior Publication Data
US 2005/0244398 A1 Nov. 3, 2005

Related U.S. Application Data

(60) Provisional application No. 60/390,757, filed on Jun. 20, 2002.

(30) Foreign Application Priority Data

Sep. 9, 2002 (WO) .................. PCT/CN02/00635

(51) Int. Cl.
*A61K 38/46* (2006.01)
*C12N 9/96* (2006.01)
*C12N 9/14* (2006.01)
*C12N 9/78* (2006.01)
*C12P 21/06* (2006.01)
*C07H 21/04* (2006.01)

(52) U.S. Cl. ........ 424/94.6; 435/188; 435/195; 435/227; 435/69.1; 536/23.2

(58) Field of Classification Search .................. 424/94.6; 435/195, 252.31, 471, 69.1; 536/23.2
See application file for complete search history.

(56) References Cited

U.S. PATENT DOCUMENTS

| | | | |
|---|---|---|---|
| 6,054,308 A * | 4/2000 | Vockley et al. | ................ 435/227 |
| 6,261,557 B1 | 7/2001 | Tepic et al. | |
| 6,316,199 B1 | 11/2001 | Vockley et al. | |

FOREIGN PATENT DOCUMENTS

| | | |
|---|---|---|
| EP | 0 956 864 A1 | 11/1999 |
| WO | WO 98/06421 | 2/1998 |
| WO | WO 99/43345 A1 | 9/1999 |
| WO | WO 02/09766 A1 | 2/2002 |
| WO | WO 02/24156 A3 | 3/2002 |
| WO | WO 02/44360 A2 | 6/2002 |
| WO | WO 03/063780 A3 | 8/2003 |

OTHER PUBLICATIONS

Haraguchi et al. GenBank Accession No. M14502, "Human liver, arginase mRNA, complete cds", created Oct. 1994.*
Sequence alignment of SEQ ID No. 9.*
Mehvar et al. (Modulation of the pharmacokinetics and pharmacodynamics of proteins by polyethylene glycol conjugation, J Pharm Pharmaceut Sci, 3(1):125-136, 2000).*
Baillie, et al. 1998. A heat-inducible *Bacillus subtilis* bacteriophage Φ105 expression system for the production of the protective antigen of *Bacillus anthracis*. *FEMS Microbiology Letters*, 163:43-47.
Colleluori, et al. 2001. Expression, purification, and characterization of human type II arginase. *Archives of Biochemistry and Biophysics*, 389(1):135-143.
Haraguchi, et al. Created Jun. 7, 1987; last updated, Version 5, Mar. 4, 2000. Molecular cloning and nucleotide sequence of cDNA for human liver arginase. Database accession No. M14502, abstract. XP-002258160.
Haraguchi, et al. 1987. Molecular cloning and nucleotide sequence of cDNA for human liver arginase. *Proc. Natl. Acad. Sci. USA.* 84:412-415.
Harris, et al. Pegylation: A novel process for modifying pharmacokinetics. *Clin. Pharmacokinet*, 40:539-551.
Ikemoto, et al. 1989. Purification and properties of human erythrocyte arginase. *Ann. Clin. Biochem.*, 26:547-553.
Ikemoto, et al. 1990. Expression of human liver arginase in *Escherichia coli. Biochem. J.*, 270:697-703.
Lamb, et al. 2000. Single amino acid (arginine) deprivation induces G1 arrest associated with inhibition of Cdk4 expression in cultured human diploid fibroblasts. *Experimental Cell Research*, 255:238-249.
Lea, et al. 1993. Inhibitory effect of arginine restriction on hepatoma growth. *Cancer Biochem. Biophys.*, 13(3):171-179.
Leung, et al. 1995. Characterization of an insertion in the phage Φ105 genome that blocks host *Bacillus subtilis* lysis and provides strong expression of heterologous genes. *Gene*, 154:1-6.
Malumbres, et al. 2001. To cycle or not to cycle: A critical decision in cancer. *Nature Reviews*, 1:222-231.
Ozer, N. 1985. A new enzyme-coupled spectrophotometric method for the determination of arginase activity. *Biochemical Medicine*, 33:367-371.
Savoca, et al. 1979. Preparation of a non-immunogenic arginase by the covalent attachment of polyethylene glycol. *Biochimica et Biophysica Acta.*, 578:47-53.
Savoca, et al. 1984. Cancer therapy with chemically modified enzymes. II. The therapeutic effectiveness of arginase, and arginase modified by the covalent attachment of polyethylene glycol, on the taper liver tumor and the L5178Y murine leukemia. *Cancer Biochem Biophys.*, 7:261-268.

(Continued)

*Primary Examiner* — Anand U Desai
*Assistant Examiner* — Iqbal H Chowdhury
(74) *Attorney, Agent, or Firm* — Foley & Lardner LLP

(57) ABSTRACT

The present invention provides an isolated and substantially purified recombinant human arginase having sufficiently high enzymatic activity and stability to maintain Adequate Arginine Depletion in a patient. The present invention also provides a pharmaceutical composition comprising the modified invention enzyme and method for treatment of diseases using the pharmaceutical composition.

10 Claims, 46 Drawing Sheets

OTHER PUBLICATIONS

Scott, et al. 2000. Single amino acid (arginine) deprivation: Rapid and selective death of cultured transformed and malignant cells. *British Journal of Cancer*, 83(6):800-810.

Storr, et al. 1974. The effects of arginine deficiency on lymphoma cells. *British Journal of Cancer*, 30:50-59.

Thornewell, et al. 1993. An efficient expression and secretion system based on *Bacillus subtilis* phage Φ105 and its use for the production of *B. cereus* β-lactamase I. *Gene*, 133:47-53.

Wheatley, et al. 2000. Single amino acid (arginine) restriction: Growth and death of cultured HeLa and human diploid fibroblasts. *Cellular Physiology and Biochemistry*, 10:37-55.

Examination Report from New Zealand Patent Application No. 537774 dated Mar. 11, 2005.

International Preliminary Examination Report from PCT/GB03/02665 dated Jul. 20, 2004.

Written Opinion from PCT/GB03/02665 dated Mar. 22, 2004.

Ikemoto et al., Live-type Arginase is a Highly Sensitive Marker for Heptocelluar Damage in Rats, Clinical CHemistry, 2001, p. 496-498, vol. 47.

Takaku et al., In vivo anti-tumor activitiy of arginine deiminase purified from mycoplasma arginini, 1992, Int. J. Cancer, 51:244-249.

Jiang et al., Synthesis and application of Polyethylene Glycol derivatives for the chemical modification of Biomacromolecules, 2002 FEB, p. 34-40.

* cited by examiner

Fig. 2A

```
   1 gaattgtacg tcaaagagat gaagcagaaa aacgtcgtcg agaagaagct gaacgacaaa
  61 aagtgaaatg cgagggaagt ccaagaaatg gtgattatga gggtgtctat ttcaccaaaa
 121 acggagaata tttattggaa ttaagagtct ctgggactgc tcttgtaaat gctccttgta
 181 atttaaagga tattgacata acgaaatggt tgtgtaaaac agggagatta tatcttgata
 241 aggttaagaa atttgaaata gttactattc tttcccatga cgtagaaaat caaaagatta
 301 taacagaatg ggagtcactc cccagagagg ctttacccga acaatttgat tcataagaac
 361 taattagtag cgctttccaa tggaggcgct tttttatttg ggtagttgca taccactaaa
 421 gatgttcagg tgcacatgag cattggagga aaggaacgct ttaggggaa gggaaaccctt
 481 taaacagtct taatccccct tgattttatg ttctctgtaa actgcgtccg gtaaatctca
 541 ggatagacaa tcggcggtta acggcttgag tgcggggggca gtttagaaag aatatgattg
 601 gagggattca tagatgcatc accatcacca tcatatgagc gccaagtcca gaaccatagg
 661 gattattgga gctcctttct caaagggaca gccacgagga ggggtggaag aaggccctac
 721 agtattgaga aaggctggtc tgcttgagaa acttaaagaa caagagtgtg atgtgaagga
 781 ttatggggac ctgcccttttg ctgacatccc taatgacagt cccttcaaa ttgtgaagaa
 841 tccaaggtct gtgggaaaag caagcgagca gctggctggc aaggtggcac aagtcaagaa
 901 gaacggaaga atcagcctgg tgctgggcgg agaccacagt ttggcaattg gaagcatctc
 961 tggccatgcc agggtccacc ctgatcttgg agtcatctgg gtggatgctc acactgatat
1021 caacactcca ctgacaacca caagtggaaa cttgcatgga caacctgtat ctttcctcct
1081 gaaggaacta aaaggaaaga ttcccgatgt gccaggattc tcctgggtga ctccctgtat
1141 atctgccaag gatattgtgt atattggctt gagagacgtg gaccctgggg aacactacat
1201 tttgaaaact ctaggcatta aatactttc aatgactgaa gtggacagac taggaattgg
1261 caaggtgatg gaagaaacac tcagctatct actaggaaga aagaaaaggc caattcatct
1321 aagttttgat gttgacggac tggacccatc tttcacacca gctactggca caccagtcgt
1381 gggaggtctg acatacagag aaggtctcta catcacagaa gaaatctaca aaacagggct
1441 actctcagga ttagatataa tggaagtgaa cccatcccctg gggaagacac cagaagaagt
1501 aactcgaaca gtgaacacag cagttgcaat aaccttggct tgtttcggac ttgctcggga
1561 gggtaatcac aagcctattg actaccttaa cccacctaag taaatgtgga aacatccgat
1621 ataaatctca tagttaatgg cataattaga aagctaatca ttttcttaag catagagtta
1681 tccttctaaa gacttgttct ttcagaaaaa tgttttttcca attagtataa actctacaaa
1741 ttccctcttg gtgtaaaatt caagatgtgg aaattctaac tttttgaaa tttaaaagct
1801 tatatttttct aacttggcaa aagacttatc cttagaaaga gaagtgtaca ttgatttcca
1861 attaaaaatt tgctggcatt aaaaataagc acacttacat aagcccccat acatagagtg
1921 ggactcttgg aatcaggaga caaagctacc acatgtggaa aggtactatg tgtccatgtc
1981 attcaaaaaa tgtgattcta ga
```

Fig. 2B

```
  1 atgcatcaccatcaccatcat
    M  H  H  H  H  H
 22 atgagcgccaagtccagaaccataggaattattggagctcctttc
    M  S  A  K  S  R  T  I  G  I  I  G  A  P  F
 67 tcaaagggacagccacgaggagggtggaagaaggccctacagta
    S  K  G  Q  P  R  G  G  V  E  E  G  P  T  V
112 ttgagaaaggctggtctgcttgagaaacttaaagaacaagagtgt
    L  R  K  A  G  L  L  E  K  L  K  E  Q  E  C
157 gatgtgaaggattatggggacctgccctttgctgacatccctaat
    D  V  K  D  Y  G  D  L  P  F  A  D  I  P  N
202 gacagtccctttcaaattgtgaagaatccaaggtctgtgggaaaa
    D  S  P  F  Q  I  V  K  N  P  R  S  V  G  K
247 gcaagcgagcagctggctggcaaggtggcacaagtcaagaagaac
    A  S  E  Q  L  A  G  K  V  A  Q  V  K  K  N
292 ggaagaatcagcctggtgctgggcggagaccacagtttggcaatt
    G  R  I  S  L  V  L  G  G  D  H  S  L  A  I
337 ggaagcatctctggccatgccagggtccaccctgatcttggagtc
    G  S  I  S  G  H  A  R  V  H  P  D  L  G  V
382 atctgggtggatgctcacactgatatcaacactccactgacaacc
    I  W  V  D  A  H  T  D  I  N  T  P  L  T  T
427 acaagtggaaacttgcatggacaacctgtatctttcctcctgaag
    T  S  G  N  L  H  G  Q  P  V  S  F  L  L  K
472 gaactaaaaggaaagattcccgatgtgccaggattctcctgggtg
    E  L  K  G  K  I  P  D  V  P  G  F  S  W  V
517 actccctgtatatctgccaaggatattgtgtatattggcttgaga
    T  P  C  I  S  A  K  D  I  V  Y  I  G  L  R
562 gacgtggaccctggggaacactacattttgaaaactctaggcatt
    D  V  D  P  G  E  H  Y  I  L  K  T  L  G  I
607 aaatacttttcaatgactgaagtggacagactaggaattggcaag
    K  Y  F  S  M  T  E  V  D  R  L  G  I  G  K
652 gtgatggaagaaacactcagctatctactaggaagaaagaaaagg
    V  M  E  E  T  L  S  Y  L  L  G  R  K  K  R
697 ccaattcatctaagttttgatgttgacggactggacccatctttc
    P  I  H  L  S  F  D  V  D  G  L  D  P  S  F
742 acaccagctactggcacaccagtcgtgggaggtctgacatacaga
    T  P  A  T  G  T  P  V  V  G  G  L  T  Y  R
787 gaaggtctctacatcacagaagaaatctacaaaacagggctactc
    E  G  L  Y  I  T  E  E  I  Y  K  T  G  L  L
832 tcaggattagatataatggaagtgaacccatccctggggaagaca
    S  G  L  D  I  M  E  V  N  P  S  L  G  K  T
877 ccagaagaagtaactcgaacagtgaacacagcagttgcaataacc
    P  E  E  V  T  R  T  V  N  T  A  V  A  I  T
922 ttggcttgtttcggacttgctcgggagggtaatcacaagcctatt
    L  A  C  F  G  L  A  R  E  G  N  H  K  P  I
967 gactaccttaacccacctaagtaa 990
    D  Y  L  N  P  P  K  *
```

Fig. 2C

```
  1 atgagcgccaagtccagaaccatagggattattggagctcctttc
    M  S  A  K  S  R  T  I  G  I  I  G  A  P  F
 46 tcaaagggacagccacgaggaggggtggaagaaggccctacagta
    S  K  G  Q  P  R  G  G  V  E  E  G  P  T  V
 91 ttgagaaaggctggtctgcttgagaaacttaaagaacaagagtgt
    L  R  K  A  G  L  L  E  K  L  K  E  Q  E  C
136 gatgtgaaggattatggggacctgccctttgctgacatccctaat
    D  V  K  D  Y  G  D  L  P  F  A  D  I  P  N
181 gacagtccctttcaaattgtgaagaatccaaggtctgtgggaaaa
    D  S  P  F  Q  I  V  K  N  P  R  S  V  G  K
226 gcaagcgagcagctggctggcaaggtggcacaagtcaagaagaac
    A  S  E  Q  L  A  G  K  V  A  Q  V  K  K  N
271 ggaagaatcagcctggtgctgggcggagaccacagtttggcaatt
    G  R  I  S  L  V  L  G  G  D  H  S  L  A  I
316 ggaagcatctctggccatgccagggtccaccctgatcttggagtc
    G  S  I  S  G  H  A  R  V  H  P  D  L  G  V
361 atctgggtggatgctcacactgatatcaacactccactgacaacc
    I  W  V  D  A  H  T  D  I  N  T  P  L  T  T
406 acaagtggaaacttgcatggacaacctgtatctttcctcctgaag
    T  S  G  N  L  H  G  Q  P  V  S  F  L  L  K
451 gaactaaaaggaaagattcccgatgtgccaggattctcctgggtg
    E  L  K  G  K  I  P  D  V  P  G  F  S  W  V
496 actccctgtatatctgccaaggatattgtgtatattggcttgaga
    T  P  C  I  S  A  K  D  I  V  Y  I  G  L  R
541 gacgtggaccctggggaacactacattttgaaaactctaggcatt
    D  V  D  P  G  E  H  Y  I  L  K  T  L  G  I
586 aaatacttttcaatgactgaagtggacagactaggaattggcaag
    K  Y  F  S  M  T  E  V  D  R  L  G  I  G  K
631 gtgatggaagaaacactcagctatctactaggaagaaagaaaagg
    V  M  E  E  T  L  S  Y  L  L  G  R  K  K  R
676 ccaattcatctaagttttgatgttgacggactggacccatctttc
    P  I  H  L  S  F  D  V  D  G  L  D  P  S  F
721 acaccagctactggcacaccagtcgtgggaggtctgacatacaga
    T  P  A  T  G  T  P  V  V  G  G  L  T  Y  R
766 gaaggtctctacatcacagaagaaatctacaaaacagggctactc
    E  G  L  Y  I  T  E  E  I  Y  K  T  G  L  L
811 tcaggattagatataatggaagtgaacccatccctggggaagaca
    S  G  L  D  I  M  E  V  N  P  S  L  G  K  T
856 ccagaagaagtaactcgaacagtgaacacagcagttgcaataacc
    P  E  E  V  T  R  T  V  N  T  A  V  A  I  T
901 ttggcttgtttcggacttgctcgggagggtaatcacaagcctatt
    L  A  C  F  G  L  A  R  E  G  N  H  K  P  I
946 gactaccttaacccacctaagtaa 969
    D  Y  L  N  P  P  K  *
```

Fig. 6A

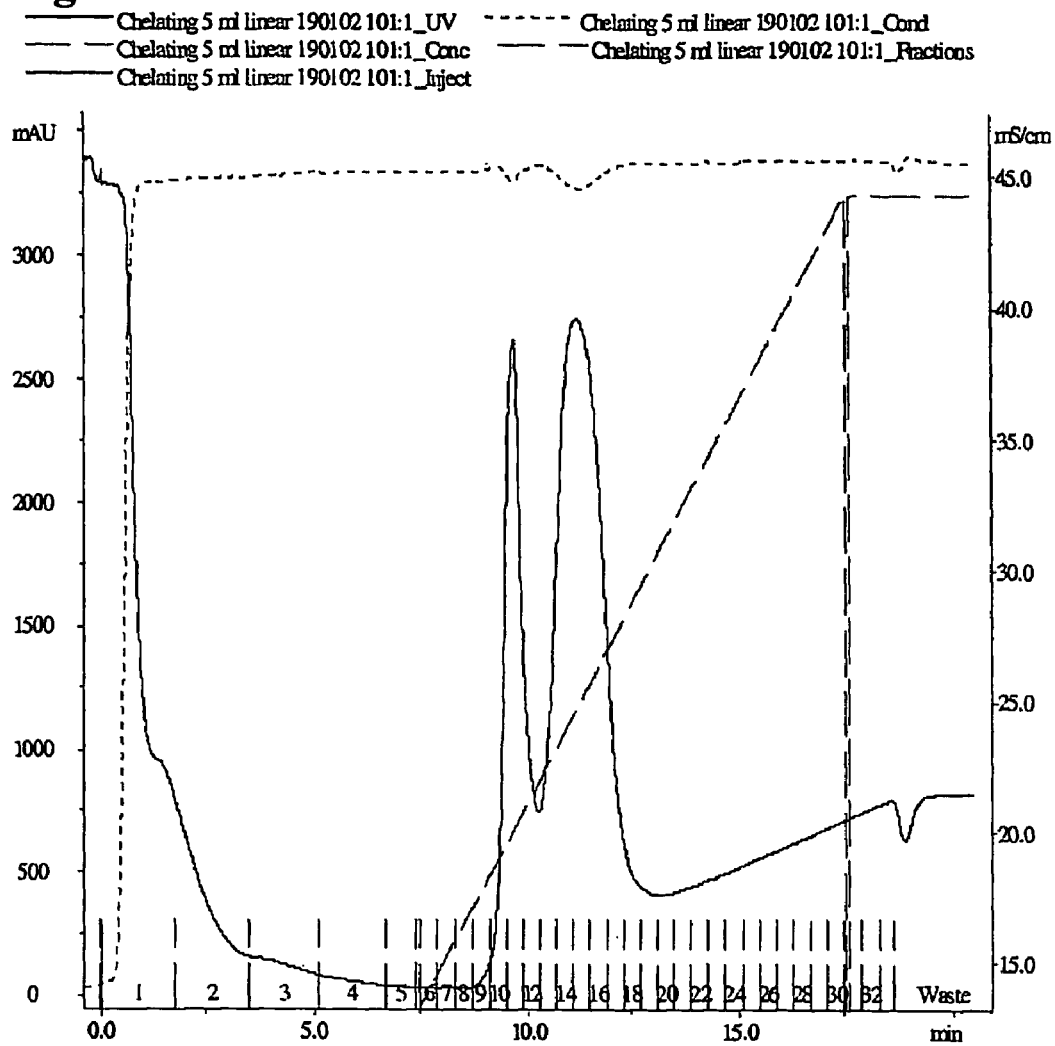

| Column | HiTrap_Chelating_1x5_ml |
|---|---|
| Pressure_limit | 0.8 (MPa) |
| Flow | 5.00 (ml/min) |
| UV_Averaging_time | 2.60 |
| Start_ConcB | 0.00 (%B) |
| Equilibrate_with | 0.5 (CV) |
| Flowthrough_FracSize | 8 (ml) |
| Empty_loop_with | 0 (ml) |
| Wash_column_with | 7 (CV) |
| Start_Frac_at | 0 (%B) |
| Eluate_FracSize | 2 (ml) |
| End_Frac_at | 100 (%B) |
| Target_ConcB_1 | 100 (%B) |
| Length_of_gradient_1 | 10 (base) |
| Target_ConcB_2 | 0 (%B) |
| Length_of_gradient_2 | 0 (base) |
| Target_ConcB_3 | 0 (%B) |
| Length_of_gradient_3 | 0.00 (base) |
| Conc_of_eluent_B | 100 (%B) |
| Clean_with | 4 (CV) |
| Reequilibrate_conc | 0.00 (%B) |
| Reequilibrate_with | 0.00 (CV) |

Fig. 7A

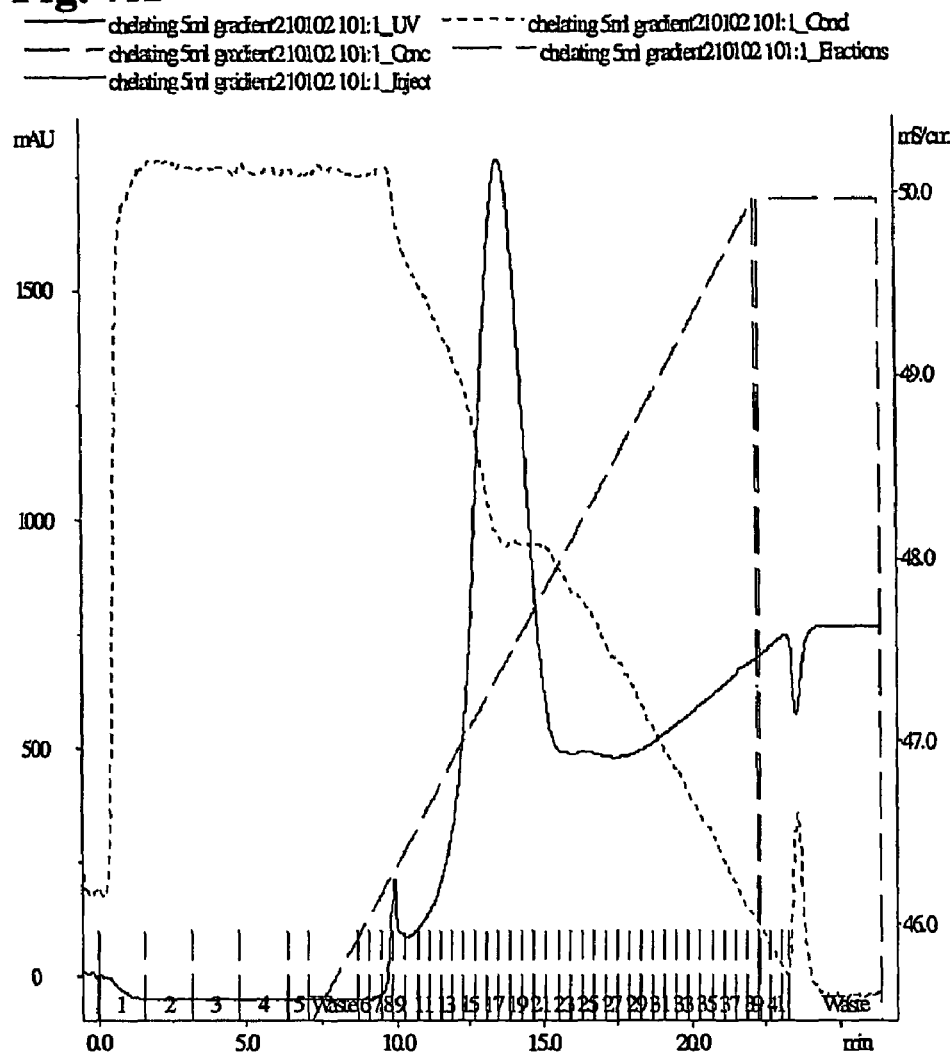

```
Column          HiTrap_Chelating_1x5_ml
Pressure_limit     0.8   (MPa)
Flow              5.00   (ml/min)
UV_Averaging_time 2.60
Start_ConcB       0.00   {%B}
Equilibrate_with  0.5    (CV)
Flowthrough_FracSize 8   (ml)
Empty_loop_with   0      (ml)
Wash_column_with  7      (CV)
Start_Frac_at     10     {%B}
Eluate_FracSize   2      (ml)
End_Frac_at       100    {%B}
Target_ConcB_1    100    {%B}
Length_of_gradient_1  15   (base)
Target_ConcB_2    0      {%B}
Length_of_gradient_2  0.00 (base)
Target_ConcB_3    0      {%B}
Length_of_gradient_3  0.00 (base)
Conc_of_eluent_B  100    {%B}
Clean_with        4.00   (CV)
Reequilibrate_conc 0.00  {%B}
Reequilibrate_with 0.00  (CV)
```

Fig. 8A

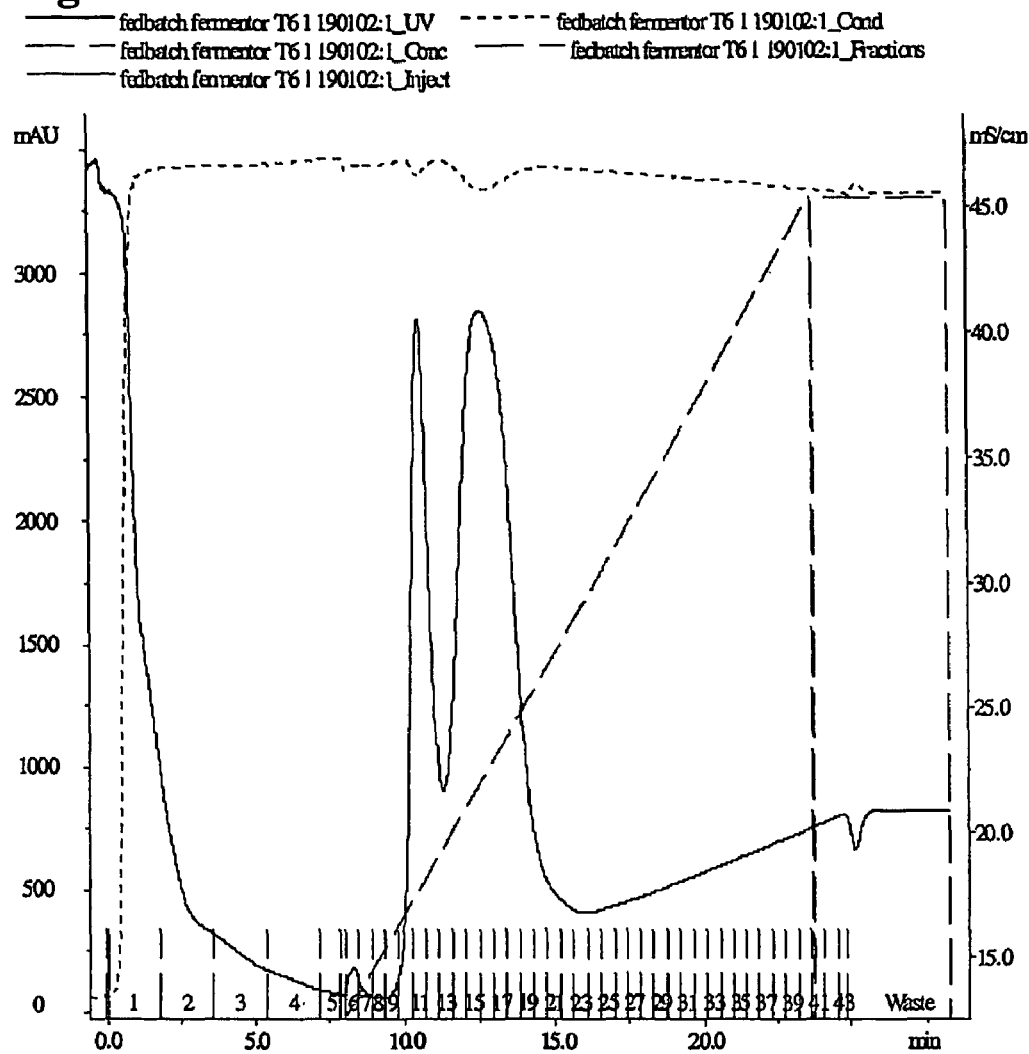

```
Column          HiTrap_Chelating_1x5_ml
Pressure_limit    0.8   {MPa}
Flow              5.00  {ml/min}
UV_Averaging_time   2.60
Start_ConcB       0.00  {%B}
Equilibrate_with  0.5   {CV}
Flowthrough_FracSize  8   {ml}
Empty_loop_with   0     {ml}
Wash_column_with  7     {CV}
Start_Frac_at     0     {%B}
Eluate_FracSize   2     {ml}
End_Frac_at       100   {%B}
Target_ConcB_1    100   {%B}
Length_of_gradient_1   14   {base}
Target_ConcB_2    0     {%B}
Length_of_gradient_2   0.00  {base}
Target_ConcB_3    0     {%B}
Length_of_gradient_3   0.00  {base}
Conc_of_eluent_B  100   {%B}
Clean_with        4.00  {CV}
Reequilibrate_conc  0.00  {%B}
Reequilibrate_with  0.00  {CV}
```

Fig. 9A

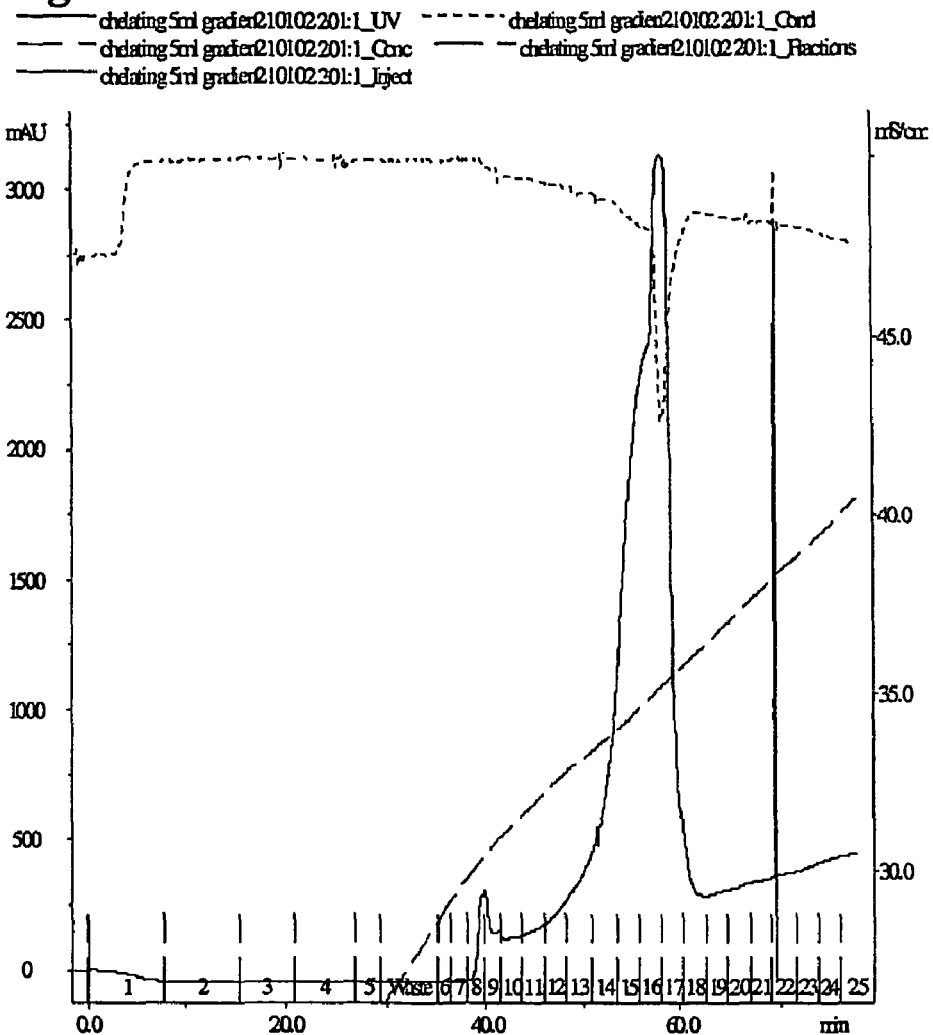

| | | |
|---|---|---|
| Column | HiTrap_Chelating_1x5_ml | |
| Pressure_limit | 0.8 | {MPa} |
| Flow | 5.00 | {ml/min} |
| UV_Averaging_time | 2.60 | |
| Start_ConcB | 0.00 | {%B} |
| Equilibrate_with | 0.2 | {CV} |
| Flowthrough_FracSize | 8 | {ml} |
| Empty_loop_with | 0 | {ml} |
| Wash_column_with | 7 | {CV} |
| Start_Frac_at | 10 | {%B} |
| Eluate_FracSize | 2 | {ml} |
| End_Frac_at | 100 | {%B} |
| Target_ConcB_1 | 100 | {%B} |
| Length_of_gradient_1 | 15 | {base} |
| Target_ConcB_2 | 0 | {%B} |
| Length_of_gradient_2 | 0.00 | {base} |
| Target_ConcB_3 | 0 | {%B} |
| Length_of_gradient_3 | 0.00 | {base} |
| Conc_of_eluent_B | 100 | {%B} |
| Clean_with | 4.00 | {CV} |
| Reequilibrate_conc | 0.00 | {%B} |
| Reequilibrate_with | 0.00 | {CV} |

Fig. 12A

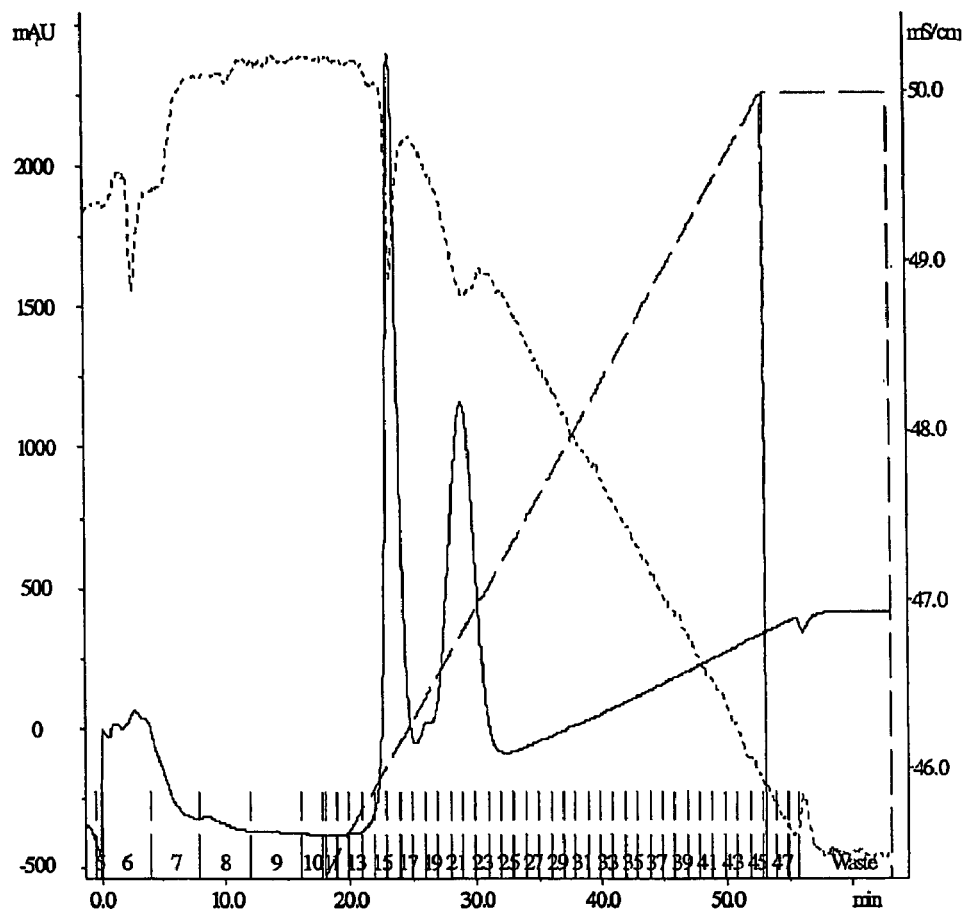

```
Column            HiTrap_Chelating_1x5_ml
Pressure_limit    0.5   {MPa}
Flow              2     {ml/min}
UV_Averaging_time 2.60
Start_ConcB       0.00  {%B}
Equilibrate_with  2     {CV}
Flowthrough_FracSize  8  {ml}
Empty_loop_with   0     {ml}
Wash_column_with  7     {CV}
Start_Frac_at     0     {%B}
Eluate_FracSize   2     {ml}
End_Frac_at       100   {%B}
Target_ConcB_1    100   {%B}
Length_of_gradient_1  14   {base}
Target_ConcB_2    0     {%B}
Length_of_gradient_2  0.00 {base}
Target_ConcB_3    0     {%B}
Length_of_gradient_3  0.00 {base}
Conc_of_eluent_B  100   {%B}
Clean_with        4.00  {CV}
Reequilibrate_conc 0.00 {%B}
Reequilibrate_with 0.00 {CV}
```

Fig. 13A

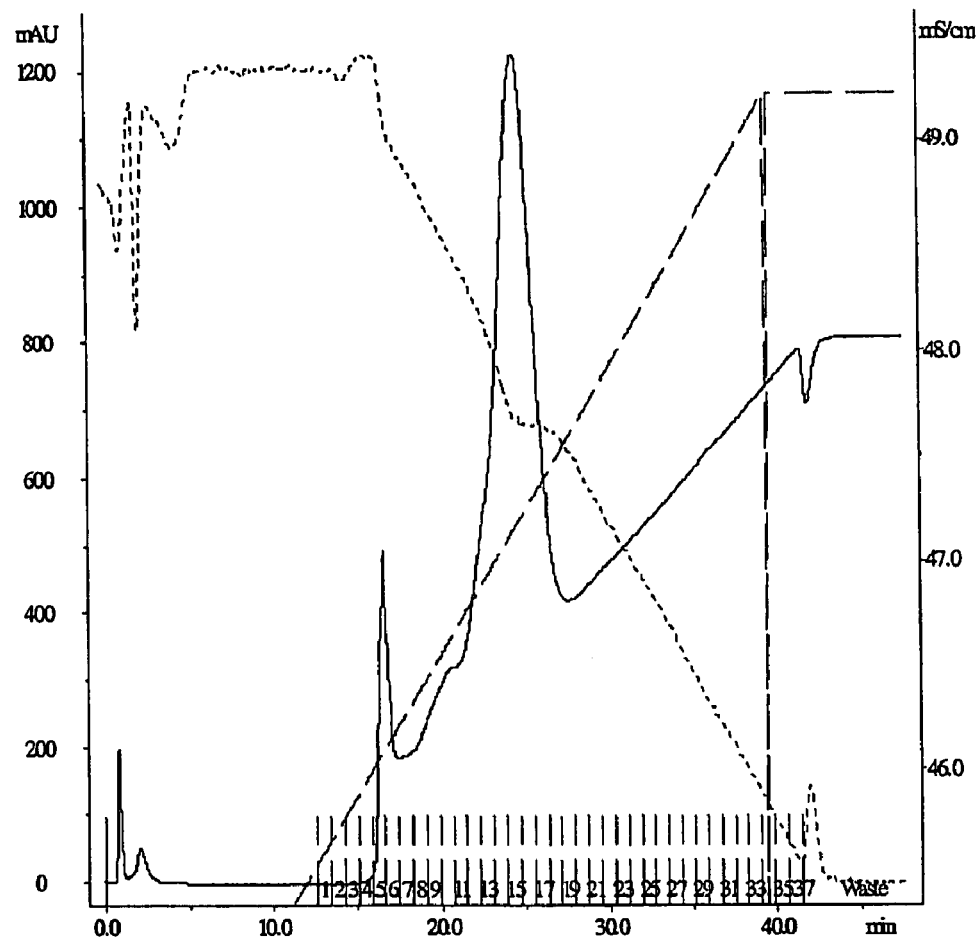

```
Column              HiTrap_Chelating_1x5_ml
Pressure_limit      0.8    {MPa}
Flow                2.5    {ml/min}
UV_Averaging_time   2.60
Start_ConcB         0.00   {%B}
Equilibrate_with    0      {CV}
Flowthrough_FracSize 0     {ml}
Empty_loop_with     0      {ml}
Wash_column_with    5.5    {CV}
Start_Frac_at       5      {%B}
Eluate_FracSize     2      {ml}
End_Frac_at         100    {%B}
Target_ConcB_1      100    {%B}
Length_of_gradient_1 14    {base}
Target_ConcB_2      0      {%B}
Length_of_gradient_2 0.00  {base}
Target_ConcB_3      0      {%B}
Length_of_gradient_3 0.00  {base}
Conc_of_eluent_B    100    {%B}
Clean_with          4.00   {CV}
Reequilibrate_conc  0.00   {%B}
Reequilibrate_with  0.00   {CV}
```

Fig. 14A

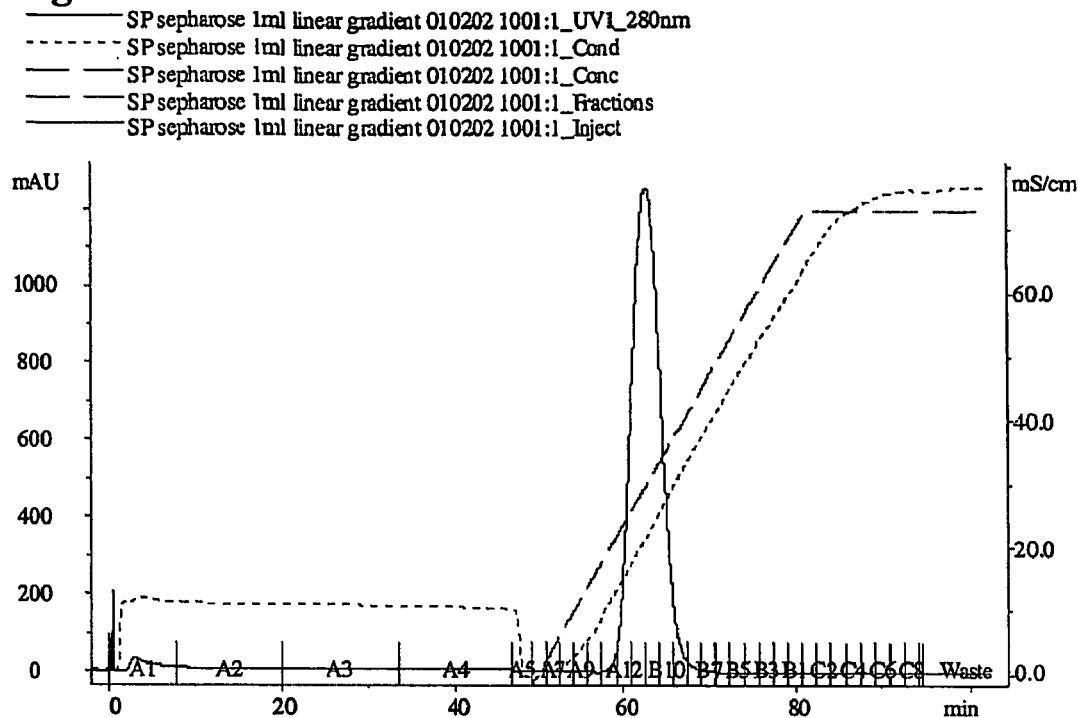

```
Column              HiTrap_SP_FF_1_ml
Flow_Rate           1.00   {ml/min}
Column_PressureLimit 0.40  {MPa}
Wavelength_1        280    {nm}
Wavelength_2        OFF    {nm}
Wavelength_3        OFF    {nm}
Averaging_Time_UV   5.12   {sec}
Pump_A_Inlet        A1
Pump_B_Inlet        B1
Wash_Inlet_A1_      OFF
Wash_Inlet_A2_      OFF
Wash_Inlet_B1_      OFF
Wash_Inlet_B2_      OFF
Start_ConcB         0      {%B}
Compensation_Volume 8      {ml}
Equilibrate_with    0      {CV}
Flowthrough_TubeType 18mm
Flowthrough_FracSize 8     {ml}
Flowthrough_StartAt FirstTube
Empty_loop_with     31.500 {ml}
Wash_column_with    2      {CV}
_Start_Frac_at      0      {%B}
_End_Frac_at        100    {%B}
TubeType_EluateFrac 18mm
Eluate_Frac_Size    1      {ml}
EluateFrac_StartAt  NextTube
Target_ConcB        100    {%B}
Length_of_Gradient  20.00  {base}
Gradient_Delay      8      {ml}
Clean_with          5.00   {CV}
```

Fig. 15A

——— SP sepharose 1ml segmented gradient 001:1_UV1_280nm
- - - - - SP sepharose 1ml segmented gradient 001:1_Cond
— — SP sepharose 1ml segmented gradient 001:1_Conc
— — SP sepharose 1ml segmented gradient 001:1_Fractions
——— SP sepharose 1ml segmented gradient 001:1_Inject

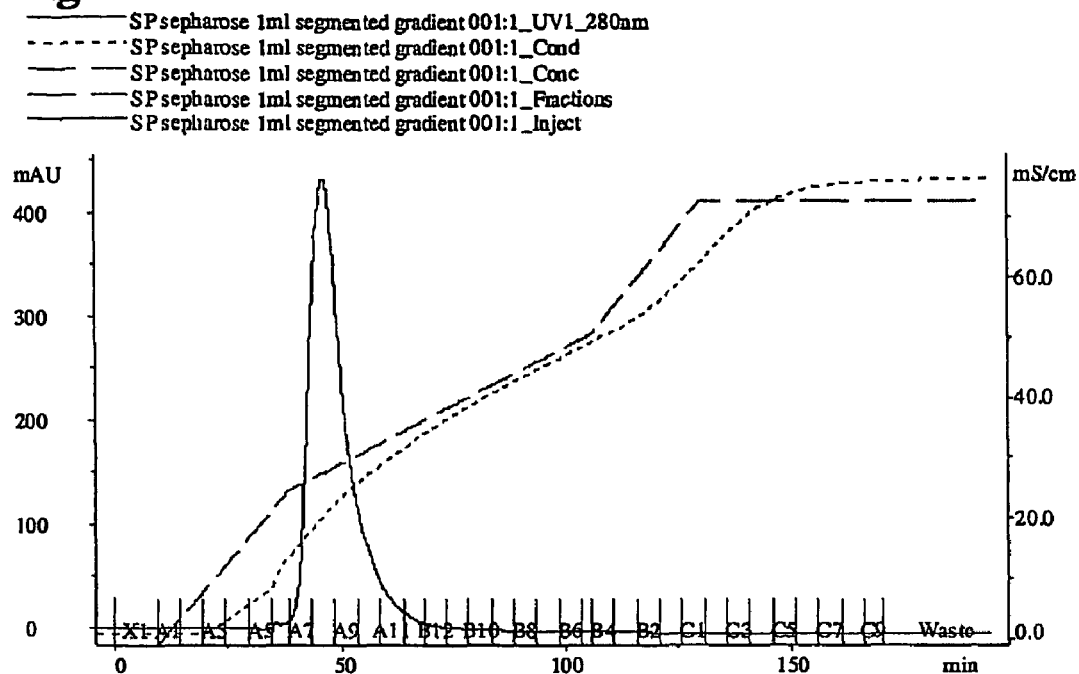

| Column | HiTrap_SP_FF_1_ml |
|---|---|
| Flow_Rate | 0.40 {ml/min} |
| Column_PressureLimit | 0.50 {MPa} |
| Wavelength_1 | 280 {nm} |
| Wavelength_2 | OFF {nm} |
| Wavelength_3 | OFF {nm} |
| Averaging_Time_UV | 5.12 {sec} |
| Pump_A_Inlet | A1 |
| Pump_B_Inlet | B1 |
| Wash_Inlet_A1_ | OFF |
| Wash_Inlet_A2_ | OFF |
| Wash_Inlet_B1_ | OFF |
| Wash_Inlet_B2_ | OFF |
| Start_ConcB | 0 {%B} |
| Compensation_Volume | 8 {ml} |
| Equilibrate_with | 0 {CV} |
| Flowthrough_TubeType | 30mm |
| Flowthrough_FracSize | 40 {ml} |
| Flowthrough_StartAt | TubeNumber[X.1] |
| Empty_loop_with | 0.000 {ml} |
| Wash_column_with | 2 {CV} |
| 1_Tube_Type | 18mm |
| 1_Fraction_Size | 1 {ml} |
| 1_Start_at | FirstTube |
| Target_ConcB_1 | 35 {%B} |
| Length_of_Gradient_1 | 6.00 {base} |
| 2_Tube_Type | 18mm |
| 2_Fraction_Size | 1 {ml} |
| 2_Start_at | NextTube |
| Target_ConcB_2 | 70 {%B} |
| Length_of_Gradient_2 | 14.00 {base} |
| 3_Tube_Type | 18mm |
| 3_Fraction_Size | 1 {ml} |
| 3_Start_at | NextTube |
| Target_ConcB_3 | 100 {%B} |
| Length_of_Gradient_3 | 5.00 {base} |
| Gradient_Delay | 8 {ml} |
| Clean_with | 5.00 {CV} |

SEQUENCE LISTING

```
<160> NUMBER OF SEQ ID NOS: 9

<210> SEQ ID NO 1
<211> LENGTH: 2002
<212> TYPE: DNA
<213> ORGANISM: Homo sapiens

<400> SEQUENCE: 1
gaattgtacg tcaaagagat gaagcagaaa aacgtcgtcg agaagaagct gaacgacaaa        60
aagtgaaatg cgagggaagt ccaagaaatg gtgattatga gggtgtctat ttcaccaaaa       120
acggagaata tttattggaa ttaagagtct ctgggactgc tcttgtaaat gctccttgta       180
atttaaagga tattgacata acgaaatggt tgtgtaaaac agggagatta tatcttgata       240
aggttaagaa atttgaaata gttactattc tttcccatga cgtagaaaat caaaagatta       300
```

```
taacagaatg ggagtcactc cccagagagg ctttacccga acaatttgat tcataagaac    360
taattagtag cgcttttccaa tggaggcgct tttttatttg ggtagttgca taccactaaa   420
gatgttcagg tgcacatgag cattggagga aaggaacgct ttaggggaa gggaaacctt     480
taaacagtct taatcccct tgattttatg ttctctgtaa actgcgtccg gtaaatctca    540
ggatagacaa tcggcggtta acggcttgag tgcggggca gtttagaaag aatatgattg    600
gagggattca tagatgcatc accatcacca tcatatgagc gccaagtcca gaaccatagg   660
gattattgga gctcctttct caaagggaca gccacgagga ggggtggaag aaggccctac   720
agtattgaga aaggctggtc tgcttgagaa acttaaagaa caagagtgtg atgtgaagga   780
ttatggggac ctgccctttg ctgacatccc taatgacagt ccctttcaaa ttgtgaagaa   840
tccaaggtct gtgggaaaag caagcgagca gctggctggc aaggtggcac aagtcaagaa   900
gaacggaaga atcagcctgg tgctgggcgg agaccacagt ttggcaattg aagcatctc    960
tggccatgcc agggtccacc ctgatcttgg agtcatctgg gtggatgctc acactgatat   1020
caacactcca ctgacaacca caagtggaaa cttgcatgga caacctgtat ctttcctcct   1080
gaaggaacta aaaggaaga ttcccgatgt gccaggattc tcctgggtga ctccctgtat   1140
atctgccaag gatattgtgt atattggctt gagagacgtg gaccctgggg aacactacat   1200
tttgaaaact ctaggcatta atacttttc aatgactgaa gtggacagac taggaattgg   1260
caaggtgatg gaagaaacac tcagctatct actaggaaga agaaaaggc caattcatct   1320
aagttttgat gttgacggac tggacccatc tttcacacca gctactgca caccagtcgt   1380
gggaggtctg acatacagag aaggtctcta catcacagaa gaaatctaca aaacagggct   1440
actctcagga ttagatataa tggaagtgaa cccatccctg gggaagacac cagaagaagt   1500
aactcgaaca gtgaacacag cagttgcaat aaccttggct tgtttcggac ttgctcggga   1560
gggtaatcac aagcctattg actaccttaa cccacctaag taaatgtgga acatccgat   1620
ataaatctca tagttaatgg cataattaga aagctaatca ttttcttaag catagagtta   1680
tccttctaaa gacttgttct ttcagaaaaa tgttttttcca attagtataa actctacaaa   1740
ttccctcttg gtgtaaaatt caagatgtgg aaattctaac ttttttgaaa tttaaaagct   1800
tatattttct aacttggcaa aagacttatc cttagaaaga gaagtgtaca ttgatttcca   1860
attaaaaatt tgctggcatt aaaaataagc acacttacat aagcccccat acatagagtg   1920
ggactcttgg aatcaggaga caaagctacc acatgtggaa aggtactatg tgtccatgtc   1980
attcaaaaaa tgtgattcta ga                                             2002
```

<210> SEQ ID NO 2
<211> LENGTH: 990
<212> TYPE: DNA
<213> ORGANISM: Artificial Sequence
<220> FEATURE:
<223> OTHER INFORMATION: Chimeric DNA sequence encoding human arginase I
    and an N-terminal histidine tag

<400> SEQUENCE: 2

```
atg cat cac cat cac cat cat atg agc gcc aag tcc aga acc ata ggg     48
att att gga gct cct ttc tca aag gga cag cca cga gga ggg gtg gaa     96
gaa ggc cct aca gta ttg aga aag gct ggt ctg ctt gag aaa ctt aaa    144
gaa caa gag tgt gat gtg aag gat tat ggg gac ctg ccc ttt gct gac    192
atc cct aat gac agt ccc ttt caa att gtg aag aat cca agg tct gtg    240
gga aaa gca agc gag cag ctg gct ggc aag gtg gca caa gtc aag aag    288
```

```
aac gga aga atc agc ctg gtg ctg ggc gga gac cac agt ttg gca att      336
gga agc atc tct ggc cat gcc agg gtc cac cct gat ctt gga gtc atc      384
tgg gtg gat gct cac act gat atc aac act cca ctg aca acc aca agt      432
gga aac ttg cat gga caa cct gta tct ttc ctc ctg aag gaa cta aaa      480
gga aag att ccc gat gtg cca gga ttc tcc tgg gtg act ccc tgt ata      528
tct gcc aag gat att gtg tat att ggc ttg aga gac gtg gac cct ggg      576
gaa cac tac att ttg aaa act cta ggc att aaa tac ttt tca atg act      624
gaa gtg gac aga cta gga att ggc aag gtg atg gaa gaa aca ctc agc      672
tat cta cta gga aga aag aaa agg cca att cat cta agt ttt gat gtt      720
gac gga ctg gac cca tct ttc aca cca gct act ggc aca cca gtc gtg      768
gga ggt ctg aca tac aga gaa ggt ctc tac atc aca gaa gaa atc tac      816
aaa aca ggg cta ctc tca gga tta gat ata atg gaa gtg aac cca tcc      864
ctg ggg aag aca cca gaa gaa gta act cga aca gtg aac aca gca gtt      912
gca ata acc ttg gct tgt ttc gga ctt gct cgg gag ggt aat cac aag      960
cct att gac tac ctt aac cca cct aag taa                              990
```

<210> SEQ ID NO 3
<211> LENGTH: 329
<212> TYPE: PRT
<213> ORGANISM: Artificial Sequence
<220> FEATURE:
<223> OTHER INFORMATION: Chimeric AA sequence of human arginase I and an
      N-terminal histidine tag

<400> SEQUENCE: 3

```
Met His His His His His His Met Ser Ala Lys Ser Arg Thr Ile Gly
  1               5                  10                  15

Ile Ile Gly Ala Pro Phe Ser Lys Gly Gln Pro Arg Gly Gly Val Glu
             20                  25                  30

Glu Gly Pro Thr Val Leu Arg Lys Ala Gly Leu Leu Glu Lys Leu Lys
         35                  40                  45

Glu Gln Glu Cys Asp Val Lys Asp Tyr Gly Asp Leu Pro Phe Ala Asp
     50                  55                  60

Ile Pro Asn Asp Ser Pro Phe Gln Ile Val Lys Asn Pro Arg Ser Val
 65                  70                  75                  80

Gly Lys Ala Ser Glu Gln Leu Ala Gly Lys Val Ala Gln Val Lys Lys
                 85                  90                  95

Asn Gly Arg Ile Ser Leu Val Leu Gly Gly Asp His Ser Leu Ala Ile
            100                 105                 110

Gly Ser Ile Ser Gly His Ala Arg Val His Pro Asp Leu Gly Val Ile
        115                 120                 125

Trp Val Asp Ala His Thr Asp Ile Asn Thr Pro Leu Thr Thr Thr Ser
    130                 135                 140

Gly Asn Leu His Gly Gln Pro Val Ser Phe Leu Leu Lys Glu Leu Lys
145                 150                 155                 160

Gly Lys Ile Pro Asp Val Pro Gly Phe Ser Trp Val Thr Pro Cys Ile
                165                 170                 175

Ser Ala Lys Asp Ile Val Tyr Ile Gly Leu Arg Asp Val Asp Pro Gly
            180                 185                 190

Glu His Tyr Ile Leu Lys Thr Leu Gly Ile Lys Tyr Phe Ser Met Thr
        195                 200                 205
```

```
Glu Val Asp Arg Leu Gly Ile Gly Lys Val Met Glu Glu Thr Leu Ser
    210                 215                 220
Tyr Leu Leu Gly Arg Lys Lys Arg Pro Ile His Leu Ser Phe Asp Val
225                 230                 235                 240
Asp Gly Leu Asp Pro Ser Phe Thr Pro Ala Thr Gly Thr Pro Val Val
                245                 250                 255
Gly Gly Leu Thr Tyr Arg Glu Gly Leu Tyr Ile Thr Glu Glu Ile Tyr
                260                 265                 270
Lys Thr Gly Leu Leu Ser Gly Leu Asp Ile Met Glu Val Asn Pro Ser
                275                 280                 285
Leu Gly Lys Thr Pro Glu Glu Val Thr Arg Thr Val Asn Thr Ala Val
    290                 295                 300
Ala Ile Thr Leu Ala Cys Phe Gly Leu Ala Arg Glu Gly Asn His Lys
305                 310                 315                 320
Pro Ile Asp Tyr Leu Asn Pro Pro Lys
                325

<210> SEQ ID NO 4
<211> LENGTH: 7
<212> TYPE: PRT
<213> ORGANISM: Artificial Sequence
<220> FEATURE:
<223> OTHER INFORMATION: 6x Histidine tag

<400> SEQUENCE: 4

Met His His His His His His
 1               5

<210> SEQ ID NO 5
<211> LENGTH: 33
<212> TYPE: DNA
<213> ORGANISM: Artificial Sequence
<220> FEATURE:
<223> OTHER INFORMATION: Synthetic oligonucleotide primer sequence

<400> SEQUENCE: 5
ccaaaccata tgagcgccaa gtccagaacc ata                              33

<210> SEQ ID NO 6
<211> LENGTH: 39
<212> TYPE: DNA
<213> ORGANISM: Artificial Sequence
<220> FEATURE:
<223> OTHER INFORMATION: Synthetic oligonucleotide primer sequence

<400> SEQUENCE: 6
ccaaactcta gaatcacatt ttttgaatga catggacac                        39

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide primer sequence

<400> SEQUENCE: 7
ctctggccat gccagggtcc accc                                        24

<210> SEQ ID NO 8
<211> LENGTH: 969
<212> TYPE: DNA
<213> ORGANISM: Homo sapiens
<220> FEATURE:
```

```
<221> NAME/KEY: CDS
<222> LOCATION: (1)...(969)

<400> SEQUENCE: 8 atg agc gcc aag tcc aga acc ata ggg att att gga gct cct ttc tca      48
Met Ser Ala Lys Ser Arg Thr Ile Gly Ile Ile Gly Ala Pro Phe Ser
1               5                   10                  15 aag gga cag cca cga gga ggg gtg gaa gaa ggc cct aca gta ttg aga      96
Lys Gly Gln Pro Arg Gly Gly Val Glu Glu Gly Pro Thr Val Leu Arg
            20                  25                  30 aag gct ggt ctg ctt gag aaa ctt aaa gaa caa gag tgt gat gtg aag     144
Lys Ala Gly Leu Leu Glu Lys Leu Lys Glu Gln Glu Cys Asp Val Lys
        35                  40                  45 gat tat ggg gac ctg ccc ttt gct gac atc cct aat gac agt ccc ttt     192
Asp Tyr Gly Asp Leu Pro Phe Ala Asp Ile Pro Asn Asp Ser Pro Phe
    50                  55                  60 caa att gtg aag aat cca agg tct gtg gga aaa gca agc gag cag ctg     240
Gln Ile Val Lys Asn Pro Arg Ser Val Gly Lys Ala Ser Glu Gln Leu
65                  70                  75                  80 gct ggc aag gtg gca caa gtc aag aag aac gga aga atc agc ctg gtg     288
Ala Gly Lys Val Ala Gln Val Lys Lys Asn Gly Arg Ile Ser Leu Val
                85                  90                  95 ctg ggc gga gac cac agt ttg gca att gga agc atc tct ggc cat gcc     336
Leu Gly Gly Asp His Ser Leu Ala Ile Gly Ser Ile Ser Gly His Ala
            100                 105                 110 agg gtc cac cct gat ctt gga gtc atc tgg gtg gat gct cac act gat     384
Arg Val His Pro Asp Leu Gly Val Ile Trp Val Asp Ala His Thr Asp
        115                 120                 125 atc aac act cca ctg aca acc aca agt gga aac ttg cat gga caa cct     432
Ile Asn Thr Pro Leu Thr Thr Thr Ser Gly Asn Leu His Gly Gln Pro
    130                 135                 140 gta tct ttc ctc ctg aag gaa cta aaa gga aag att ccc gat gtg cca     480
Val Ser Phe Leu Leu Lys Glu Leu Lys Gly Lys Ile Pro Asp Val Pro
145                 150                 155                 160 gga ttc tcc tgg gtg act ccc tgt ata tct gcc aag gat att gtg tat     528
Gly Phe Ser Trp Val Thr Pro Cys Ile Ser Ala Lys Asp Ile Val Tyr
                165                 170                 175 att ggc ttg aga gac gtg gac cct ggg gaa cac tac att ttg aaa act     576
Ile Gly Leu Arg Asp Val Asp Pro Gly Glu His Tyr Ile Leu Lys Thr
            180                 185                 190 cta ggc att aaa tac ttt tca atg act gaa gtg gac aga cta gga att     624
Leu Gly Ile Lys Tyr Phe Ser Met Thr Glu Val Asp Arg Leu Gly Ile
        195                 200                 205 ggc aag gtg atg gaa gaa aca ctc agc tat cta cta gga aga aag aaa     672
Gly Lys Val Met Glu Glu Thr Leu Ser Tyr Leu Leu Gly Arg Lys Lys
    210                 215                 220 agg cca att cat cta agt ttt gat gtt gac gga ctg gac cca tct ttc     720
Arg Pro Ile His Leu Ser Phe Asp Val Asp Gly Leu Asp Pro Ser Phe
225                 230                 235                 240 aca cca gct act ggc aca cca gtc gtg gga ggt ctg aca tac aga gaa     768
Thr Pro Ala Thr Gly Thr Pro Val Val Gly Gly Leu Thr Tyr Arg Glu
                245                 250                 255 ggt ctc tac atc aca gaa gaa atc tac aaa aca ggg cta ctc tca gga     816
Gly Leu Tyr Ile Thr Glu Glu Ile Tyr Lys Thr Gly Leu Leu Ser Gly
            260                 265                 270 tta gat ata atg gaa gtg aac cca tcc ctg ggg aag aca cca gaa gaa     864
Leu Asp Ile Met Glu Val Asn Pro Ser Leu Gly Lys Thr Pro Glu Glu
        275                 280                 285 gta act cga aca gtg aac aca gca gtt gca ata acc ttg gct tgt ttc     912
Val Thr Arg Thr Val Asn Thr Ala Val Ala Ile Thr Leu Ala Cys Phe
    290                 295                 300
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| gga | ctt | gct | cgg | gag | ggt | aat | cac | aag | cct | att | gac | tac | ctt | aac | cca | 960 |
| Gly | Leu | Ala | Arg | Glu | Gly | Asn | His | Lys | Pro | Ile | Asp | Tyr | Leu | Asn | Pro |     |
| 305 |     |     |     | 310 |     |     |     | 315 |     |     |     | 320 |     |     |     |     |

| | | | |
|---|---|---|---|
| cct | aag | taa | 969 |
| Pro | Lys | * | |

<210> SEQ ID NO 9
<211> LENGTH: 322
<212> TYPE: PRT
<213> ORGANISM: Homo sapiens

<400> SEQUENCE: 9

Met Ser Ala Lys Ser Arg Thr Ile Gly Ile Ile Gly Ala Pro Phe Ser
 1               5                  10                  15

Lys Gly Gln Pro Arg Gly Gly Val Glu Glu Gly Pro Thr Val Leu Arg
                20                  25                  30

Lys Ala Gly Leu Leu Glu Lys Leu Lys Glu Gln Glu Cys Asp Val Lys
            35                  40                  45

Asp Tyr Gly Asp Leu Pro Phe Ala Asp Ile Pro Asn Asp Ser Pro Phe
        50                  55                  60

Gln Ile Val Lys Asn Pro Arg Ser Val Gly Lys Ala Ser Glu Gln Leu
65                  70                  75                  80

Ala Gly Lys Val Ala Gln Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
        210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Cys Phe
290                 295                 300

Gly Leu Ala Arg Glu Gly Asn His Lys Pro Ile Asp Tyr Leu Asn Pro
305                 310                 315                 320

Pro Lys

PHARMACEUTICAL PREPARATION AND METHOD OF TREATMENT OF HUMAN MALIGNANCIES WITH ARGININE DEPRIVATION

RELATED APPLICATIONS

This is the U.S. National Phase under 35 U.S.C. §371 of International Application No. PCT/GB2003/002665 filed on Jun. 20, 2003, designating the United States and published in English on Dec. 31, 2003, as Publication No. WO 2004/000349 A1, which claims priority under 35 U.S.C. §119(e) to U.S. Provisional Application No. 60/390,757, filed Jun. 20, 2002, and under 35 U.S.C. §120 to International Application No. PCT/CNO2/00635, filed Sep. 9, 2002.

FIELD OF INVENTION

The present invention is related to pharmaceutical compositions containing arginase and use therefor. In particular, the present invention is related to pharmaceutical compositions that have the capability of reducing the arginine level in patients with tumours and its use for treatment of human malignancies. The present invention also relates to a method of producing a recombinant protein.

BACKGROUND OF INVENTION

Arginase I (EC 3.5.3.1; L-arginine amidinohydrolase), is a key mammalian liver enzyme that catalyses, the final step in the urea formation in the Urea cycle, converting arginine into ornithine and urea. Rat liver extract, which has a high content of arginase, was found to have anti-tumour properties in vitro when it was accidentally added to tumour cell culture medium (Burton et al., 1967, Cytolytic action of corticosteroids on thymus and lymphoma cells in vitro. Can J. Biochem. 45, 289-297). Subsequent experiments showed that the anti-tumour properties of the enzyme were due to depletion of arginine, which is an essential amino acid in the culture medium. At below 8 µM levels of arginine, irreparable cell death in cancer cells occurred (Storr & Burton, 1974, The effects of arginine deficiency on lymphoma cells. Br. J. Cancer 30, 50-59).

A more novel aspect of arginine centers on its role as the direct precursor for the synthesis of the potent signalling molecule nitric oxide (NO), which functions as a neurotransmitter, smooth muscle relaxant, and vasodilator. Biosynthesis of NO involves a $Ca^{++}$, NADPH-dependent reaction catalysed by nitric oxide synthase (NOS). Another recognized role of arginine is that it acts as a precursor, via ornithine, of the polyamines, spermidine and spermine, which participate in diverse physiologic processes including cell proliferation and growth (Wu & Morris, 1998, Arginine metabolism: nitric oxide and beyond. Biochem. J. 336, 1-17).

Arginine also serves as a substrate for several important enzymes, including nitric oxide synthase (NOS). There are three types of NOSs, nNOS, eNOS and iNOS, all convert arginine to nitric oxide and citrulline. The facial flushes induced by NO, for instance, is mediated through nNOS, the neuronal type of NOS. iNOS, the inducible NOS is produced by macrophages and the NO so produced from arginine during septicaemia causes vasodilation in endotoxic shock. eNOS, the endothelial NOS, is produced by endothelial cells in blood vessels. It converts arginine into NO, which then causes de-aggregation of platelets in the endothelial surfaces through cGMP mechanism. NO produced from eNOS in the local endQthelial lining has a half-life of about 5 seconds and diffusion distance of about 2 microns.

The productions of these enzymes are controlled by different NOS genes (NOS1, NOS2, NOS3) encoded in chromosomes 12, 17 & 7, respectively. These genes share strikingly similar genomic structures in size of exons and the location of the splice junctions.

The in vitro anti-tumour activities of arginine depletion were confirmed recently by a group in Scotland, UK (Scott et al., 2000, Single amino acid (arginine) deprivation: rapid and selective death of cultured transformed and malignanat cells. Br. J. Cancer 83, 800-810; Wheatley et al., 2000, Single amino acid (arginine) restriction: Growth and Death of cultured HeLa and Human Diploid Fibroblasts. Cellular Physiol. Biochem. 10, 37-55). Of the 24 different tumour cell lines tested, which included common cancers such as breast, colorectal, lung, prostate and ovaries, all died within 5 days of arginine depletion. Using flow-cytometry studies, the group was able to show that normal cell lines would enter into quiescence for up to several weeks in G0 phase of the cell cycle without any apparent harm. Tumour cells, however, would proceed pass the "R" point in the G1 phase and enter the S phase with deficiency of arginine. Without arginine, which is an irreplaceable amino acid, protein synthesis is deranged. Some cell lines were shown to die from apoptosis. More excitingly, repeated depletions can bringforth tumour kill without "resistance" being developed (Lamb et al., 2000, Single amino acid (arginine) deprivation induces G1 arrest associated with inhibition of Cdk4 expression in cultured human diploid fibroblasts. Experimental Cell Research 225, 238-249).

Despite the promising in vitro data, attempts with arginine depletion to treat cancer in vivo were unsuccessful. The original Storr group attempted to treat tumour-bearing rats with intraperitoneal liver extracts and met with no success (Storr & Burton, 1974, The effects of arginine deficiency on lymphoma cells. Br. J. Cancer 30, 50-59). It is now generally recognized that under normal physiological condition, the blood plasma arginine level and indeed that of other amino acids too, are kept between the normal ranges (100-120 µM) with muscle being the main regulator. In the face of amino acid deficiency, intracellular protein breakdown pathways are activated (proteasomal and lysosomal) releasing amino acids into the circulation (Malumbres & Barbacid, 2001, To cycle or not to cycle: a critical decision in cancer. Nature Reviews, 1, 222-231). This amino acid homeostatic mechanism keeps the various amino acid levels at constant ranges. Thus, previous attempts to deplete arginine with various physical methods or arginine degrading enzymes have failed because of the body's amino acid homeostatic mechanism.

To overcome the problem on the body's natural homeostatic tendencies, Tepic et al. in U.S. Pat. No. 6,261,557 described a therapeutic composition and method for treatment of cancer in which an arginine decomposing enzyme is used in combination with a protein breakdown inhibitors such as insulin in order to prevent the muscles of the body from replenishing the depleted arginine.

Although insulin can act as a protein breakdown inhibitor, it also has far-reaching physiological effects on the human body that may cause fatal problems if blood glucose levels of the patient are not strictly maintained within the narrow normal range. It is therefore an object to the present invention to find improved method of treatment and compositions for the treatment of cancer.

SUMMARY OF INVENTION

Accordingly, the present invention provides, in one aspect, an isolated and substantially purified recombinant human arginase I (hereinafter referred to as "Arginase" for ease of description unless otherwise stated) having a purity of 80-100%. In the preferred embodiment, the Arginase has a purity of between 90-100%. In the most preferred embodiment, the Arginase according to the present invention is at least 99% pure. In the example described below, the Arginase is more than 99.9% pure based on densitometry tracing after SDS-PAGE separation.

In another preferred embodiment, the Arginase of the present invention is modified to have sufficiently high enzymatic activity and stability to maintain "adequate arginine deprivation" (hereinafter referred to as "AAD") in a patient for at least 3 days. One preferred method of modification is an amino-terminal tag of six histidines. Another preferred modification is pegylation to increase the stability of the enzyme and minimise immunoreactivity illicited by the patient thereto. In the example described below, the Arginase has a plasma ½-life of at least about 3 days and specific activity of at least about 250 I.U./mg.

In another aspect of the present invention, a method is provided for producing a recombinant protein comprising the steps of (a) cloning a gene encoding the protein; (b) constructing a recombinant *Bacillus subtilis* strain for expression of said protein (c) fermenting said recombinant *B. subtilis* cells using fed-batch fermentation; (d) heat-shocking said recombinant *B. subtilis* cells to stimulate expression of said recombinant protein; and (e) purifying said recombinant protein from the product of said fermentation. In the preferred embodiment, a prophage is used as the recombinant strain. Using the fed-batch method of fermentation and prophage described above for the cloning and expression of human recombinant arginase, there is more than a 4-fold increase in maximum optical density at wavelength of 600 nm (OD) reached, and more than 5 times improvement in both the yield and productivity of the Arginase as shown in Example 3 in the next section. In a further embodiment, the fermenting step can be scaled up for producing the recombinant protein. In a further embodiment, the fermenting step is performed using a well-defined feeding medium of 180-320 g/L glucose, 2-4 g/L MgSO$_4$·7H$_2$O, 45-80 g/L tryptone, 7-12 g/L K$_2$HPO$_4$ and 3-6 g/L KH$_2$PO$_4$. The use of a well-defined medium prevents undesirable material from being purified together with the recombinant protein, making the method safe and efficient for the production of pharmaceutical grade recombinant material.

In yet another preferred embodiment, the human Arginase gene is provided with an additional coding region that encodes six additional histidines at the amino-terminal end thereof, and the purifying step comprises a chelating column chromatography step. In a further preferred embodiment, the Arginase enzyme is further modified by pegylation to improve stability.

In another aspect of the present invention, there are further provided pharmaceutical compositions comprising Arginase. In the preferred embodiment, the Arginase has sufficiently high enzymatic activity and stability to maintain AAD in a patient for at least 3 days. In the most preferred embodiment, the Arginase is further modified by pegylation to improve stability and minimise immunoreactivity.

According to another aspect of the present invention, a pharmaceutical composition is further formulated using Arginase.

In yet another aspect of the present invention, a method for treatment of a disease is provided comprising administering a formulated pharmaceutical composition of the present invention to a patient to maintain the arginine level in such a patient to below 10 μM for at least 3 days without the need for other protein breakdown inhibitors. In one of the preferred embodiments, no insulin is administered exogenously for non-diabetic patients.

Furthermore, the most preferred treatment method of the present invention involves the monitoring of the patient's blood for platelet count (preferably maintained above 50,000×10$^9$) and prothrombin time (maintained no more than 2 times normal). No nitric oxide producer is exogenously administered unless these levels of platelet count and prothrombin time are not reached.

In another preferred embodiment of this aspect of the present invention, pegylated Arginase is given as short infusion of over 30 minutes at 3,000-5,000 I.U./kg in short infusion. arginine levels and Arginase activity are taken before Arginase infusion and daily thereafter. If AAD is not achieved on day 2, the dose of the next infusion of Arginase is under the discretion of the treating physician. The maximum tolerated duration of AAD is defined as the period of time during which blood pressure is under control (with or without medication as deem appropriate by the treating physician), platelet count above 50,000×10$^9$ and prothrombin time less than 2× normal. As with arginine levels, complete blood count (CBC) and prothrombin time (PT) are taken daily. Liver chemistry is monitored at least twice weekly during the treatment.

The experimental data provided in the following detailed description shows that arginase, if provided at sufficiently potent form, is useful for the treatment of maligancies. Although recombinant human arginase I is the specific embodiment of an arginase that is used for the present disclosure, it is clear that other forms of arginase and/or from other sources may be used in accordance with the present invention.

BRIEF DESCRIPTION OF DRAWINGS

FIGS. 2A, 2B and 2C show nucleotide sequence and its deduced amino acid sequence of the human Arginase I. FIG. 2A shows the nucleotide sequence (SEQ ID NO: 1) from EcoRI/MunI to XbaI sites of plasmid pAB101. Nucleotide (nt) 1-6, EcoRI/MunI site; nt 481-486, -35 region of promoter 1; nt 504-509, -10 region of promoter 1; nt 544-549, -35 region of promoter 2; nt 566-571, -10 region of promoter 2; nt 600-605, ribosome binding site; nt 614-616, start codon; nt 632-637, NdeI site; nt 1601-1603, stop codon; nt 1997-2002, XbaI site.

FIG. 2B shows the encoding nucleotide sequence (SEQ ID NO: 2) and its corresponding encoded amino acid sequence (SEQ ID NO: 3) of a modified human Arginase. Nucleotide 614-1603 from FIG. 2A is a encoding region for the amino acid sequence of the modified Arginase. The 6×His (SEQ ID NO: 4) tag at the N-terminus is underlined. Translation stop codon is indicated by asterisk.

FIG. 2C shows the encoding nucleotide sequence (SEQ ID NO:8) and its corresponding encoded amino acid sequence (SEQ ID NO:9) of the normal human Arginase I.

FIG. 4A shows the results obtained from the batch fermentation. FIG. 4B shows the results obtained from the fed-batch fermentation.

FIG. 5A shows the history plot from the batch fermentation. FIG. 5B shows the history plot from the fed-batch fermentation.

FIGS. 6A and 6B show the results of biochemical purification of human Arginase at 3 h after heat shock by the first 5-ml HiTrap Chelating column. FIG. 6A shows the FPLC running parameters and protein elution profile. FIG. 6B shows the SDS-PAGE (12%) analysis of 5 µl of each of the fractions 11-31 collected from the column. The protein gel was stained with coomassie brilliant blue and destained to show the protein bands. Lane M: low-range molecular weight marker (1 µg per band; Bio-Rad), with MW (Daltons): 97,400; 66,200; 45,000; 31,000; 21,500; 14,400.

FIGS. 7A and 7B show results of purification of the human Arginase at 3 h after heat shock by the second 5-ml HiTrap Chelating column. FIG. 7A shows the FPLC running parameters and protein elution profile. FIG. 7B shows the SDS-PAGE (12%) analysis of 1 µl of each of the fractions 9-39 collected from the column. The protein gel was stained with coomassie brilliant blue and destained to show the protein bands. Lane M: low-range molecular weight marker (1 µg per band; Bio-Rad), with MW (Daltons): 97,400; 66,200; 45,000; 31,000; 21,500; 14,400.

FIGS. 8A and 8B show results of purification of the human Arginase at 6 h after heat shock by the first 5-ml HiTrap Chelating column. FIG. 8A shows FPLC running parameters and protein elution profile. FIG. 8B shows the SDS-PAGE (12%) analysis of 2.5 µl of each of the fractions 10-32 collected from the column. The protein gel was stained with coomassie brilliant blue and destained to show the protein bands. Lane M: low-range molecular weight marker (1 µg per band; Bio-Rad), with MW (Daltons): 97,400; 66,200; 45,000; 31,000; 21,500; 14,400.

FIGS. 9A and 9B show results of purification of the human Arginase at 6 h after heat shock by the second 5-ml HiTrap Chelating column. FIG. 9A shows FPLC runing parameters and protein elution profile. FIG. 9B shows the SDS-PAGE (12%) analysis of 2 µl of each of the fractions 8-E6 collected from the column. The protein gel was stained with coomassie brilliant blue and destained to show the protein bands. Lane M: low-range molecular weight marker (1 µg per band; Bio-Rad), with MW (Daltons): 97,400; 66,200; 45,000; 31,000; 21,500; 14,40.

FIGS. 12A and 12B show the results of purification of the human Arginase at 6 h after heat shock (at a higher cell density of OD 25) by the first 5-ml HiTrap Chelating column. FIG. 12A shows FPLC running parameters and protein elution profile. FIG. 12B shows results of SDS-PAGE (12%) analysis of 5 µl of each of the fractions 16-45 collected from the column. The protein gel was stained with coomassie brilliant blue and destained to show the protein bands. Lane M: low-range molecular weight marker (1 µg per band; Bio-Rad), with MW (Daltons): 97,400; 66,200; 45,000; 31,000; 21,500; 14,400. Lane "crude": 5 µl of the crude cell extract before loading the column.

FIGS. 13A and 13B show the results of purification of the human Arginase at 6 h after heat shock (at a higher cell density of OD 25) by the second 5-ml HiTrap Chelating column. FIG. 13A shows FPLC running parameters and protein elution profile. FIG. 13B shows the SDS-PAGE (12%) analysis of 5 µl of each of the fractions 7-34 collected from the column. The protein gel was stained with coomassie brilliant blue and destained to show the protein bands. Lane M: low-range molecular weight marker (1 µg per band; Bio-Rad), with MW (Daltons): 97,400; 66,200; 45,000; 31,000; 21,500; 14,400.

FIGS. 14A and 14B show the results of purification of the human Arginase at 6 h after heat shock (at a higher cell density of OD 25) by the first 1-ml HiTrap SP FF column. FIG. 14A shows FPLC running parameters and protein elution profile. FIG. 14B shows the SDS-PAGE (12%) analysis of 5 µl of each of the fractions A11-B7 collected from the column. The protein gel was stained with coomassie brilliant blue and destained to show the protein bands. Lane M: low-range molecular weight marker (1 µg per band; Bio-Rad), with MW (Daltons): 97,400; 66,200; 45,000; 31,000; 21,500; 14,400.

FIGS. 15A and 15B show the purification of the human Arginase at 6 h after heat shock (at a higher cell density of OD 25) by the second 1-ml HiTrap SP FF column. FIG. 15A shows the FPLC running parameters and protein elution profile. FIG. 15B shows the SDS-PAGE (12%) analysis of 5 µl of each of the fractions A6-B12 collected from the column. The protein gel was stained with coomassie brilliant blue and destained to show the protein bands. Lane M: low-range molecular weight marker (1 µg per band; Bio-Rad), with MW (Daltons): 97,400; 66,200; 45,000; 31,000; 21,500; 14,400.

FIG. 16A shows the results when reactions were performed on ice. Lane 1: low-range protein marker; Lane 2: Arginase (5.35 µg) without PEG added (control); Lane 3: 1 h after reaction; Lane 4: 0.5 h after reaction; Lane 5: 2 h after reaction; Lane 6: 3 h after reaction; Lane 7: 4 h after reaction; Lane 8: 5 h after reaction; Lane 9: 23 h after reaction. FIG. 16B shows the results when reactions were performed at room temperature. Lane 1: low-range protein marker, Lane 2: Arginase (5.35 µg) without PEG added (control); Lane 3: 1 h after reaction; Lane 4: 0.5 h after reaction; Lane 5: 2-h after reaction; Lane 6: 3 h after reaction; Lane 7: 4 h after reaction; Lane 8: 5 h after reaction; Lane 9: 23 h after reaction.

FIG. 17A shows the results when reactions were performed on ice. Lane 1: low-range protein marker; Lane 2: Arginase (5.35 µg) without PEG added (control); Lane 3: 1 h after reaction; Lane 4: 0.5 h after reaction; Lane 5: 2 h after reaction; Lane 6: 3 h after reaction; Lane 7: 4 h after reaction; Lane 8: 5 h after reaction; Lane 9: 23 h after reaction. FIG. 17B shows the results when reactions were performed at room temperature. Lane 1: low-range protein marker; Lane 2: Arginase (5.35 µg) without PEG added (control); Lane 3: 1 h after reaction; Lane 4: 0.5 h after reaction; Lane 5: 2 h after reaction; Lane 6: 3 h after reaction; Lane 7: 4 h after reaction; Lane 8: 5 h after reaction; Lane 9: 23 h after reaction.

FIG. 19A shows that for Lane 1: 5 µg of purified *E. coli*-expressed recombinant human Arginase obtained from methods described by Ikemoto et al. (Ikemoto et al., 1990, Biochem. J. 270, 697-703). Lane 2: 5 µg of purified *B. subtilis*-expressed recombinant human Arginase obtained from methods described in this report. FIG. 19B shows the analysis of densities of protein bands shown in FIG. 19A with the Lumianalyst 32 program of Lumi-imagerm (Roche Molecular Biochemicals). Upper panel: results from lane 1 of FIG. 19A. Lower panel: results from lane 2 of FIG. 19A.

FIG. 21 shows the in vivo activity of the pegylated Arginase produced according to the present invention using the activity test described in Example 9A.

FIG. 22 is a plot from which the first half-life and the second half-life of the pegylated Arginase are determined.

DETAILED DESCRIPTION

Figure 1:
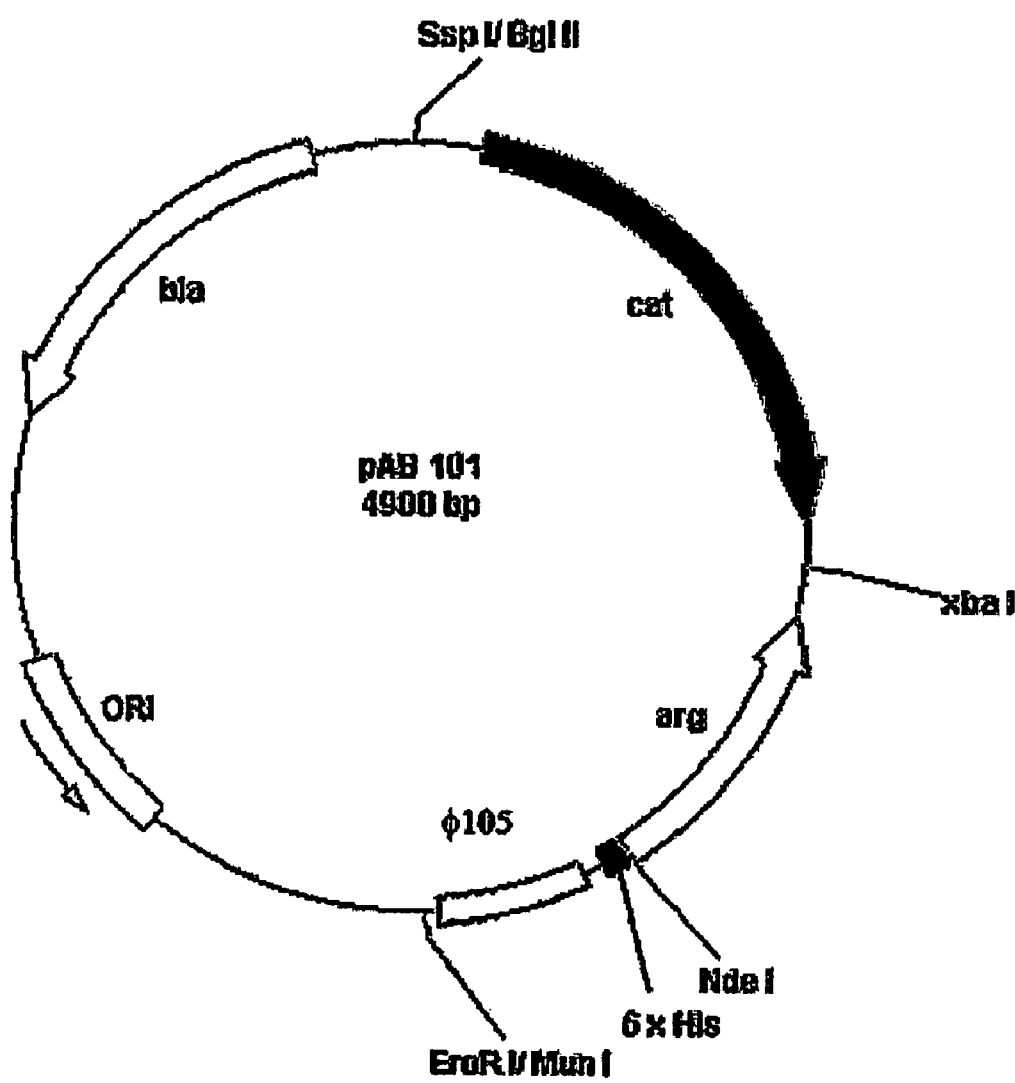
FIG. 1 shows plasmid map of pAB101. This plasmid carries the gene encoding Arginase (arg) and only replicates in *E. coli* but not in *B. subtilis*.

As used herein, the term "pegylated Arginase" refers to Arginase I of present invention modified by pegylation to increase the stability of the enzyme and minimise immunoreactivity.

As used herein, the phrase "substantially the same", whether used in reference to the nucleotide sequence of DNA, the ribonucleotide sequence of RNA, or the amino acid sequence of protein, refers to sequences that have slight and non-consequential sequence variations from the actual sequences disclosed herein. Species with sequences that are substantially the same are considered to be equivalent to the disclosed sequences and as such are within the scope of the appended claims. In this regard, "slight and non-consequential sequence variations" means that sequences that are substantially the same as the DNA, RNA, or proteins disclosed and/or claimed herein are functionally equivalent to the sequences disclosed and/or claimed herein. Functionally equivalent sequences will function in substantially the same manner to produce substantially the same compositions as the nucleic acid and amino acid compositions disclosed and claimed herein. In particular, functionally equivalent DNAs encode proteins that are the same as those disclosed herein or proteins that have conservative amino acid variations, such as substitution of a non-polar residue for another non-polar residue or a charged residue for a similarly charged residue. These changes include those recognized by those of skill in the art not to substantially alter the tertiary structure of the protein. The term "sufficiently high enzymatic activity" refers to the enzyme specific activity of the recombinant human Arginase for at least 250 I.U./mg, preferably at least 300-350 I.U./mg, more preferably at least 500 I.U./mg. In the preferred embodiment, the Arginase has a specific activity of 500-600 I.U./mg. The term "stability" refers to in vitro stability of the Arginase. More preferably, the stability refers to in vivo stability. The rate of decrease of enzyme activity is inversely proportional to the plasma stability of the isolated, purified recombinant human Arginase. The half-life of such a human Arginase in plasma is calculated.

As used herein, the term "adequate arginine deprivation" (AAD) refers to in vivo arginine level at or below 10 µM. The term "disease" refers to any pathological conditions, including but not limited to liver diseases and cancer.

As used herein, the term "half-life" (½-life) refers to the time that would be required for the concentration of the Arginase in human plasma in vitro, to fall by half. In early 2001, three cases of spontaneous transient remission of hepatocellular carcinoma (HCC) were observed by one of the inventors of the present invention. All three patients had spontaneous rupture of HCC with resulting haemoperitoneum. In one case, the plasma arginine was found to be as low as 3 µM and arginine level in the ascitic fluid at 7 µM. These patients all had spontaneous remission of their liver tumour with normalization of alpha-fetoprotein (AFP) after ruptured liver lesions in the absence of any treatment using any pharmaceutical drugs. One patient had remission of his HCC for over 6 months. In accordance with the present invention, it is believed that such prolonged remission is caused by arginine depletion due to the spontaneous and sustained release of endogenous Arginase into the peritoneum from the rupture of the liver. Thus, the inventors inferred that prolonged arginine depletion was the causative factor leading to remission of HCC.

A series of experiments was then designed by the inventor of the present invention to show that endogenous hepatic Arginase can be released from the liver after transhepatic arterial embolisation causing systemic arginine deprivation. This has now been filed in the U.S. provisional patent application No. 60/351,816, which is incorporated by reference herewith. In the experiments designed by the inventor, moderate and measurable amount of endogenous hepatic arginase was found to be released into the systemic circulation in patients with unresectable metastatic HCC after hepatic arterial embolisation treatment using lipiodol and gel foam that caused a temporary hepatic perfusion defect. High dose insulin infusion was incorporated into the treatment regime to induce a state of hypoaminoacidemia. In a series of 6 cases of HCC treated, 4 had extra hepatic remission of liver cancer suggesting the treatment effects are systemic. One patient had sustained complete remission, both radiological with CT and PET in his liver and extrahepatic disease (celiac adenopathy). His AFP level dropped to normal within 3 weeks and sustained for over 4 months. Interval CT at 4 months showed no demonstrable tumour both hepatic or extrahepatic. The other 3 patients all had remission of their extra hepatic disease (one pulmonary, one mesenteric/retroperitoneal/bone and one retroperitoneal adenopathy) on PET scan at 4 weeks after embolisation. On testing their Arginase activities and arginine levels, all had adequate arginine depletion for a period of time lasting from 2 hours to 2 days. In fact the duration of AAD correlated well with the degree and duration of remission of the tumour, both hepatic and extra-hepatic.

Although the transhepatic arterial embolisation technique was performed in conjunction with high doses of insulin infusion, the inventors, in accordance with the present invention, subsequently came to the realisation that the need for the administration of insulin was due to the fact that insufficient arginase activities may be released into the system of the patient such that any protein degradation from the muscle would have a compensatory effect from the arginine deprivation and render the treatment ineffective. In accordance with the present invention, the inventors realised that in order to improve the treatment and to eliminate the need for administration of insulin in conjunction with the arginine deprivation treatment, arginase activity has to be present in sufficiently high amounts in the patient's system in order to counteract any protein degradation from the muscle. In accordance with the present invention, the inventors therefore set out to produce an Arginase enzyme that had sufficiently high enzymatic activities and stability to maintain "adequate arginine deprivation" hereinafter referred to as "AAD") of below 10 µM in the patient without the need to administrate high dose of insulin. Thus, in addition to augmenting the endogenous Arginase, the highly stable and active Arginase according to the present invention provides the additional benefit of allow AAD to be attained without the administration of a protein degradation inhibitor, which has undesirable side effects on the patient.

Systemic depletion of arginine may cause other undesirable side effect related to nitric oxide deficiency. These include hypertension due to absence of vasodilator effect of NO on vascular endothelium, platelet aggregation and thrombocytopenia secondary to lack of NO and depletion of early clotting factors related to temporary cessation of cell division. The inventor recognized, however, that in nitric oxide knock out mice the animals are not hypertensive and have normal life expectance with normal platelet counts. Thus, in accordance with another aspect of the present invention and in patients with thrombocytopenia, no overt haemorrhagic tendency is seen until platelet count is well below $50,000 \times 10^9$. In patients with thrombotic tendency, therapy entails prolonging the prothrombin time for up to 2× normal.

The following detailed examples teach how to make and use a highly stable and active Arginase according to the present invention. Example 1 describes the construction of the recombinant strain of *Bacillus subtilis* LLC101 containing the human Arginase I gene. This is followed by two examples of fermentation of the recombinant *B. subtilis*. In the initial fermentation experiments of the recombinant LLC101 cells, batch fermentation and fed-batch fermentation were conducted in a 2-L fermentor. It was found that under batch conditions sufficiently high cell density could not be attained. Only under the fed-batch conditions provided in accordance with the present invention would cell density be increased to above 10 OD (optical density). These experiments and results are shown in Examples 2A and 2B. A comparison of the 2 fermentation methods is shown in Example 3. Fed-batch fermentation operation was thus chosen for production of isolated and purified recombinant human Arginase. The fed-batch fermentation was scaled up in a 100-L fermentor. The experiments and results are shown in Example 2C.

The LLC101 strain is a heat sensitive strain that causes expression of the Arginase upon heat shock at 50° C. In the initial optimisation experiments, the heat shock treatment was performed at varying cell densities to obtain the optimal conditions under which maximum Arginase would be produced. Examples 5 and 6 describe the purification process and the yield of purified Arginase thus obtained of two different fed-batch fermentation runs with heat shock at two different OD (optical density at 600 nm), 12.8 and 25. The experimental data showed that although all heat shocks were applied during the exponential growth phase of the LLC101, introduction of heat shock at a lower cell density, e.g., 12.8 OD, produced better results.

Conditions for maximum expression of Arginase after heat shock was also optimised by varying the time of harvest after heat shock. Example 4 shows results from harvesting the cells three hours after heat shock and using a fed-batch fermentation process.

Example 5 describes a purification of Arginase 6 hours after heat shock at a cell density of 12.8 OD. Example 6 describes the purification of Arginase 6 hours after heat shock at a higher cell density of 25OD. Example 7 shows a comparison of the data to compare the yield of the Arginase under various harvesting and purification conditions. These data show that harvesting cells 6 h after heat shock at a lower cell density of 12.8 produced a higher Arginase yield of 162 mg/L. The Arginase was modified to improve stability. Example 8A shows one protocol for the pegylation of the Arginase using cyanuric chloride (cc) as the cross-linker at an ratio of 1:140 (Arginase:PEG) mole ratio. Example 8B describes a different pegylation protocol in which a much lower proportion of cross-linker is added into the reaction mixture with the enzyme. Both cc and succinimide of propionic acid (SPA) were tested as cross-linker. Experimental results show that the method as described in Example 8B using SPA provided a pegylated Arginase with a 12-life of 3 days and a specific activity of approximately 255 I.U./mg as discussed in Examples 9 and 10. Example 8C describes a method for preparing a highly active pegylated Arginase, which has a specific activity of about 592 I.U./mg.

Using the method as described above, a highly stable and active Arginase has been produced. It has sufficiently high activity and stability to allow treatment of patients without significant use of a protein degradation inhibitor because any replenishment of arginine by the muscle would be quickly removed by the systemic Arginase. Thus, adequate arginine deprivation of below 10 µM can be achieved without high doses of exogenously administered insulin. Various treatment protocols using the Arginase according to the present invention is described in Example 11. Example 12 illustrates the clinical data of a patient administered with Arginase to further support the treatment protocol shown in Example 11.

Examples 13 to 14 are two animal studies on rats investigating dose responses and safety doses of the Arginase according to the present invention. Examples 15 to 18 are another series of animal studies on nude mice to investigate the responses of tumours induced by different human cancer cell lines upon arginine depletion induced by administration of modified Arginase.

All references cited above are incorporated by reference herein. The practice of the invention is exemplified in the following non-limited Examples. The scope of the invention is defined solely by the appended claims, which are in no way limited by the content or scope of the Examples.

EXAMPLES

Example 1

Construction of the Recombinant Strain LLC101

(a) Isolation of the Gene Encoding Human Arginase I

The gene sequence of human Arginase I was published in 1987 (Haraguchi, Y. et al., 1987, Proc. Natl. Acad. Sci. 84, 412-415) and primers designed therefrom. Polymerase chain reaction (PCR) was performed to isolate the gene encoding a human Arginase using the Expand High Fidelity PCR System Kit (Roche). Primers Arg1 (5'-CCAAAC CATATGAGCGCCAAGTCCAGAACCATA-3') (SEQ ID NO: 5) and Arg2 (5'-CCAAAC TCTAGAATCACA=TTTGAATGACATGGACAC-3') (SEQ ID NO: 6), respectively, were purchased from Genset Singapore Biotechnology Pte Ltd. Both primers have the same melting temperature (Tm) of 72 degree C. Primer Arg1 contains a NdeI restriction enzyme recognition site (underlined) and primer Arg2 contains a XbaI site (underlined). These two primers (final concentration 300 nM of each) were added to 5 µl of the human liver 5'-stretch plus cDNA library (Clontech) in a 0.2-ml micro-tube. DNA polymerase (2.6 units, 0.75 µl), the four deoxyribonucleotides (4 µl of each; final concentration 200 µM of each) and reaction buffer (5 µl) and dH$_2$O (17.75 µl) were also added. PCR was performed using the following conditions: pre-PCR (94 degree C., 5 min), 25 PCR cycles (94 degree C., 1 min; 57 degree C., 1 min; 72 degree C., 1 min), post-PCR (72 degree C., 7 min). PCR product (5 µl) was analyzed on a 0.8% agarose gel and a single band of 1.4 kb was observed. This DNA fragment contains the gene encoding Arginase.

(b) Isolation of Plasmid pSG1113

Plasmid pSG1113, which is a derivative of plasmid pSG703 (Thornewell, S. J. et al., 1993, Gene, 133, 47-53), was isolated from the E. coli DH5a clone carrying pSG1113 by using the Wlizard Plus Minipreps DNA Purification System (Promega) following the manufacturer's instruction. This plasmid, which only replicates in E. coli but not in B. subtilis, was used as the vector for the subcloning of the Arginase gene.

(c) Subcloning the 1.4 kb PCR Product into Plasmid pSG1113 to Form Plasmid pAB101

The PCR product, prepared using the above protocol, was treated with restriction endonucleases NdeI and XbaI (Promega) in a reaction medium composed of 6 mM Tris-HCl (pH 7.9), 6 mM MgCl$_2$, 150 mM NaCl, 1 mM DTT at 37 degree C. for 1.5 h. After completion of the treatment, the reaction mixture was subjected to agarose gel (0.8%) electrophoresis, and the 1.4 kb DNA fragment was recovered from the gel by using the Qiaex II Gel Extraction Kit (Qiagen). Separately, the plasmid pSG1113 was treated with the same restriction endonucleases in the same way. After completion of the treatment, the reaction mixture was subjected to agarose gel (0.8%) electrophoresis, and a DNA fragment having a size of about 3.5 kb was recovered from the gel. This DNA fragment was joined by using T4 DNA ligase to the above 1.4 kb DNA fragment. The ligation mixture was used to transform E. coli XLI-Blue using the conventional calcium method (Sambrook, J. et al., Molecular Cloning, A Laboratory Manual, second edition, Cold Spring Harbor Laboratory Press, New York, 1989) and plated on nutrient agar plate containing 100 µg/ml ampicillin. Colonies were screened for a plasmid with the appropriate insert by restriction analysis. The plasmid constructed was designated pAB101 (FIG. 1). OR1 is the E. coli origin of replication and bla is the ampicillin resistant marker gene. DNA sequencing was performed with primers Arg1 (SEQ ID NO: 5), Arg2 (SEQ ID NO:6) and Arg6 (5'-CTCTGGCCATGCCAGGGTCCACCC-3') (SEQ ID NO: 7) to confirm the identity of the gene encoding Arginase (FIG. 2).

(d) Construction of the Novel Recombinant B. subtilis Prophage Strain LLC101

Figure 3:
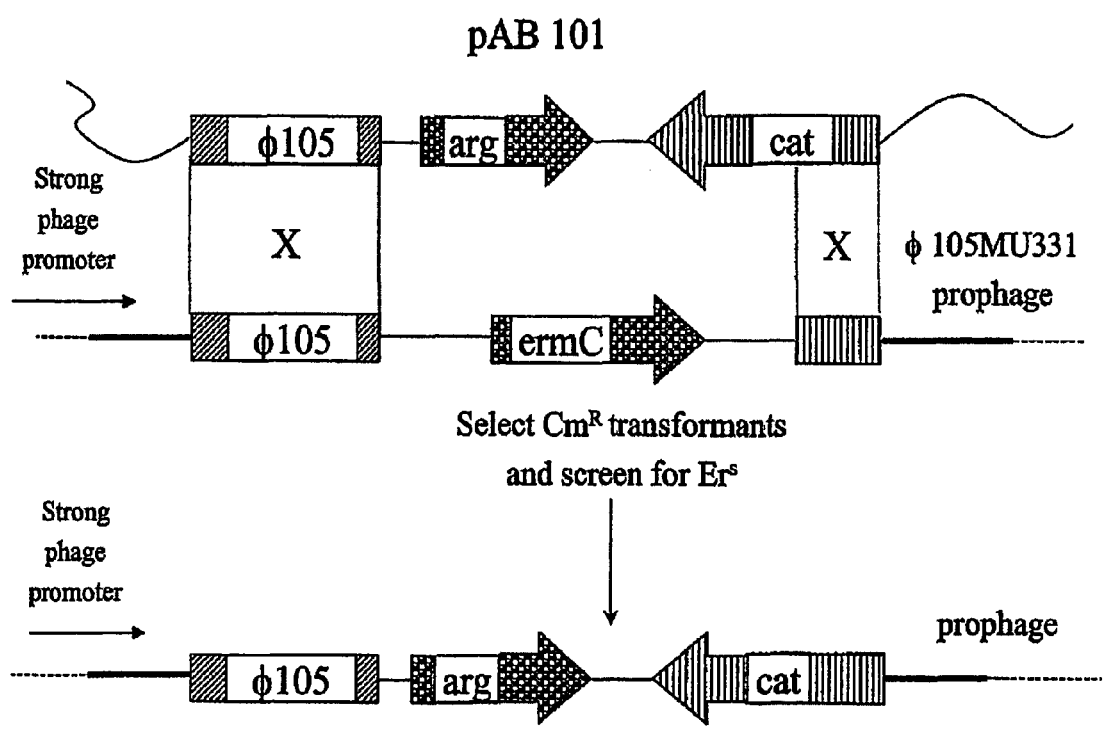
FIG. 3 is a schematic drawing of the construction of a *B. subtilis* prophage allowing expression of Arginase.

The plasmid pAB101 was extracted and purified from the clone carrying the pAB101 by using the Wizard Plus Minipreps DNA Purification System (Promega). In the plasmid pAB101 (FIG. 1), the Arginase gene (arg) was flanked by the 0.6 kb MunI-NdeI φ105 phage DNA fragment (labelled as "φ105") and the cat gene (FIG. 1 and FIG. 3). This plasmid DNA (1 µg) was used to transform competent B. subtilis 1A304(φ105MU331) according to the known method (Anagnostopoulos C. and Spizizen J., 1961, J. Bacteriol. 81, 741-746). The B. subtilis strain 1A304(φ105MU331) was obtained from J. Errington (Thornewell, S. et al., 1993, Gene 133, 47-53). The strain was produced according to the publications by Thornewell, S. et al., 1993, Gene 133, 47-53 and by Baillie, L. W. J. et al., 1998, FEMS Microbiol. Letters 163, 43-47, which are incorporated herein in their entirety. Plasmid pAB101 (shown linearized in FIG. 3) was transformed into the B. subtilis strain 1A304 (φ105MU331) with selection for the CmR marker, and the transformants were screened for an Ers phenotype. Such transformants should have arisen from a double-crossover event, as shown in FIG. 3, placing transcription of the Arginase gene (arg) under the control of the strong phage promoter (Leung and Erington, 1995, Gene 154, 1-6). The thick lines represent the prophage genome, broken lines the B. subtilis chromosome, and thin lines plasmid DNA. The genes are shown in FIG. 3 as shaded arrows pointing in the direction of transcription and translation. Regions of homology are bounded by broken vertical lines and homologous recombination events by 'X'.

Fifty-two chloramphenicol resistant (Cm$^R$) colonies were obtained from plating 600 µl of the transformed cells on an agar plate containing chloramphenicol (5 µg/ml). Ten of these colonies were selected randomly and streaked onto an agar plate containing erythromycin (20 µg/ml) and one of these colonies did not grow, indicating that it was erythromycin sensitive (Er$^s$). This chloramphenicol resistant but erythromycin sensitive colony was thus isolated and named as LLC101. In the chromosome of this newly constructed prophage strain, the erythromycin resistance gene (ermC) was replaced by the Arginase gene (arg) by a double crossover event in a process of homologous recombination. The 0.6 kb MunI-NdeI φ105 phage DNA fragment (labelled as "φ105") and the cat gene provided the homologous sequences for the recombination. In this way, the Arginase gene was targeted to the expression site in the prophage DNA of B. subtilis 1A304 (φ105MU331) and the Arginase gene was put under the control of the strong thermoinducible promoter (Leung, Y. C. and Errington, J., 1995, Gene 154, 1-6).

Fermentation of B. subtilis LLC101 Cells

Example 2A

Batch Fermentation in a 2-Liter Fermentor

Figure 4A:
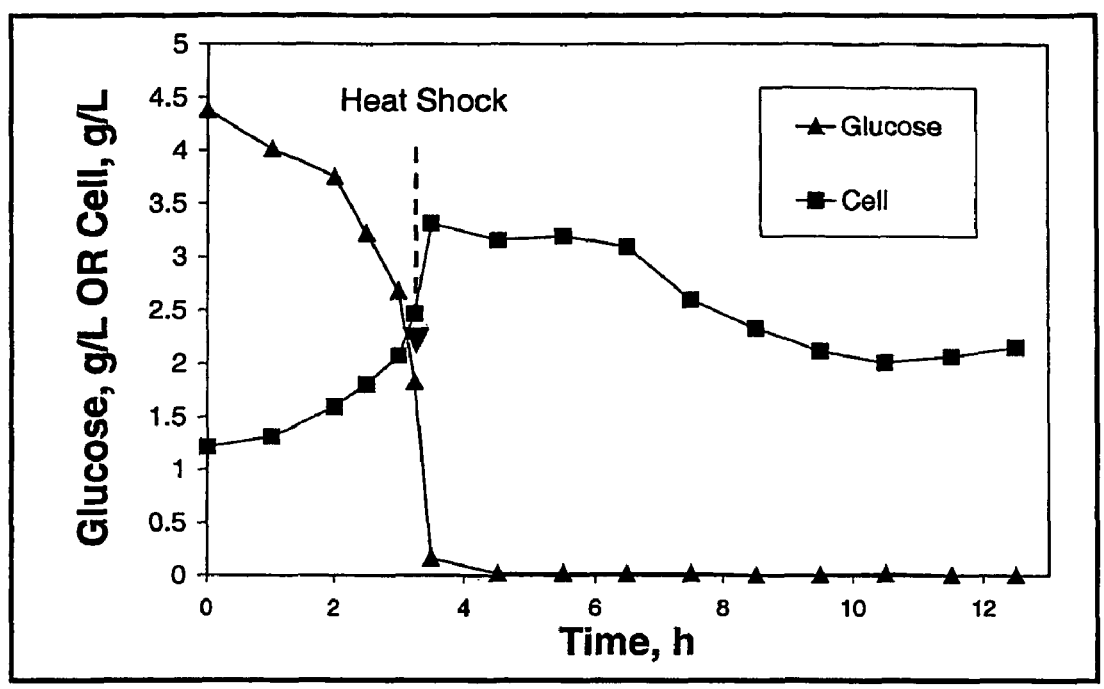
FIGS. 4A and 4B show the time-course for fermentation in a 2-liter fermentor by the recombinant *Bacillus subtilis* strain LLC101.
Figure 5A:
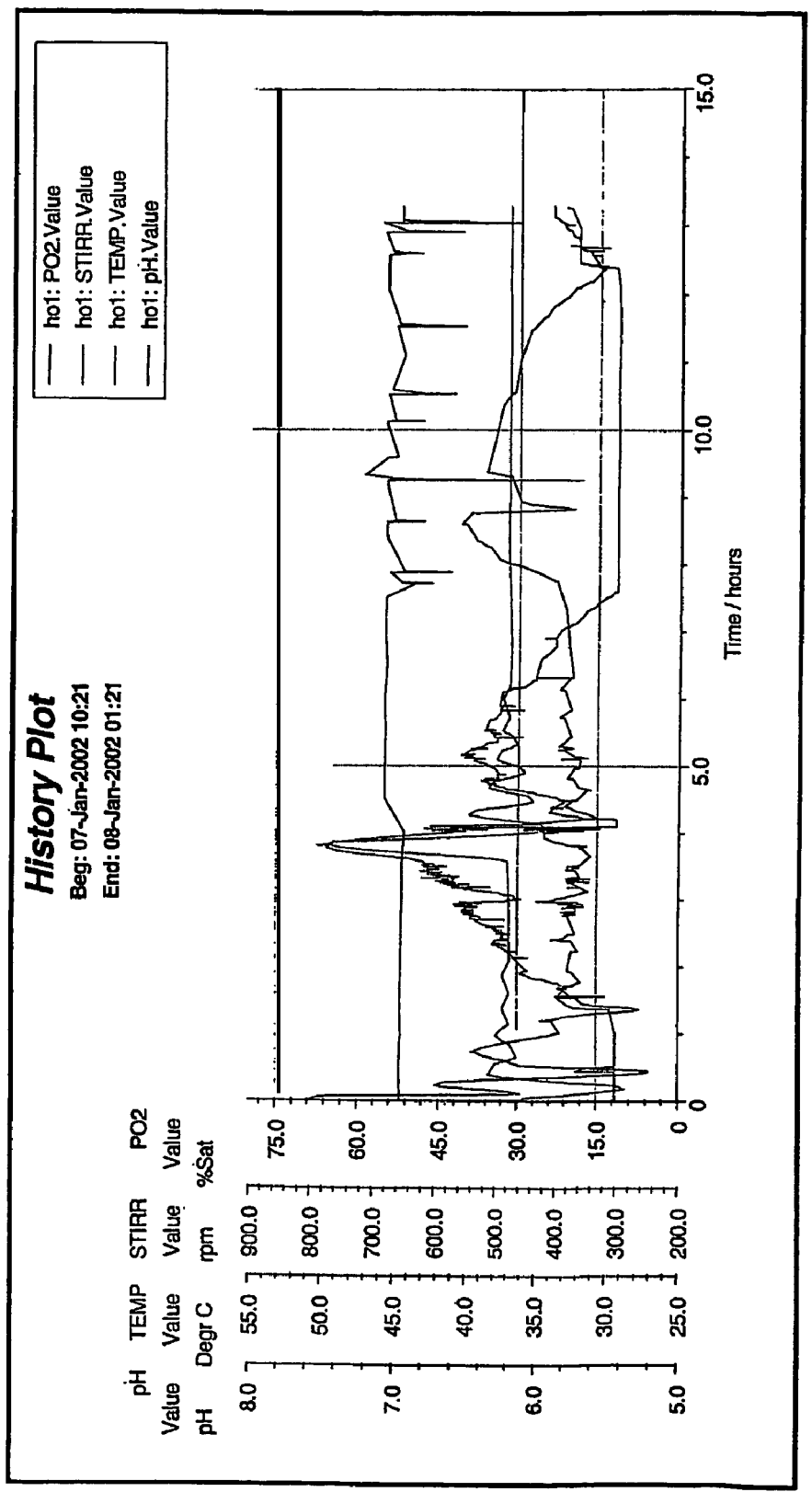
FIGS. 5A and 5B show history plots of the fermentation showing the changes of parameters such as temperature, stirring speed, pH and dissolved oxygen values.

The B. subtilis LLC101 strain is maintained on a Nutrient Agar (beef extract 1 g/L, peptone 10 g/L, NaCl 5 g/L and agar 20 g/L) plate, supplemented with 5 mg/L of chloramphenicol. To prepare the innoculum for batch and fed-batch fermentation, a few colonies of the aforementioned strain were transferred from a freshly prepared Nutrient Agar plate into two 1-L flasks, each containing 80 mL of fermentation medium containing glucose 5 g/L, tryptone 10 g/L, yeast extract 3 g/L, sodium citrate 1 g/L, $KH_2PO_4$ 1.5 g/L, $K_2HPO_4$ 1.5 g/L, and $(NH_4)_2SO_4$ 3 g/L. The bacterial cell culture was cultivated at 37° C. and pH 7.0 on an orbital shaker rotating at 250 r.p.m. The cultivation was terminated when $OD_{600nm}$ reached 5.5-6.0 at about 9-11 h growth time. Then the 160-nL culture broth was introduced into the 2-L fermentor containing 1440-mL fermentation medium (glucose 5 g/L, tryptone 10 g/L, yeast extract 3 g/L, sodium citrate 1 g/L, $KH_2PO_4$ 1.5 g/L, $K_2HPO_4$ 1.5 g/L, and $(NH_4)_2SO_4$ 3 g/L). The batch fermentation was carried out at a temperature of 37° C. The pH was controlled at 7.0 by adding sodium hydroxide and hydrochloric acid. The dissolved oxygen concentration was controlled at 20% air saturation with the adjustment of stirring speed. Heat shock was performed at 3.25 h when the culture density $(OD_{600nm})$ was about 3.9. During the heat shock, the temperature of the fermentor was increased from 37 degree C. to 50 degree C. and then cooled immediately to 37 degree C. The complete heating and cooling cycle took about 0.5 h. The OD of the culture reached a maximum of about 6.4 at 3.5 h after heat shock. Cells were harvested for separation and purification of Arginase at 6 h after heat shock. The aforementioned strain produced active human Arginase in an amount of about 30 mg/L of the fermentation medium at 6 h after heat shock. The time-course of the fermentation is plotted in FIG. 4A. The history plot of this batch fermentation showing the changes of parameters such as temperature, stirring speed, pH and dissolved oxygen values is depicted in FIG. 5A.

Example 2B

Fed-Batch Fermentation in a 2-Liter Fermentor

Figure 4B:
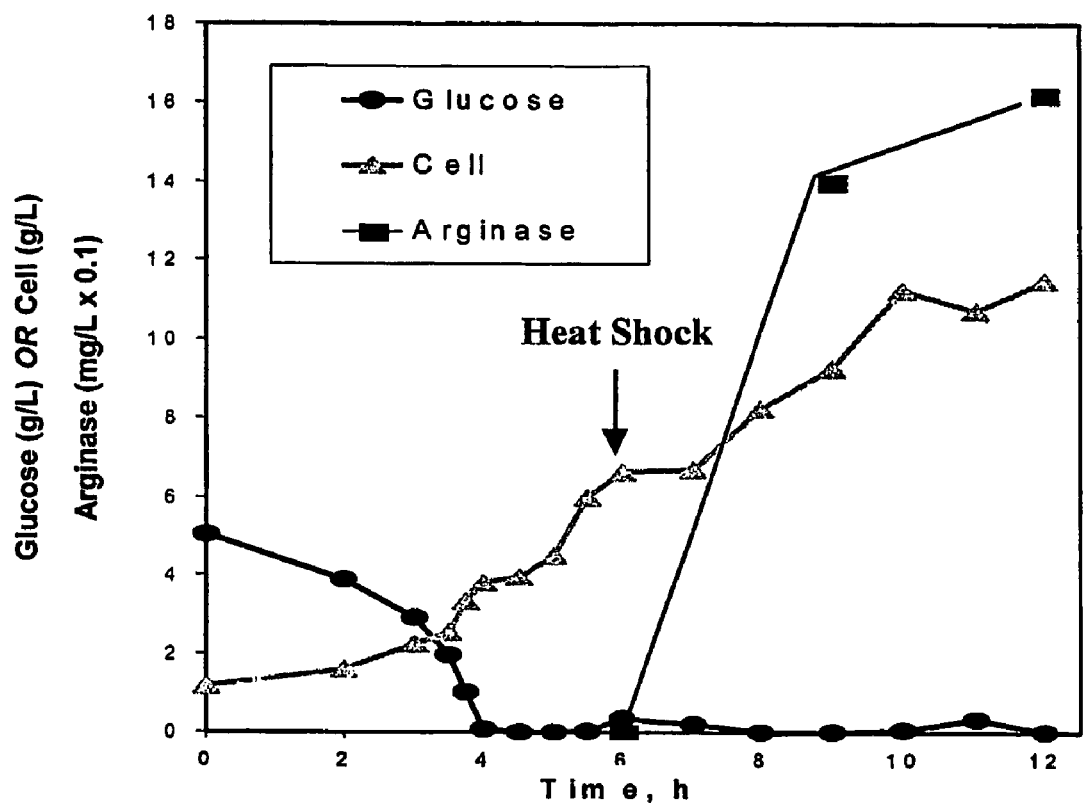
Figure 5B:
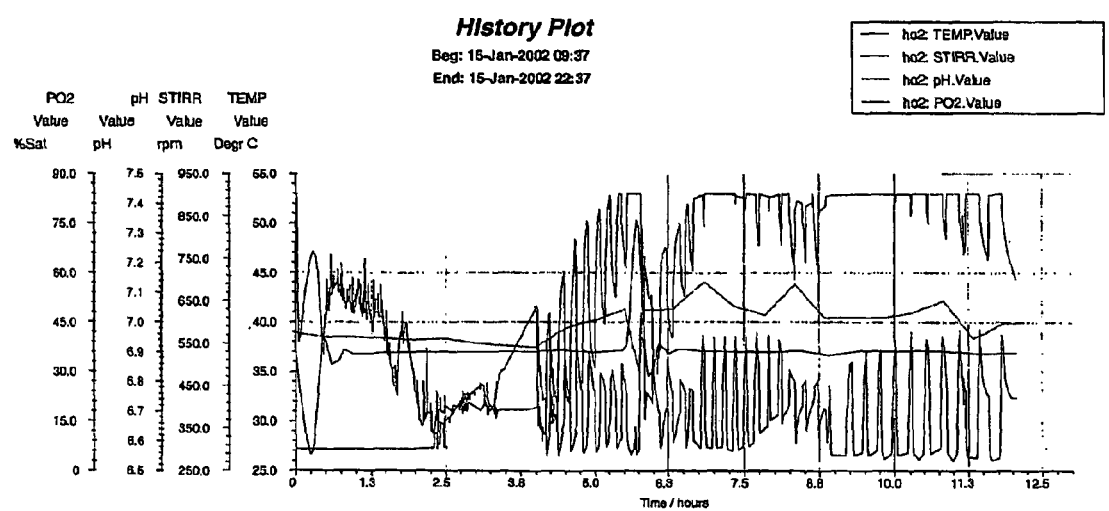

The Fed-batch fermentation was carried out at 37 degree C., pH 7.0 and dissolved oxygen 20% air saturation. The inoculation procedure was similar to that of the batch fermentation described in Example 2A. Initially, the growth medium was identical to that used in the batch fermentation described in Example 2A. The feeding medium contained 200 g/L glucose, 2.5 g/L $MgSO_4 \cdot 7H_2O$, 50 g/L tryptone, 7.5 g/L $K_2HPO_4$ and 3.75 g/L $KH_2PO_4$. The medium feeding rate was controlled with the pH-stat control strategy. In this strategy, the feeding rate was adjusted to compensate the pH increase caused by glucose depletion. This control strategy was first implemented when the glucose concentration decreased to a very low level at about 4.5-h fermentation time. If pH>7.1, 4 mL of feeding medium was introduced into the fermentor. Immediately after the addition of glucose, the pH value would decrease below 7.1 rapidly. After approximate 10 min, when the glucose added was completely consumed by the bacterial cells, the pH value would increase to a value greater than 7.1, indicating that another 4 mL of feeding medium was due to be added into the fermentor. Heat shock was performed at 5-6 h when the culture density $(OD_{600nm})$ was between 12.0 and 13.0. During the heat shock, the temperature of the fermentor was increased from 37 degree C. to 50 degree C. and then cooled immediately to 37 degree C. The complete heating and cooling cycle took about 0.5 h. Cells were harvested for separation and purification of Arginase at 3 h and 6 h after heat shock. The aforementioned strain produced active human Arginase in an amount of at least about 162 mg per L of the fermentation medium at 6 h after heat shock. The time-course of the fermentation is plotted in FIG. 4B. The history plot of this fed-batch fermentation showing the changes of parameters such as temperature, stirring speed, pH and dissolved oxygen values is indicated in FIG. 5B.

Example 2C

Fed-Batch Fermentation in a 100-Liter Fermentor

The Fed-batch fermentation was scaled up in a 100-L fermentor. The fermentation was carried out at 37 degree C., pH 7.0, dissolved oxygen 20% air saturation. A 10% inoculum was used. Initially, the growth medium was identical to that used in the batch fermentation described in Example 2A. The feeding medium contained 300 g/L glucose, 3.75 g/L $MgSO_4 \cdot 7H_2O$, 75 g/L tryptone, 11.25 g/L $K_2HPO_4$ and 5.625 g/L $KH_2PO_4$. The medium feeding rate was controlled with a pH-stat control strategy similar to that used in the fed-batch fermentation described in Example 2B. Heat shock was performed at about 7.5 h when the culture density $(OD_{600nm})$ was between 11.5 and 12.5. During the heat shock, the temperature of the fermentor was increased from 37 degree C. to 50 degree C., maintained at 50 degree C. for 7 s and then cooled immediately to 37 degree C. The complete heating and cooling cycle took about 0.5 h. Cells were harvested for separation and purification of Arginase at 2 h and 4 h after heat shock. The aforementioned strain produced active human Arginase in an amount of at least about 74 mg and 124 mg per L of the fermentation medium at 2 h and 4 h, respectively, after heat shock. These data show that harvesting cells 4 h after heat shock produced a higher Arginase yield than harvesting cells 2 h after heat shock in a 100-L fermentor.

Example 3

Comparison of Batch and Fed-Batch Fermentation

Table 1 below compares the results of batch and fed-batch fermentation. The comparison demonstrates that the fed-batch fermentation was much superior to the batch operation in terms of culture OD, Arginase yield and productivity.

TABLE 1

|  | Batch Fermentation | Fed-batch Fermentation |
|---|---|---|
| The OD at the start of heat shock | 3.9 | 12.8 |
| Maximum OD reached | 6.0 | 26.8 |
| Arginase Yield (mg/L) | 30 | 162 |
| Arginase Productivity (mg/L-h) | 2.5 | 13.5 |

Example 4

Purification of Arginase at 3H After Heat Shock After Fed-Batch Fermentation at Low Cell Density Fed-batch fermentation in a 2-liter fermentor was performed as described in Example 2B. The cell density of the fed-batch culture was monitored at 30 or 60 min interval and the temperature of the culture raised to 50° C. for heat shock at 5.5 hours after the fermentation started when the OD of the culture reached 12.8 (see FIG. 4B and FIG. 5B).

The cell culture (470 ml) collected at 3 h after heat shock was centrifuged at 5,000 rpm for 20 min at 4 degree C. to pellet the cells. The wet weight of the cells was 15.1 g. The culture supernatant liquor was discarded and the cell pellet was stored at −80 degree C. The cells are stable at this temperature for a few days. To extract intracellular proteins, the cell pellet was resuspended in 140 ml solubilization buffer [50 mM Tris-HCl (pH 7.4), 0.1 M NaCl, 5 mM MlSO$_4$, lysozyme (75 µg/ml)]. After incubation at 30 degree C. for 15 min, the mixture was sonicated for eight times, each time lasted for 10 s (the total time was 80 s), at 2 min intervals using the Soniprep 150 Apparatus (MSE). About 500 units of deoxyribonuclease I (Sigma D 4527) was added and the mixture was incubated at 37 degree C. for 10 min to digest the chromosomal DNA. After centrifugation at 10,000 rpm for 20 min at 4 degree C., the supernatant, containing the crude protein extract, was assayed for the presence of the Arginase activity and analyzed by SDS-PAGE (Laemmli, 1970, Nature, 227, 680-685).

Figure 6B:
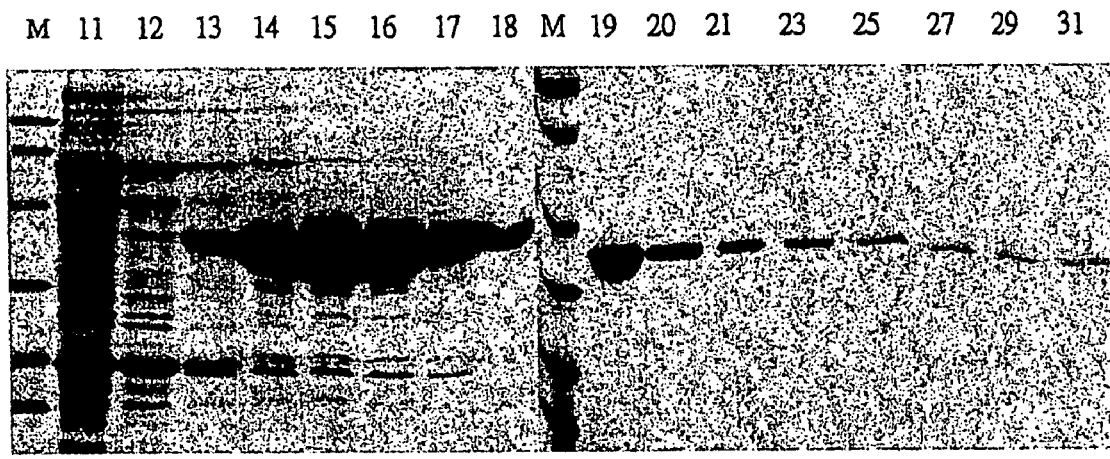
Figure 7B:
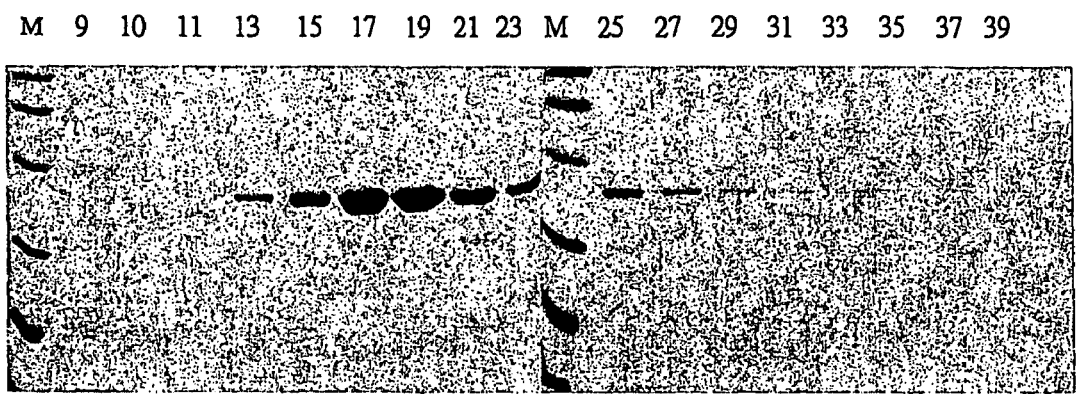

A 5-ml HiTrap Chelating column (Pharmacia) was equilibrated with 0.1 M NiCl$_2$ in dH$_2$O, for 5 column volumes. The crude protein extract (140 ml) was loaded onto the column. Elution was performed with a linear gradient (0-100%) at a flow rate of 5 ml/min for 15 column volumes under the following conditions: Buffer A=start buffer [0.02 M sodium phosphate buffer (pH 7.4), 0.5 M NaCl]; Buffer B=start buffer containing 0.5 M imidazole. The elution profile is shown in FIG. 6A and the protein gel is shown in FIG. 6B. Fractions 13-20 were pooled (16 ml) and diluted ten times with start buffer [0.02 M sodium phosphate buffer (pH 7.4), 0.5 M NaCl]. This was loaded onto a second 5-ml HiTrap Chelating column (Pharmacia), repeating the same procedure as above. The elution profile is shown in FIG. 7A and the protein gel is shown in FIG. 7B. Fractions 12-30 containing Arginase were pooled (38 ml) and salt was removed using a 50-ml HiPrep 26/10 desalting column (Pharmacia) with the following conditions: flow rate=10 mV/min, buffer=10 mM Tris-HCl (pH 7.4) and length of elution=1.5 column volume. The protein concentration was measured by the method of Bradford (Bradford, M. M., 1976, Anal. Biochem., 72, 248-254). A total of 56.32 mg of Arginase was purified from 470 ml cell culture. The yield of purified Arginase was estimated to be 119.8 mg/l cell culture or 3.73 mg/g wet cell weight.

Example 5

Purification of Arginase at 6H After Heat Shock After Fed-Batch Fermentation at Low Cell Density Fed-batch fermentation in a 2-liter fermentor was performed as described in Example 4. The cell culture (650 ml) collected at 6 h after heat shock at OD 12.8 was centrifuged at 5,000 rpm for 20 min at 4 degree C. to pellet the cells. The wet weight of the cells was 24 g. The culture supernatant liquor was discarded and the cell pellet was stored at −80° C. The cells are stable at this temperature for a few days. To extract intracellular proteins, the cell pellet was resuspended in 140 ml solubilization buffer [50 mM Tris-HCl (pH 7.4), 0.1 M NaCl, 5 mM MnSO$_4$, lysozyme (75 µg/ml)]. After incubation at 30 degree C. for 15 min, the mixture was sonicated for eight times, each time lasted for 10 s (the total time was 80 s), at 2 min intervals using the Soniprep 150 Apparatus (MSE). About 500 units of deoxyribonuclease I (Sigma D 4527) was added and the mixture was incubated at 37 degree C. for 10 min to digest the chromosomal DNA. After centrifugation at 10,000 rpm for 20 min at 4 degree C., the supernatant, containing the crude protein extract, was assayed for the presence of the Arginase activity and analyzed by SDS-PAGE (Laemmli, 1970, Nature, 227, 680-685).

Figure 8B:
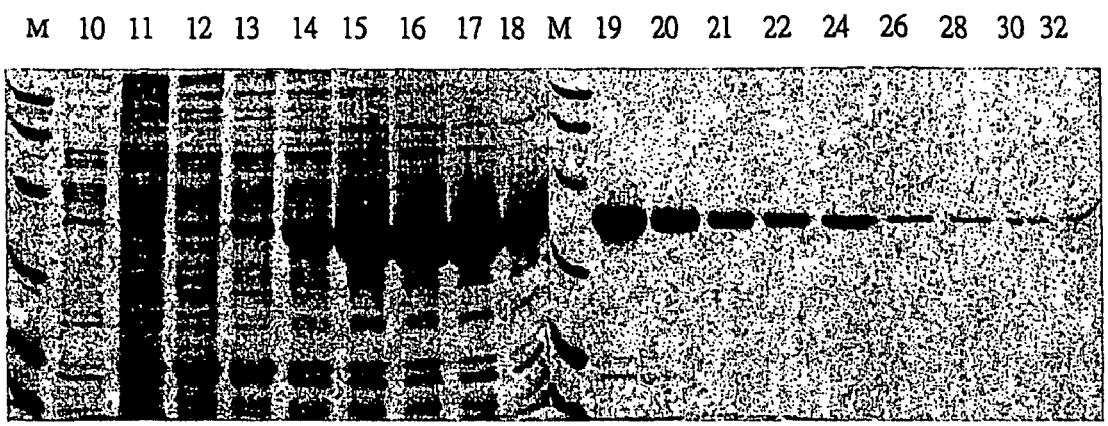
Figure 9B:
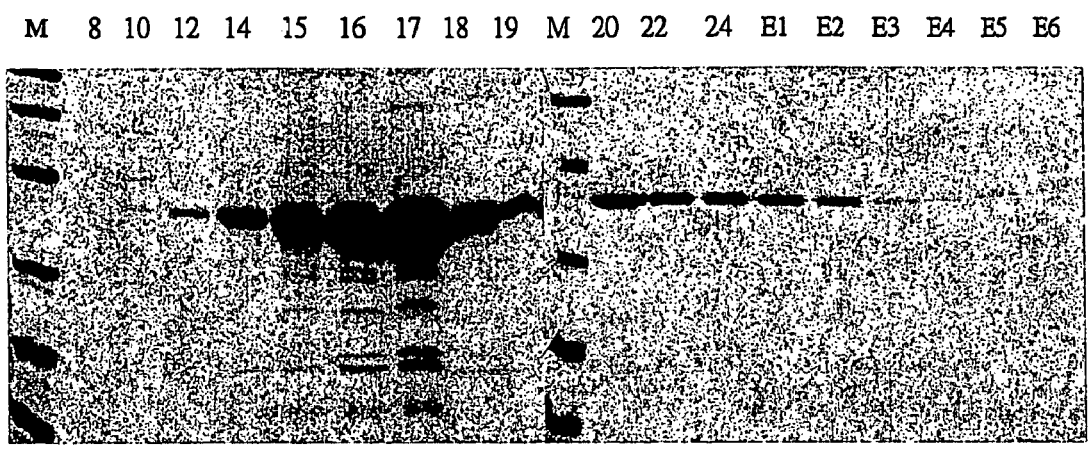

A 5-ml HiTrap Chelating column (Pharmacia) was equilibrated with 0.1 M NiCl$_2$ in dH$_2$O, for 5 column volumes. The crude protein extract (140 ml) was loaded onto the column. Elution was performed with a linear gradient (0-100%) at a flow rate of 5 m/min for 15 column volumes under the following conditions: Buffer A=start buffer [0.02 M sodium phosphate buffer (pH 7.4), 0.5 M NaCl]; Buffer B=start buffer containing 0.5 M imidazole. The elution profile is shown in FIG. 8A and the protein gel is shown in FIG. 8B. Fractions 13-24 were pooled (24 ml) and diluted ten times with start buffer [0.02 M sodium phosphate buffer (pH 7.4), 0.5 M NaCl]. This was loaded onto a second 5-ml HiTrap Chelating column (Phalmacia), repeating the same procedure as above. The elution profile is shown in FIG. 9A and the protein gel is shown in FIG. 9B. Fractions 12-24 containing Arginase were pooled (26 ml) and salt was removed using a 50-ml HiPrep 26/10 desalting column (Pharmacia) with the following conditions: flow rate=10 ml/min, buffer=10 mM Tris-HCl (pH 7.4) and length of elution=1.5 column volume. The protein concentration was measured by the method of Bradford (Bradford, M. M., 1976, Anal. Biochem., 72, 248-254). A total of 85.73 mg of Arginase was purified from 650 ml cell culture. The yield of purified Arginase was estimated to be 132 mg/l cell culture or 3.57 mg/g wet cell weight Example 6

Purification of Arginase at 6H After Heat Shock at a Higher Cell Density

Figure 10:
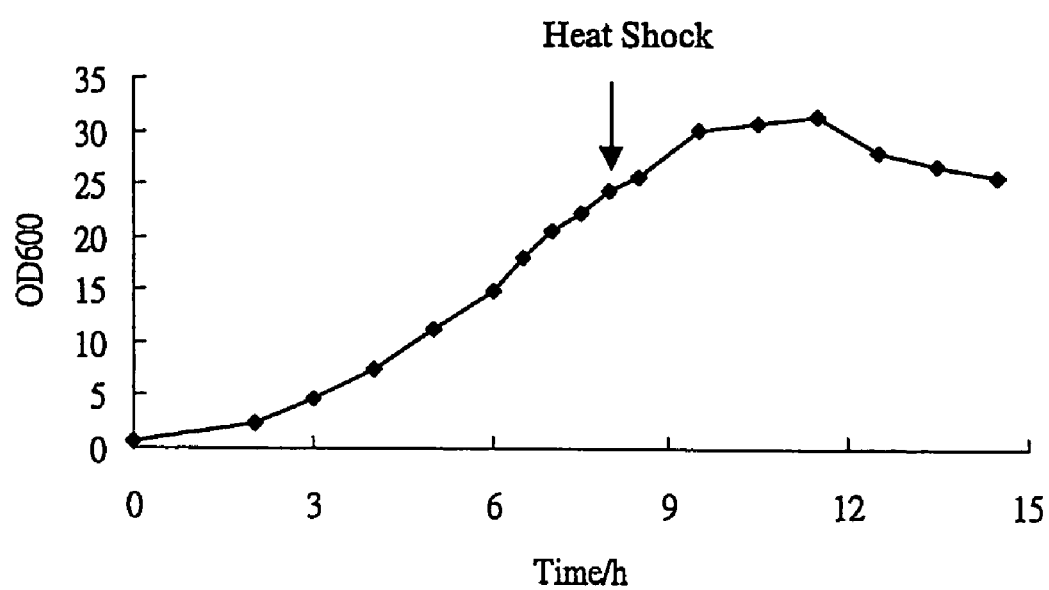
FIG. 10 shows the time-course of bacterial cell growth when heat shock was performed at a higher cell density. Heat shock was performed at 8 h when the culture density ($OD_{600nm}$) was about 25.
Figure 11:
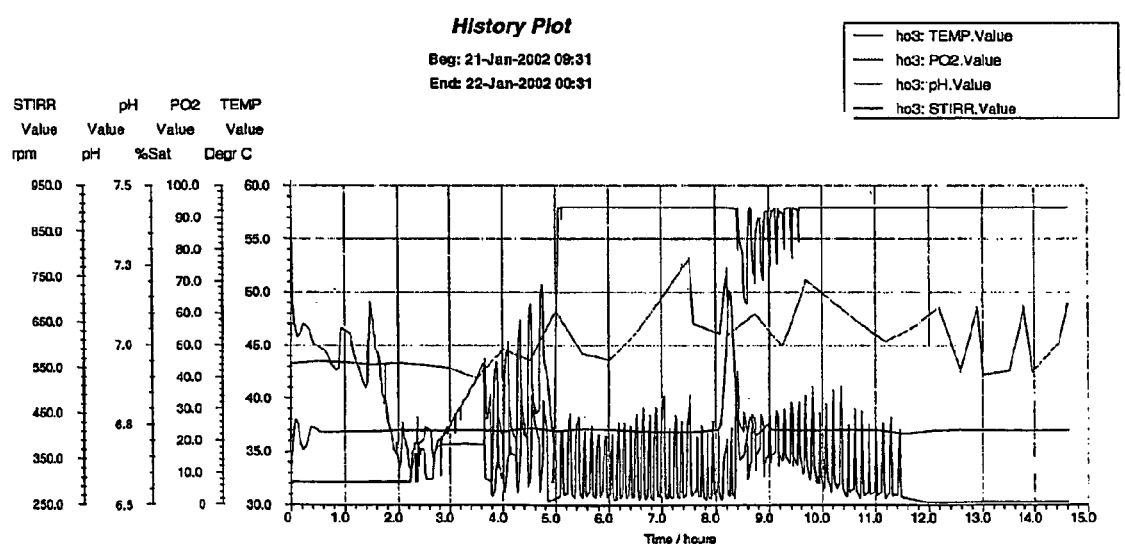
FIG. 11 is the history plot of the fed-batch fermentation when heat shock was performed at a higher cell density. This plot shows the changes of parameters such as temperature, stiring speed, pH and dissolved oxygen values.

In this particular fed-batch fermentation, the process was similar to the above example except that the heat shock was performed at 8 h when the culture density (OD$_{600nm}$) was about 25. During the heat shock, the temperature of the fermentor was increased from 37 degree C. to 50 degree C. and then cooled immediately to 37 degree C. The complete heating and cooling cycle took about 0.5 h. A portion of the cell culture (760 ml) was harvested for separation and purification of Arginase at 6 h after heat shock. The time-course of bacterial cell growth in this fermentation is plotted in FIG. 10. The history plot of this fed-batch fermentation showing the changes of parameters such as temperature, stirring speed, pH and dissolved oxygen values is indicated in FIG. 11.

The cell culture (760 ml) collected at 6 h after heat shock was centrifuged at 5,000 rpm for 20 min at 4 degree C. to pellet the cells. The wet weight of the cells was 32 g. The culture supernatant liquor was discarded and the cell pellet was stored at −80 degree C. The cells are stable at this temperature for a few days. To extract intracellular proteins, the cell pellet was resuspended in 280 ml solubilization buffer [50 mM Tris-HCl (pH 7.4), 0.1 M NaCl, 5 mM MnSO$_4$, lysozyme (75 µg/ml)]. After incubation at 30 degree C. for 15 min, the mixture was sonicated for eight times, each time lasted for 10 s (the total time was 80 s), at 2 min intervals using the Soniprep 150 Apparatus (MSE). About 500 units of deoxyribonuclease I (Sigma D 4527) was added and the mixture was incubated at 37 degree C. for 10 min to digest the chromosomal DNA. After centrifugation at 10,000 rpm for 20 min at 4 degree C., the supernatant, containing the crude protein extract, was assayed for the presence of the Arginase activity and analyzed by SDS-PAGE (Laemmli, 1970, Nature, 227, 680-685).

Figure 12B:
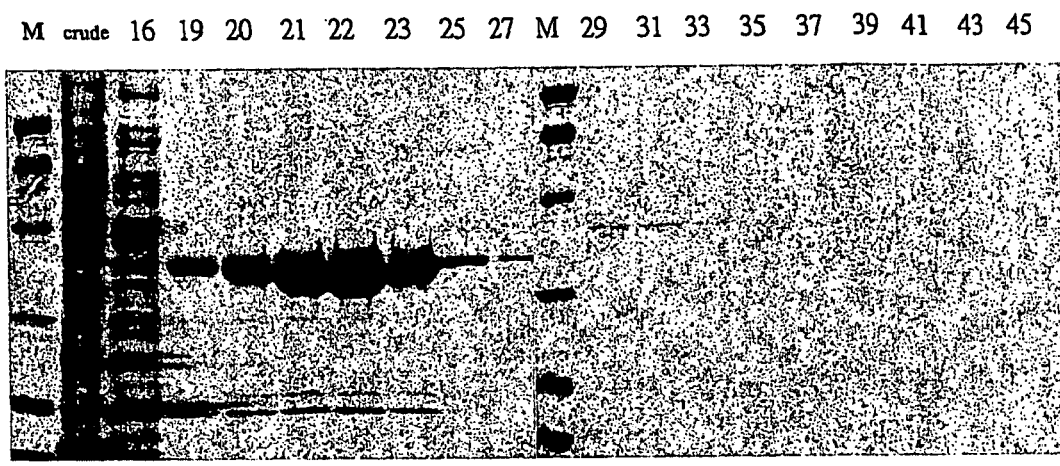
Figure 13B:
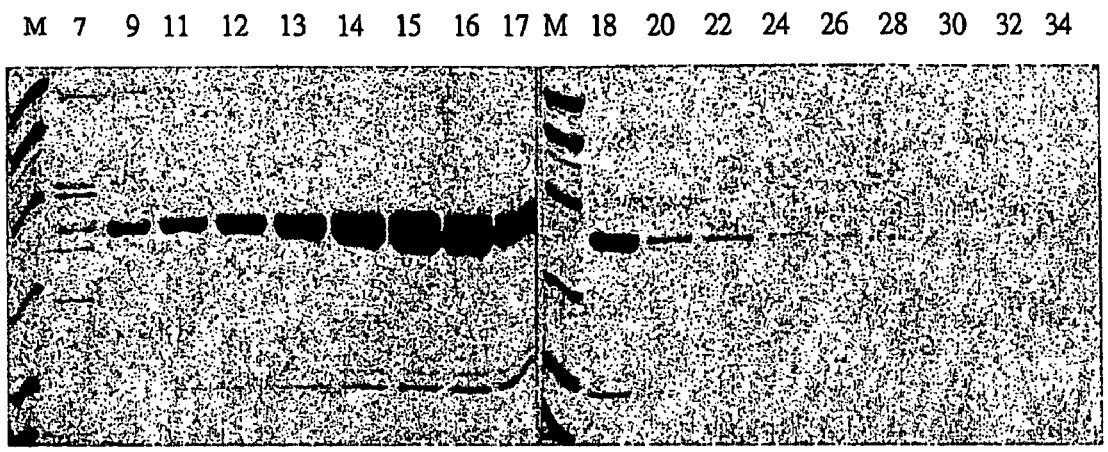
Figure 14B:
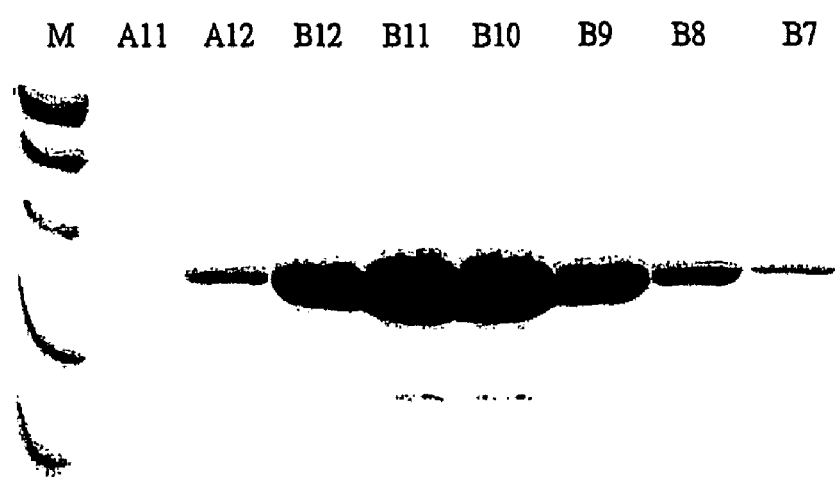
Figure 15B:
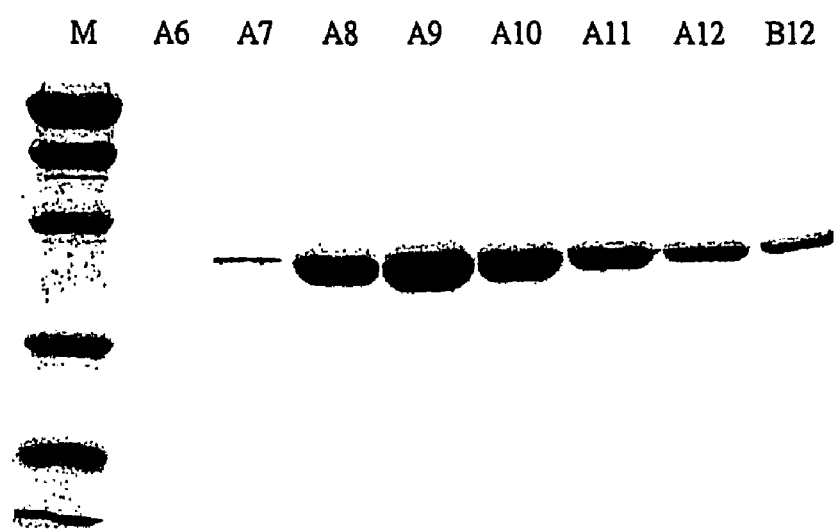

A 5-ml HiTrap Chelating column (Pharmacia) was equilibrated with 0.1 M NiCl$_2$ in dH$_2$O, for 5 column volumes. The crude protein extract (280 ml) was loaded onto the column. Elution was performed with a linear gradient (0-100%) at a flow rate of 5 ml/min for 15 column volumes under the following conditions: Buffer A=start buffer [0.02 M sodium phosphate buffer (pH 7.4), 0.5 M NaCl]; Buffer B=start buffer containing 0.5 M imidazole. The elution profile is shown in FIG. 12A and the protein gel is shown in FIG. 12B. Fractions 17-31 were pooled (30 ml) and diluted ten times with start buffer [0.02 M sodium phosphate buffer (pH 7.4), 0.5 M NaCl]. This was loaded onto a second 5-ml HiTrap Chelating column (Pharmacia), repeating the same procedure as above. The elution profile is shown in FIG. 13A and the protein gel is shown in FIG. 13B. Fractions 10-20 containing Arginase were pooled (22 ml) and salt was removed using a 50-ml HiPrep 26/10 desalting column (Pharmacia) with the following conditions: flow rate=10 ml/min, buffer=10 mM Tris-HCl (pH 7.4) and length of elution=1.5 column volume. The sample was then loaded onto a 1-ml HiTrap SP FF column (Pharmacia). Elution was performed with the following conditions: flow rate=1 ml/min, Buffer A=10 mM Tris-HCl (pH 7.4), Buffer B=10 mM Tris-HCl (pH 7.4) containing 1 M NaCl, linear gradient (0-100%), length of elution=30 column volumes. The elution profile is shown in FIG. 14A and the protein gel is shown in FIG. 14B. Fractions A12-B7 were pooled (7 ml) and diluted ten times with start buffer [0.02 M sodium phosphate buffer (pH 7.4), 0.5 M NaCl]. This sample was loaded onto a second 1-ml HiTrap SP FF column (Pharmacia), repeating the same procedure as above, except that the elution was performed with a segmented gradient. The elution profile is shown in FIG. 15A and the protein gel is shown in FIG. 15B. Fractions A7-B12 were pooled (7 ml) and desalted as above using a 50-ml HiPrep 26/10 desalting column (Pharmacia). The protein concentration was measured by the method of Bradford (Bradford, M. M., 1976, Anal. Biochem., 72, 248-254). A total of 41.61 mg of Arginase was purified from 760 ml cell culture. The yield of purified Arginase was estimated to be 55.5 mg/l cell culture or 1.3 mg/g wet cell weight.

Example 7

Comparison of Yield of Arginase Harvested and Purified Under Various Conditions

Table 2 below compares the yield of the Arginase produced under various harvesting and purification conditions. These data show that harvesting cells 6 h after heat shock at a lower cell density of 12.8 produced a higher Arginase yield of 132 mg/L after purification.

TABLE 2

| Fed-batch Fermentation | Arginase Yield (mg/L) | |
| --- | --- | --- |
|  | Harvested 3 h after heat shock | Harvested 6 h after heat shock |
| Heat shock at OD 12.8 | 120 | 132 |
| Heat shock at OD 25 | — | 55.5 |

Example 8A

Preparation of the Pegylated Enzyme Using Cyanuric Chloride (CC) Activated Methoxypolyethylene Glycol 50 mg Arginase was dissolved in 20 ml PBS buffer solution (pH 7.4) to a final concentration of 2.5 mg/ml. Heat activation of Arginase was carried out at 60° C. for 10 minutes. After activation, the temperature of the enzyme was allowed to bring back to room temperature. 1 g cyanuric chloride activated methoxypolyethylene glycol (mPEG-CC) (MW=5000, Sigma) was added to Arginase at mole ratio 1:140 (Arginase: PEG). A magnetic stirring bar was used to stir the mixture until all of the polyethylene glycol (PEG) was dissolved.

When all of the PEG was dissolved, pH of the PEG-Arginase mixture was adjusted to 9.0 with 0.1 N NaOH, pH was further maintained at 9.0 for the next 30 minutes with furter additions of NaOH. Pegylation was stopped by adjusting pH back to 7.2 with addition of 0.1 N HCl.

The pegylated Arginase was dialyzed against 2-3 liters of PBS buffer solution, pH 7.4, at 4° C., with the use of a Hemoflow F40S capillary dialyzer (Fresenius Medical Care, Germany) to remove excess PEG. After dialysis, pegylated Arginase was recovered and the final concentration was readjusted.

The pegylated Arginase was filtered through a 0.2 pmn filter into a sterilized container and was stored at 4° C. The ½-life of this enzyme in a human patient was tested to be about 6 hours (see FIG. 21).

Example 8B

Preparation of Arginase Expressed in *B. subtilis* and Using Either CC or SPA at a Lower Peg Ratio Pegylation was first developed by Davis, Abuchowski and colleagues (Davis, F. F. et al., 1978, Enzyme Eng. 4, 169-173) in the 1970s. In contrast to modifying the formulation of a drug, chemical attachment of poly(ethylene glycol) PEG moieties to therapeutic proteins (a process known as "pegylation") represents a new approach that may enhance important drug properties (Harris, J. M. et al., 2001, Clin. Pharmacokinet. 40, 539-551).

In 1979, Savoca et al. attached methoxypolyethylene glycol (mPEG) of 5,000 Daltons covalently to bovine liver Arginase using 2,4,6-trichloro-s-triazine (cyanuric chloride) as the coupling agent (Savoca, K. V. et al., 1979, Biochimica et Biophysica Acta 578, 47-53). The conjugate (PEG-Arginase) only retained 65% of its original enzymatic activity. They reported that the blood-circulating life of PEG-Arginase in mice was extended over that of bovine Arginase. The half-life of injected bovine Arginase was less than 1 h, whereas that of the PEG-enzyme was 12 h. Their data also indicated that bovine Arginase modified by PEG was rendered both non-immunogenic and non-antigenic when tested in mice.

Recombinant human Arginase (1.068 mg) was dissolved in 125 mM borate buffer solution (pH 8.3) on ice or at room temperature. Activated mPEG, succinimide of mPEG propionic acid (mPEG-SPA; MW 5,000; Shearwater Corporation) or mPEG activated with cyanuric chloride (mPEG-CC; MW 5,000; Sigma), was added into the solution at Arginase:PEG mole ratios of 1:50 or 1:20. This was performed in two stages. At the first stage, half of the PEG was added into the Arginase solution little by little and mixed for 30 min gently on ice to prevent the pH getting out of the recommended range of 8.0-8.5. The other half of the PEG was added to this solution and further mixed gently for 0.5-23 h. The mixture was then dialyzed against $dH_2O$ by changing with $dH_2O$ at least 3 times at 4 degree C. using dialysis membrane with cut-off value of below 10,000. Both MnPEG-SPA and mPEG-CC use amino groups of lysines and the N-terminus of the protein as the site of modification.

Figure 16A:
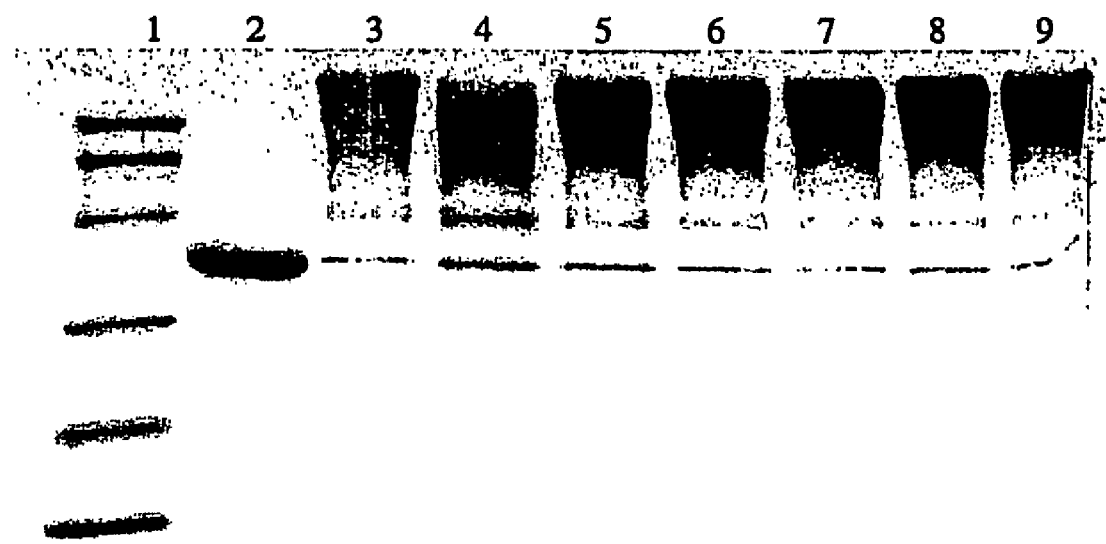
FIGS. 16A and 16B are the SDS-PAGE (15%) analysis of the human Arginase modified with MnPEG-SPA (MW 5,000) using the Arginase:PEG mole ratio of 1:50.
Figure 16B:
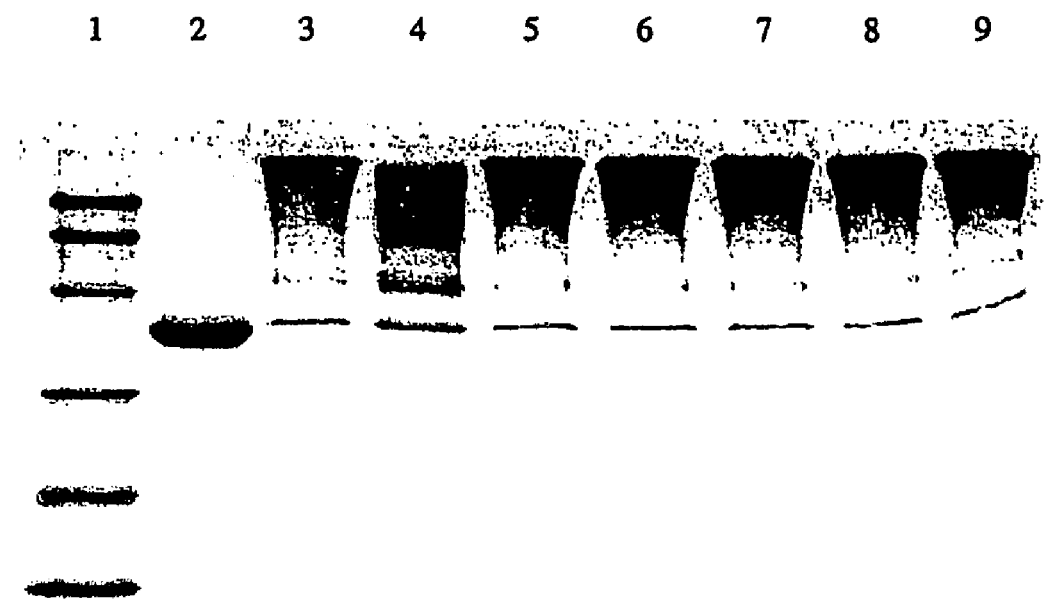
Figure 17A:
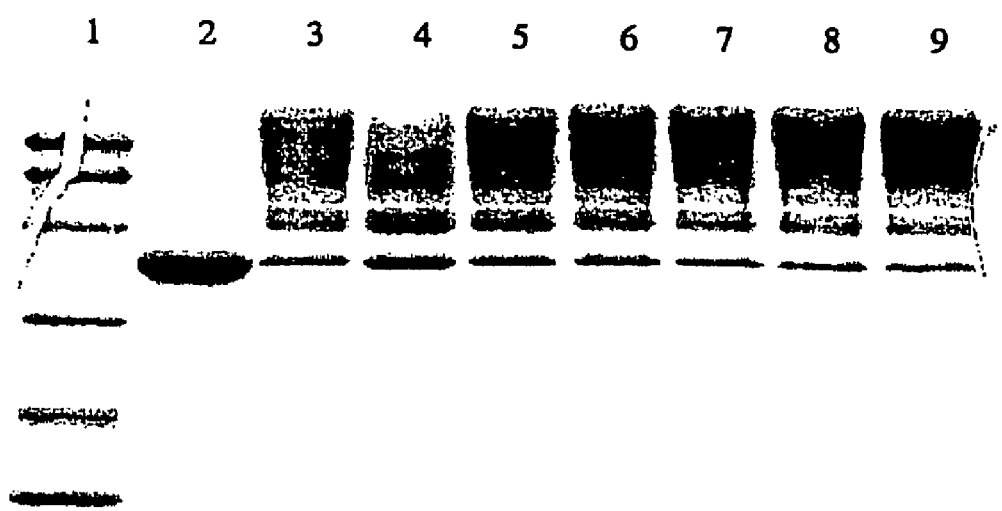
FIGS. 17A and 17B are the SDS-PAGE (15%) analysis of the human Arginase modified with mPEG-SPA (MW 5,000) using the Arginase:PEG mole ratio of 1:20.
Figure 17B:
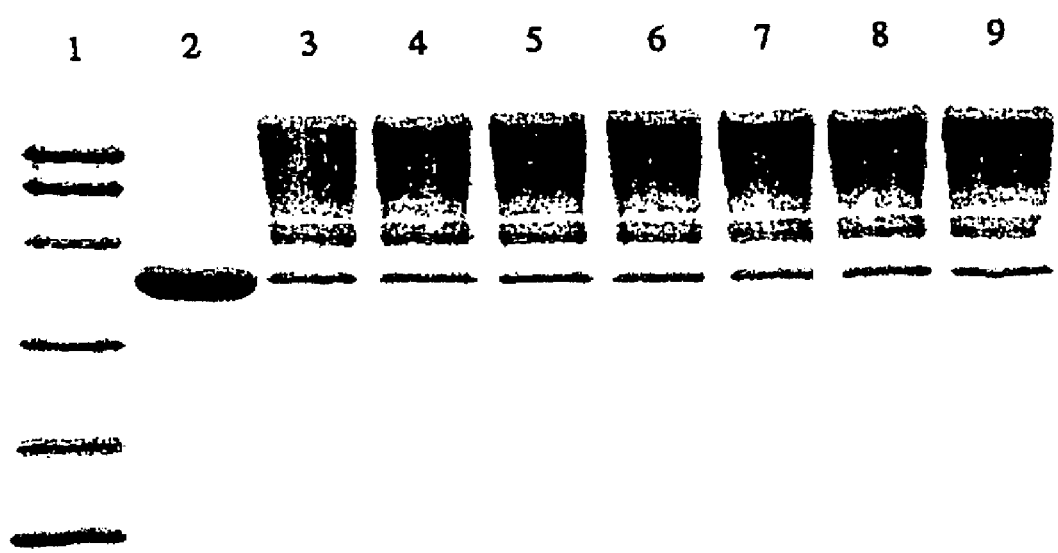

When Arginase was modified on ice or at room temperature with MPEG-SPA (MW 5,000) using an Arginase:PEG mole ratio of 1:50, most of the enzyme molecules were modified after 1 h of reaction (FIG. 16). The sample appeared the same even after 23 h of reaction. Arginase molecules were attached with different numbers of PEG molecules and generated molecules of various molecular weights. As expected, when a lower mole ratio of 1:20 was used for the pegylation reaction, a higher proportion of Arginase was found in the non-pegylated form (FIG. 17). However, for both of the mole ratios of Arginase:PEG used, longer reaction time and the use of room temperature instead of ice did not seem to affect the extent of pegylation. With MPEG-SPA (MW 5,000), a mole ratio of 1:50 and 1 h of reaction, the Arginase retained as much as 72-76% of its original enzymatic activity (see Table 3 below), which is higher than that reported for the bovine Arginase (65%; Savoca, K. V. et al., 1979, Biochimica et Biophysica Acta 578, 47-53).

Figure 18A:
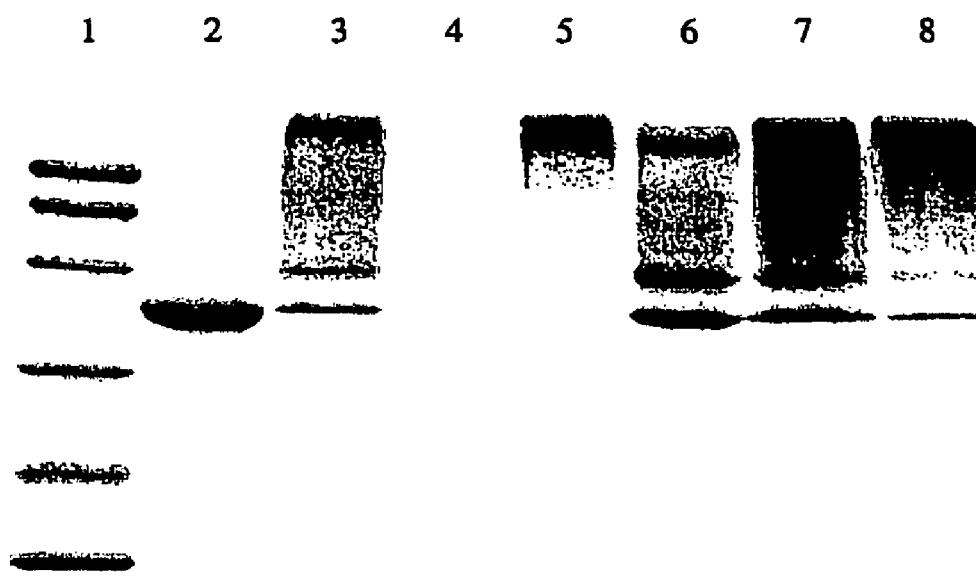
FIG. 18A is the SDS-PAGE (15%) analysis of the human Arginase modified with mPEG-CC (MW 5,000). The reactions were performed on ice. Lane 1: low-range protein marker; Lane 2: Arginase (5.35 µg) without PEG added (control); Lane 3: 2 h after reaction with Arginase:PEG mole ratio of 1:50; Lane 4: empty; Lane 5: 23 h after reaction with Arginase:PEG mole ratio of 1:50; Lane 6: 2 h after reaction with Arginase:PEG mole ratio of 1:20; Lane 7: 5 h after reaction with Arginase:PEG mole ratio of 1:20; Lane 8: 23 h after reaction with Arginase:PEG mole ratio of 1:20.

When Arginase was modified on ice with mPEG-CC (MW 5,000) using an Arginase:PEG mole ratio of 1:50, the reaction was quite slow and it took 23 h to complete the pegylation (FIG. 18A). Moreover, most of the enzyme molecules were converted to a narrow spectrum of very high molecular weights. The reaction was much slower if a lower mole ratio of 1:20 was used, as indicated in FIG. 18A.

Example 8C

Preparation of Highly Active Pegylated Arginase

Fed-batch fermentation in a 15-L B. Braun Biostat C stainless steel fermentor was performed as described in Example 4. The cell culture (8.4 L) collected at 4.5 h after heat shock at OD 12-13 was centrifuged at 5,000 rpm for 20 min at 4 degree C. to pellet the cells. The culture supernatant liquor was discarded and the cell pellet was stored at −80° C. The cells are stable at this temperature for a few days. To extract intracellular proteins, the cell pellet was resuspended in 1250 ml solubilization buffer [50 mM Tris-HCl (pH 7.4), 0.1 M NaCl, 5 mM $MnSO_4$, lysozyme (75 µg/ml)]. After incubation at 30 degree C. for 20 min, the mixture was divided into 300-ml portions in beakers, and each portion was sonicated for 12 times, each time lasted for 10 s (the total time was 120 s), at 2 min intervals using the Soniprep 150 Apparatus (MSE). About 5000 units of deoxyribonuclease I (Sigma D 4527) was added and the mixture was incubated at 37 degree C. for 15 min to digest the chromosomal DNA. After centrifugation twice, each at 9,000 rpm for 30 min at 4 degree C., the supernatant, containing the crude protein extract, was assayed for the presence of the Arginase activity and analyzed by SDS-PAGE (Laemmli, 1970, Nature, 227, 680-685).

The crude protein extract (1195 ml) was filtered and divided into 2 portions, each contained 597.5 ml. Each portion was then loaded onto a 130-ml Ni-NTA superflow (Qiagen) column (Pharmacia). Elution was performed with a linear gradient (0-100%) at a flow rate of 5 ml/min under the following conditions: Buffer A=start buffer [0.02 M sodium phosphate buffer (pH 7.4), 0.5 M NaCd]; Buffer B=start buffer containing 0.5 M imidazole. Fractions containing pure Arginase were pooled and buffer exchanged at 35 ml/min at 4 degree C. with PBS buffer, pH 7.4 using the Pellicon XL device (polyether-sulphone membrane cut-off=8 kDa) and the lab-scale tangential flow filtration system (Millipore). The protein concentration was measured by the method of Bradford (Bradford, M. M., 1976, Anal. Biochem., 72, 248-254). A total of 788 mg of Arginase was purified from 8.4 L cell culture. The yield of purified Arginase was estimated to be 94 mg/l cell culture. The measured specific activity was as high as 518 I.U./mg.

Figure 18B:
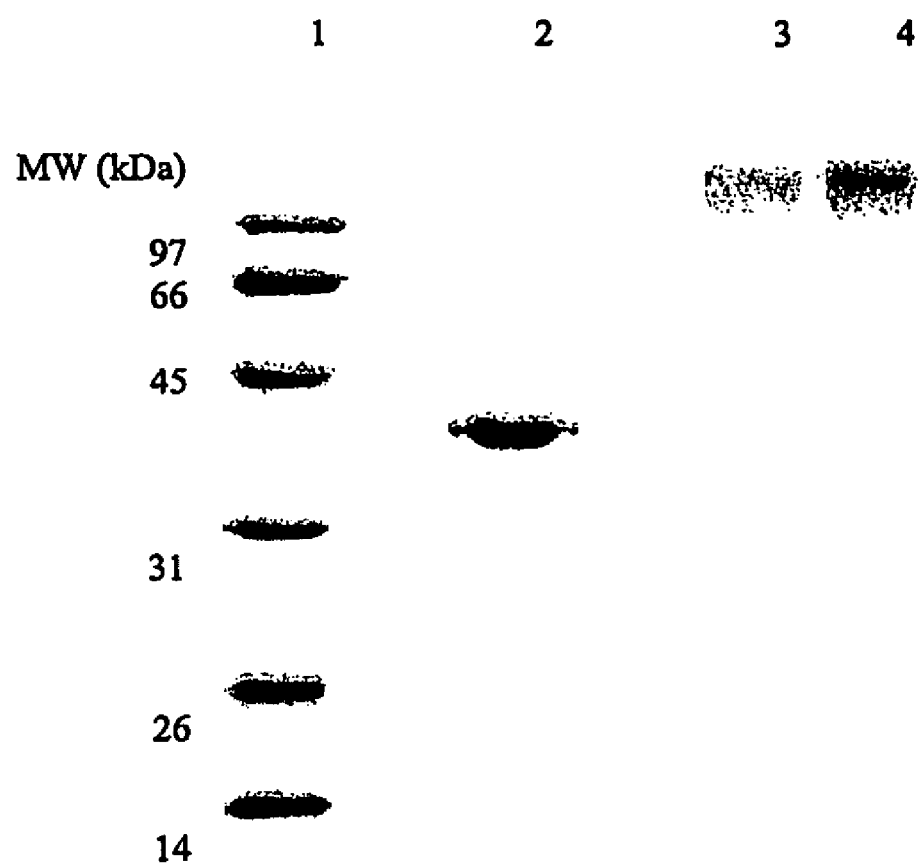
FIG. 18B shows the SDS-PAGE (12%) analysis of the native and the pegylated Arginase which are highly active and stable. Lane 1: Low-range protein marker (Dio-rad); Lane 2: Native Arginase (1 µg); Lane 3: Pegylated Arginase (1 µg); Lane 4: Pegylated Arginase after ultra-dialysis (1.5 µg).

Pegylated Arginase with high specific activity was prepared in PBS buffer. The purified Arginase (specific activity=518 I.U./mg) was in PBS buffer before carrying out pegylation. The mPEG-SPA, MW 5,000 (5.82 g) was added into 555 ml of the purified Arginase (813.64 mg, 1.466 mg/ml) solution slowly in a 1-L beaker and then stirred for 2 h 40 min at room temperature (mole ratio of Arginase: mPEG-SPA=1:50). The mixture was then dialyzed extensively by ultradialysis against 15 L of PBS buffer using the F50(S) capillary dialyser (Fresenius Medical Care) to remove all the unincorporated PEG. The mPEG-SPA uses amino groups of lysines and the N-terminus of the protein as the site of modification. The measured specific activity of the pegylated Arginase is as high as 592 I.U./mg. The results from SDS-PAGE analysis of the native and the pegylated Arginase are shown in FIG. 18B. The pegylated Arginase was shown to be highly stable, in terms of Arginase activity and protein concentration, when stored in PBS buffer at 1 mg/ml for at least 3 weeks at room temperature. When stored at 4 degree C. in PBS buffer at 1 mg/ml, it is stable for at least 6 months without decrease in specific activity.

TABLE 3

Activity (%) of Arginase when pegylated with various activated PEG at different mole ratios and temperatures.

| Time (h) Allowed for the Pegylation Reaction | Activity (%) of Arginase (pegylated at room temperature with Arginase:mPEG-SPA ratio of 1:20) | Activity (%) of Arginase (pegylated on ice with Arginase:mPEG-SPA ratio of 1:20) | Activity (%) of Arginase (pegylated at room temperature with Arginase:mPEG-SPA ratio of 1:50) | Activity (%) of Arginase (pegylated on ice with Arginase:mPEG-SPA ratio of 1:50) | Activity (%) of Arginase (pegylated on ice with Arginase:mPEG-CC ratio of 1:20) | Activity (%) of Arginase (pegylated on ice with Arginase:mPEG-CC ratio of 1:50) |
|---|---|---|---|---|---|---|
| 0 | 100 | 100 | 100 | 100 | 100 | 100 |
| 1 | 83 | 76 | 76 | 72 | ND | ND |
| 2 | 79 | 76 | 72 | 68 | 68 | 64 |
| 5 | 83 | 74 | 74 | 72 | 65 | 65 |
| 23 | 75 | 72 | 72 | 64 | 66 | 66 |

ND: Not determined.
100% activity of Arginase is equivalent to 336 I.U./mg of protein.

Example 9A

½-Life Determination In Vivo of Arginase Obtained from Example 8A

Figure 21:
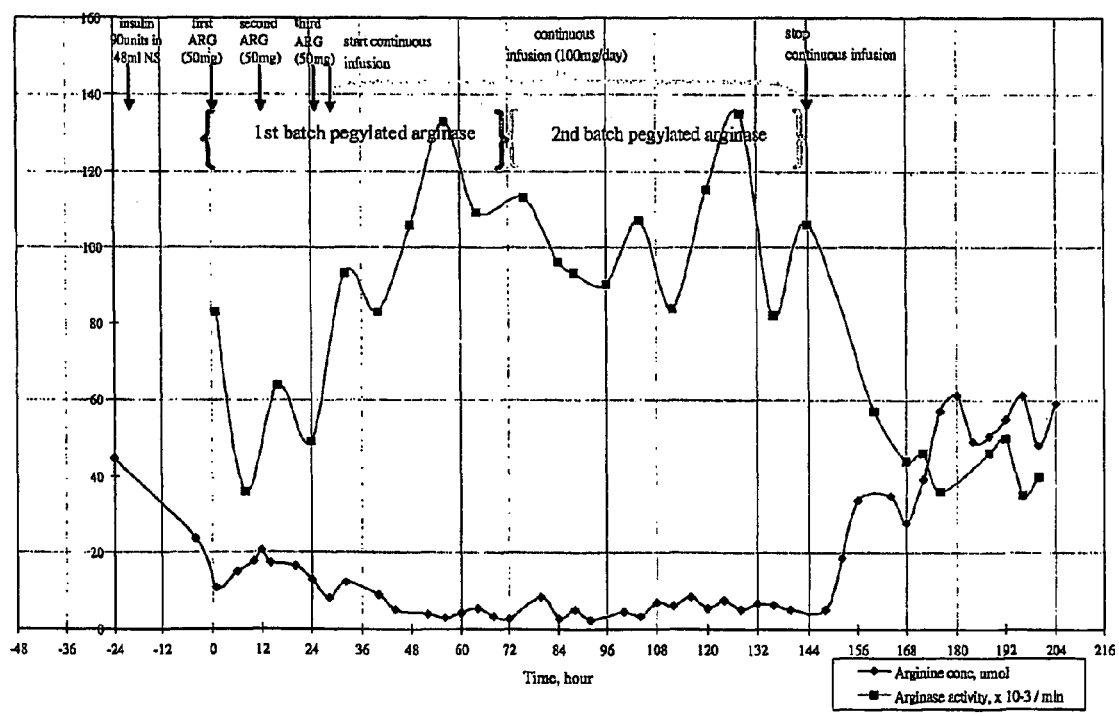
FIGS. 21 and 22 show the half-life determination in vivo of pegylated Arginase obtained from the method described in example 8A.

The pegylated Arginase was injected into a patient. A 3 ml blood sample in EDTA was taken from patient on a daily basis. The tube was pre-cooled to 4° C. on melting ice to prevent ex-vivo enzymatic reaction. The blood was then immediately spun down at 14000 rpm for 2 minutes to remove red blood cells. 1.5 ml supernatant (plasma) was pipetted out and transferred to a new eppendorf tube. The plasma was then incubated at 37° C. for 30 minutes. After incubation, arginine was added as a substrate in concentration of 100 μM. Enzyme reaction was carried out at 37° C. for 0, 10, 30, 60 minutes. At each time interval, reaction was stopped by taking out 300 μl reaction sample to a new eppendorf tube containing 300 μl 10% trichloroacetic acid. Samples were taken and spun at maximum speed (14000 rpm) for 10 minutes. Supernatant was pipetted out and filtered with 0.45 μm filter. Finally, samples at different time intervals were analysed with amino acid analyzer (Hitachi, L8800). The results are shown in FIG. 21.

Two batches of pegylated Arginase were prepared as described in Example 8A during the studies. The first batch of pegylated Arginase was prepared with Arginase:PEG mole ratio of 1:140. The second batch of pegylated Arginase was prepared with Arginase:PEG mole ratio of 1:70. The pegylation protocol and condition used for preparing the two batches were identical (see Example 8A).

At time zero, 50 mg of the first batch of pegylated Arginase was infused. After 12 hours, another 50 mg of the first batch of pegylated Arginase was infused. The third Arginase infusion was done at hour 24 during which another 50 mg of the first batch of pegylated Arginase was used.

Figure 22:
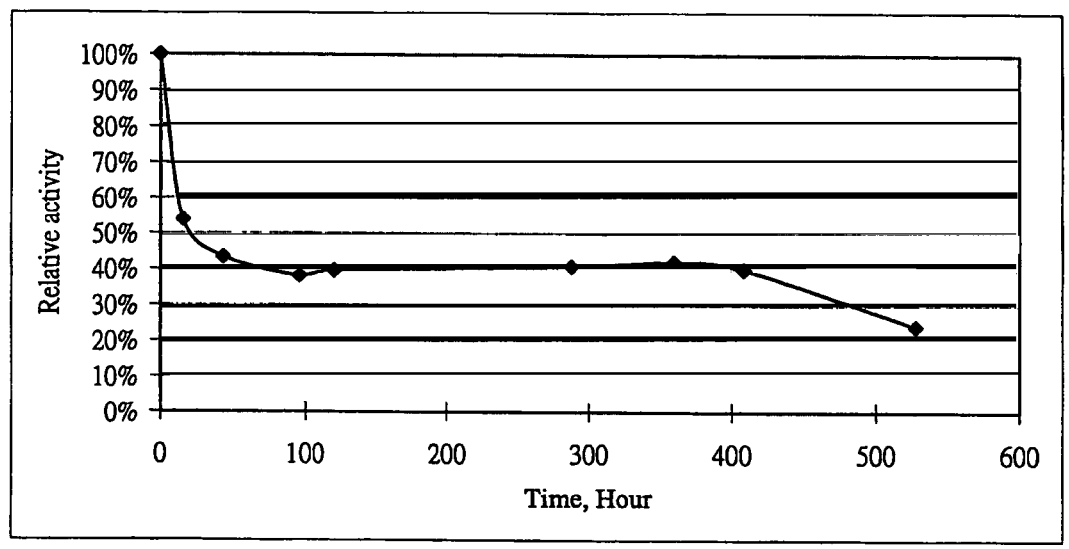

From hour 26 to hour 72, continuous infusion of the first batch of pegylated Arginase (100 mg/day) was carried out instead of intermittent infusion (50 mg/dosage). From hour 72 to hour 144, continuous infusion of the second batch of pegylated Arginase was carried out at a rate of 100 mg/day. Continuous Arginase infusion was stopped at hour 144, and the measurement of the half-life started from this point. The results of the half-life determination are shown in FIG. 22. Time zero in FIG. 22 is equivalent to hour 144 in FIG. 21.

The results suggested that the half-life of the activity of the Arginase could be divided into two phases. The first half-life of the pegylated enzyme was about 6 hours. It took about 6 hours to reduce the relative activity from 100% to 50% (see FIG. 22). However, the second half-life was about 21 days. It took about 21 days to reduce the relative activity from 50% to 25%. This dual half-life effects might be due to a number of factors including the use of higher amount of mnPEG-CC in the pegylation and the specific infusion protocol used.

Example 9B

½-Life Determination of Pegylated Arginase In Vitro Using the Method in Human Blood Plasma Purified Arginase (1 mg) was dissolved in 1 ml of 125 mM borate buffer solution (pH 8.3) on ice. Activated PEG (mPEG-SPA, MW 5,000) (7.14 mg) was added into the protein solution slowly at a mole ratio of Arginase:PEG=1:50. The mixture was stirred on ice for 2.5 h, following the method as described in Example 8B.

Figure 20:
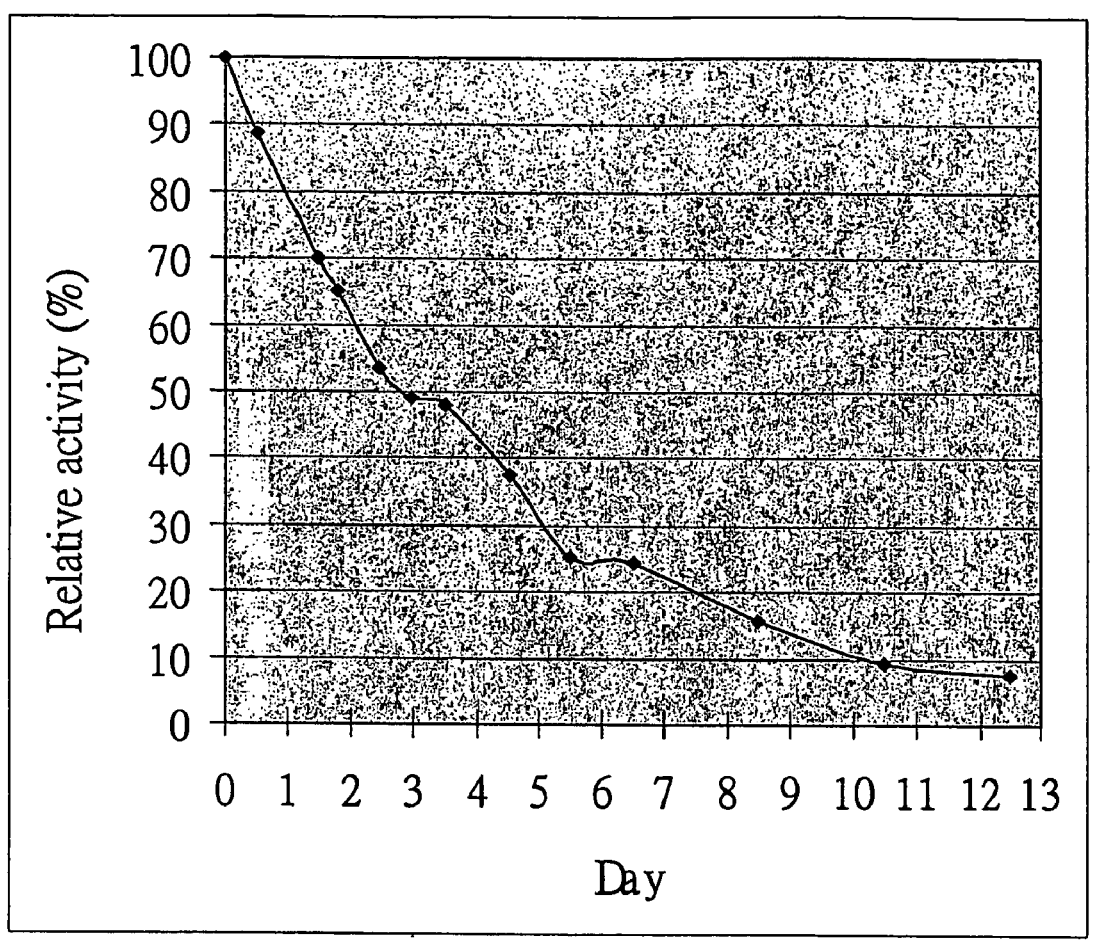
FIG. 20 is a diagram to show the stability of the pegylated Arginase in vitro in human blood plasma.

Pegylated Arginase (305.6 μl) at a concentration of 1 mg/ml was added into human plasma (1 ml) and the final concentration of pegylated Arginase was 0.24 mg/ml. The mixture was divided into 20 aliquots in eppendorf tubes (65 μl mixture in each eppendorf tube) and then incubated at 37° C. A 1-2 μl portion of the mixture from each eppendorf tube was used to test the Arginase activity. Results are shown in FIG. 20. The ½-life was determined to be approximately 3 days. It took about 3 days to reduce the relative activity from 100% to 50%. This is determined by using the curve in FIG. 20.

Example 10

Figure 19A:
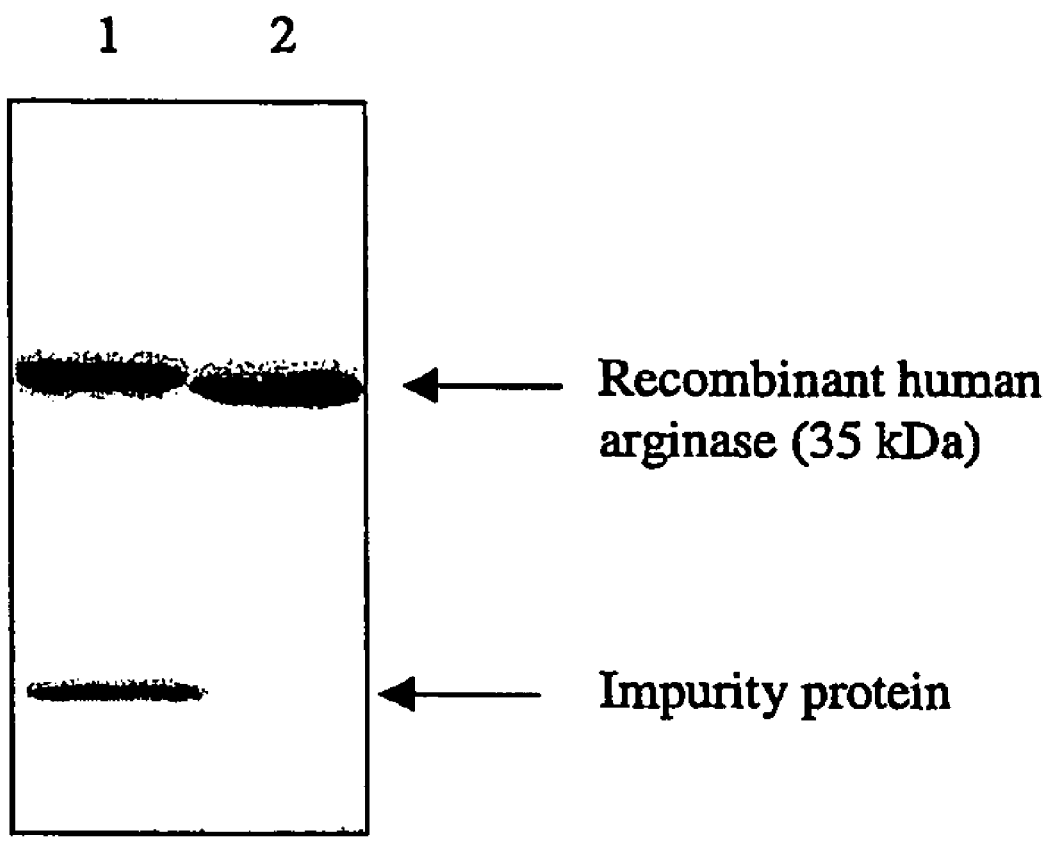
FIGS. 19A and 19B show the measurement of the isolated recombinant human Arginase purity.
Figure 19B:
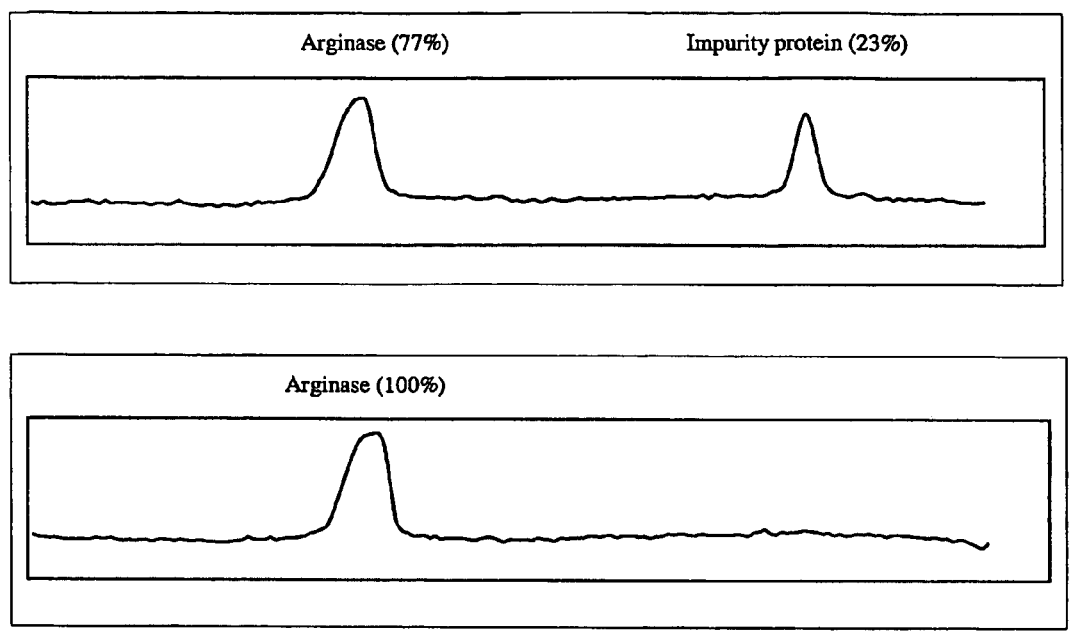

Characterization of *B. subtilis*-Expressed Human Arginase and Pegylated, Isolated and Purified Recombinant Human Arginase (a) Measurement of Purity of Arginase by SDS-PAGE and Lumi-Imaging Purified *E. coli*-expressed Arginase obtained from methods described by Ikemoto et al. (Ikemoto et al., 1990, Biochem. J. 270, 697-703) was compared to purified *B. subtilis*-expressed recombinant human Arginase obtained from methods described in the present invention (FIGS. 19A and 19B). Analysis of densities of total protein bands shown in FIG. 19A with the Lumianalyst 32 program of Lumi-imager™ (Roche Molecular Biochemicals) indicated that the process developed in the present invention produced an Arginase that is to more than 99.9% pure (FIG. 19B). However, an Arginase that is between 80-100% pure may also serve as the active ingredient to prepare a pharmaceutical composition. In the preferred embodiment, recombinant Arginase of 80-100% purity is used. In the more preferred embodiment, the recombinant Arginase according to the present invention is 90-100% pure using SDS-PAGE followed by lumi-inaging.

(b) Measurement of Specific Activity by Coupled Reactions

The rate of the release of urea from 1-arginine by Arginase was monitored in a system containing urease, L-glutamate dehydrogenase and NADPH (Ozer, N., 1985, Biochem. Med. 33, 367-371). To prepare the master mix, 0.605 g Tris, 0.0731 g α-ketoglutarate and 0.4355 g arginine were dissolved in 40 ml dH$_2$O. The pH was adjusted to 8.5 with 1 M HCl and then 0.067 g urease was added to the mixture. The pH was further adjusted to 8.3 with HCl before 0.0335 g glutamate dehydrogenase and 0.0125 g NADPH were added. The final volume was adjusted to 50 ml with dH$_2$O to form the master mix. The master mix (1 ml) was pipetted into a quartz cuvette. For measuring Arginase activity, 1-5 μg Arginase was added and the decrease in absorbance at 340 nm ($A_{340}$) was followed for 1-3 min at 30 degree C. One I.U. of Arginase was defined as the amount of enzyme that released 1 μmol of urea for 1 min under the given conditions. The specific activity of the purified recombinant human Arginase of the present invention was calculated to be 518 I.U./mg of protein, which was significantly higher than the reported values for purified human erythrocyte Arginase (204 I.U./mg of protein; Ikemoto et al., 1989, Ann. Clin. Biochem. 26, 547-553) and the *E. coli*-expressed isolated and purified recombinant human Arginase (389 I.U./mg of protein; Ikemoto et al., 1990, Biochem. J. 270, 697-703).

With mPEG-SPA (MW 5,000), a mole ratio of 1:50 and 2 h 40 min of reaction, the pegylated Arginase retained as much as 114% of its original enzymatic activity (see Example 8C). That means the specific activity of the pegylated human Arginase was 592 I.U./mg.

With MPEG-CC (MW 5,000), the pegylated human Arginase retained 64-68% of its original enzymatic activity (Table 3), similar to that of the pegylated bovine Arginase (Savoca, K. V. et al., 1979, Biochimica et Biophysica Acta 578, 47-53,).

(c) Structural Characterization of the Native Arginase by Electrospray LC/MS

The *B. subtilis*-expressed and purified recombinant human Arginase, according to the amino aid sequence shown in FIG. 2B, contains 329 amino acid residues at a theoretical molecular weight of 35,647.7 Da Simultaneous HPLC/UV and mass spectral analysis of the native Arginase provided a molecular weight of 35,634 Da. The observed molecular weight for the native Arginase was found to correspond well with the theoretical molecular weight of 35,647.7 Da derived from the expected amino acid sequence of a 6×His-tagged human Arginase (FIG. 2B). The purity was found to be 98% by HPLC/UV based on LC/MS and 100% by LC/MS based on HPLC/UV detection at 215 nm relative responses.

(d) Structural Characterization of the Native Arginase and the Pegylated Arginase by Gel Filtration Chromatography Studied by gel filtration chromatography in a HiLoad 16/60 superdex gel filtration column (Pharmacia) at the protein concentration of about 2.8 mg/ml in PBS buffer, the molecular weight of the native Arginase was found to be about 78 kDa and that of the pegylated Arginase (prepared in Example 8C) was about 688 kDa. As the molecular weight of monomeric Arginase is about 36 kDa, the results suggested that the native Arginase exists as a dimer in PBS buffer.

(e) Secondary Structural Studies

Circular dichroism (CD) was used to analyze the secondary structures of the purified Arginases in a JASCO model J810 CD spectrometer. At equal protein concentrations in 10 mM potassium phosphate buffer (pH 7.4), the CD spectrum of the native Arginase was found to be very similar to that of the pegylated Arginase (prepared in Example 8C) when scanned from 195 nm to 240 nm, indicating that the native form and the pegylated form of Arginase have nearly identical secondary structures.

(f) Determination of pI Point

Using a Bio-Rad Model 111 mini IEF cell, the isoelectric (pI) of the native Arginase (prepared in Example 8C) was found to be 9.0, which is consistent with the published value of 9.1 in literature (Christopher and Wayne, 1996, Comp. Biochem. Physiol. 114B, 107-132).

(g) Functional Characterization and Determination of Kinetic Properties

Using the method reported by Ikemoto et al. (1990, Biochem. J. 270, 697-703) for measuring Arginase activities, the native Arginase gave a $K_m$ of 1.9±0.7 mM, a $V_{max}$ of 518 µmol urea min$^{-1}$ mM$^{-1}$, a $k_{cat}$ of 2.0±0.5 s$^{-1}$, and a $k_{cat}/K_m$ of 1.3±0.4 mM$^{-1}$ s$^{-1}$. The $K_m$ value of the purified native Arginase was found to be similar to the published value (2.6 mM) of the human liver Arginase in literature (Carvajal, N. et al., 1999). Moreover, about 1 mM of Mn$^{2+}$ ions and a temperature of 30-50 degree C. are required to achieve maximum activity for the native Arginase.

The pegylated Arginase gave a $K_m$ of 2.9±0.3 nM and a $V_{max}$ of 360 µmol urea min$^{-1}$ mM$^{-1}$. The $K_m$ value of the pegylated Arginase is similar to that of the native Arginase, suggesting that the binding affinity towards arginine is retained after pegylation. Moreover, about 1 mM of Mn$^{2+}$ ions, a temperature of 40-50 degree C., and a pH of 10 are required to achieve maximum activity for the pegylated Arginase.

The functional properties of Arginase before and after pegylation are similar, which indicates that the covalent attachment of mPEG-SPA molecules to Arginase improves its properties as a whole.

Example 11

Treatment Protocol Using Exogenously Adminstered Arginase

Blood samples of patients are taken daily throughout treatment for arginine levels, Arginase activities, complete blood picture and flill clotting profile. Renal and liver functions are taken at least every other days, sooner if deemed necessary.

Vital signs (BP, Pulse, Respiratory rate, Oximeter reading) are taken every 15 minutes for 1 hour after commencement of Arginase infusion then hourly until stable. Thereafter, at the discretion of the treating physician.

20 minutes before Arginase infusion, premedication with dipheneramine 10 mg iv. and hydrocortisone 100 mg iv. to be given before each fresh infusion of Arginase or at the discretion of the treating physician.

On day One Arginase is infused over 30 minutes. Thereafter, Arginase is infused weekly for at least 8 weeks. This may be continued if anti-tumour activity is observed.

Example 12

Example of Treatment Protocol Using Exogenously Administered Arginase

A 54-year old Chinese lady with metastatic rectal carcinoma with extensive pulmonary metastases that failed all standard treatments was treated with pegylated recombinant Arginase in early August 2001. Her main symptoms were cough, poor appetite and constipation. Her cancer marker CEA was 1100 U/ml. Informed consent for treatment with pegylated recombinant Arginase was obtained prior to treatment.

Treatment Methodology 850 mg of lyophilised recombinant Arginase I was administered. The drug was reconstituted in PBS and pegylated. The pegylated enzyme was found to be of full activity.

Results

Figure 28:
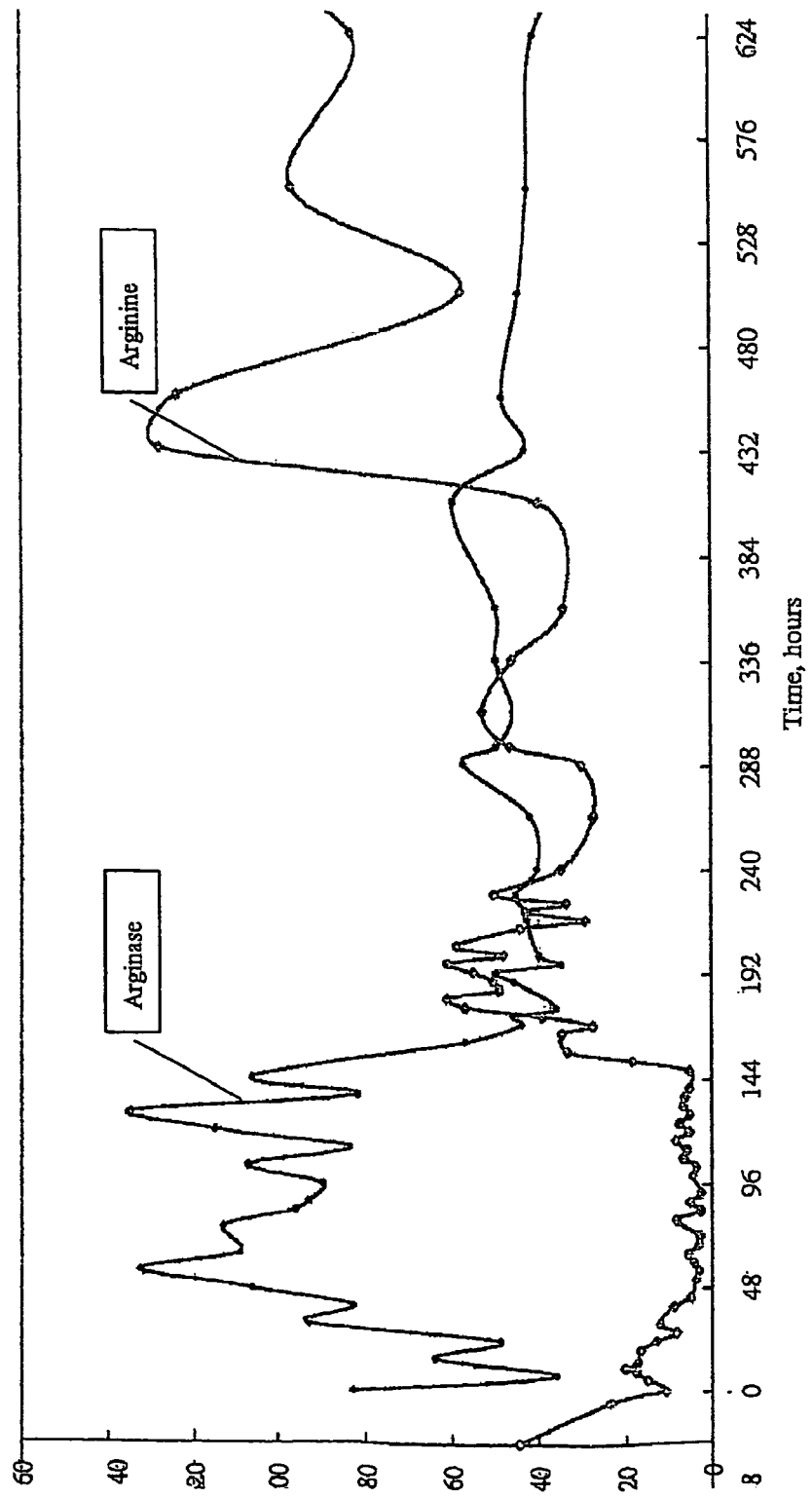
FIG. 28 and FIG. 29 show in vivo arginine and CEA levels respectively of the patient during treatment as described in Example 12.
Figure 29:
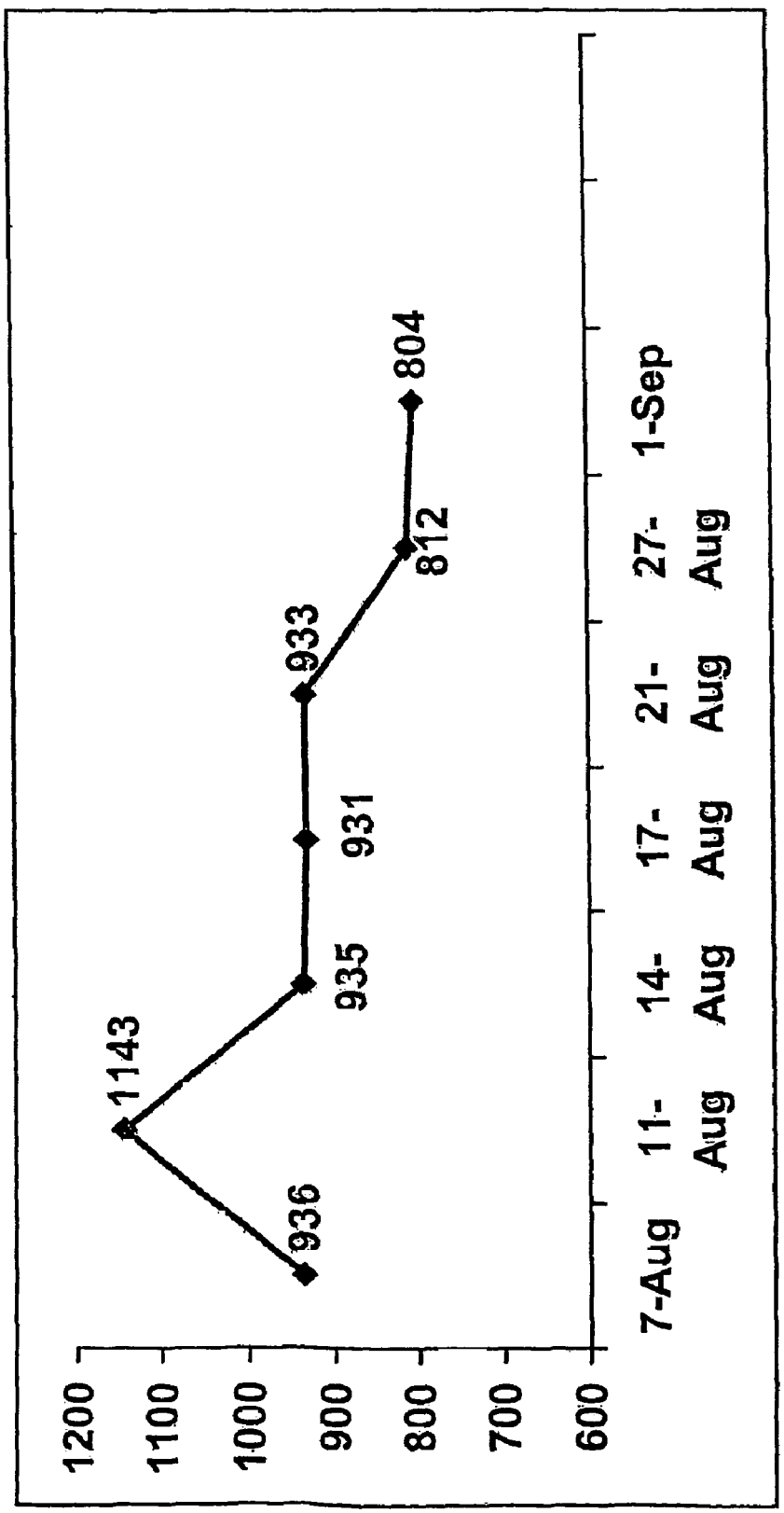

Results are shown in FIGS. 28 and 29. FIG. 28 shows satisfactory depletion of arginine between 1-5 µM for 5 days (also see FIG. 21). FIG. 29 shows a decrease of CEA levels from 1100 to 800 in 4 weeks.

1) Unlike chemotherapy this treatment resulted in no marrow suppressive effects or hair loss.

2) It can deplete arginine in a controlled manner, keeping the arginine levels within the therapeutic range (1-8 µM) for the desired period of 5 days, which in vitro data suggest provide optimal tumour kill.

3) No major side effects and the patient tolerated the treatment with only slight headache which may not be directly due to treatment.

4) Both biochemical and radiological improvement of the disease was observed after treatment, with CEA dropping by 30% and clearing up of upper zone disease on chest X ray.

Example 13

In Vivo Arginne Depletion in Laboratory Rats with Arginase

In this example, four groups of rats (two in each group, one male and one female) were given dosages of various amounts of Arginase obtained from example 8C on day 0. Blood samples were drawn from their tail veins on day 0 before intraperitoneal injection of the recombinant human Arginase, day 1 to day 6, then every 2 days.

Figure 23:
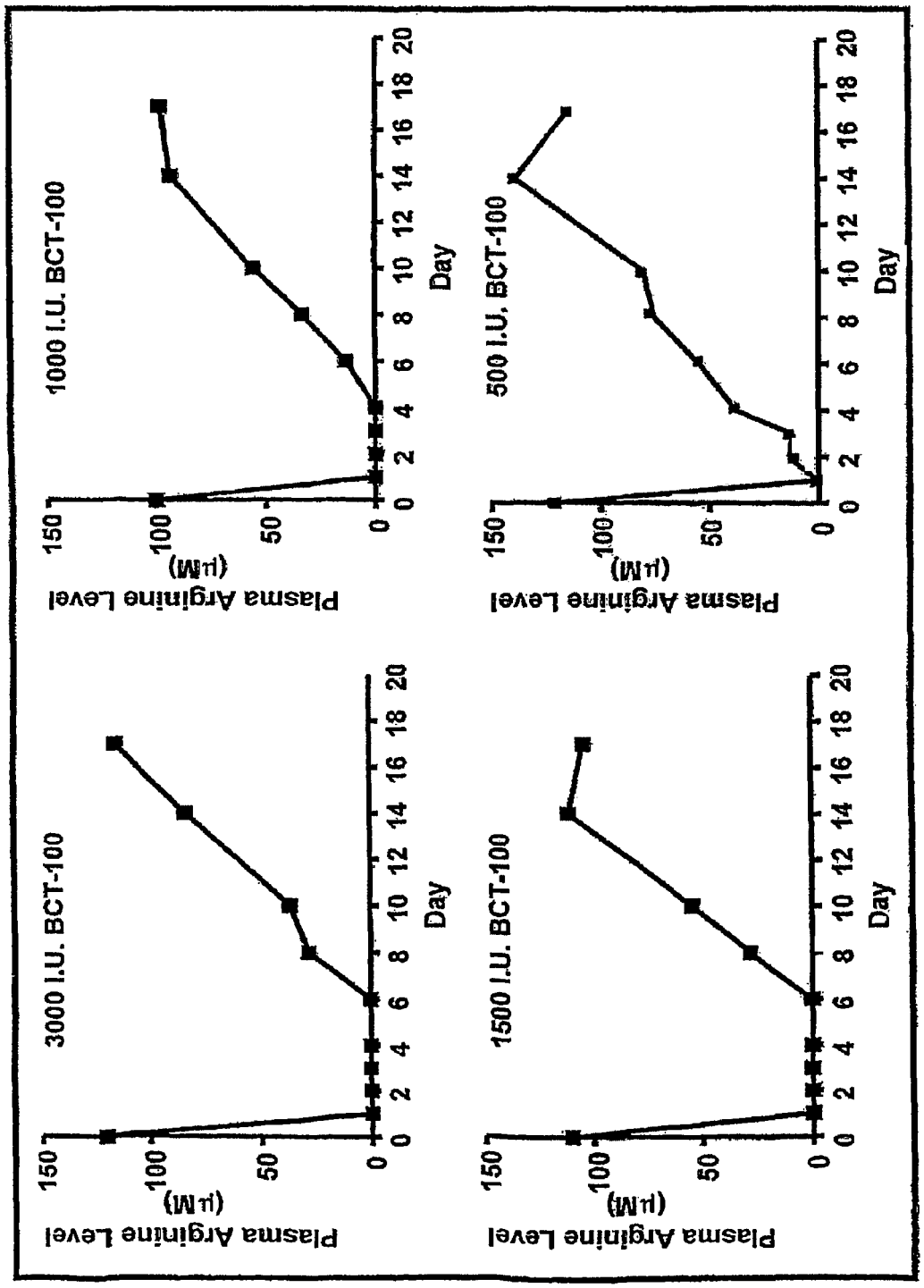
FIG. 23 is a comparison of arginine depletion in four groups of laboratory rats administered intraperitoneally with different dosages of pegylated recombinant human Arginase (500 I.U., 1000 I.U., 1500 I.U., and 3000 I.U.).

As shown in FIG. 23, undetectable arginine level was achieved in all groups and appeared to be dose dependent with 500 I.U. giving only after one day of arginine depletion. With 1000 I.U. (500 I.U. administered in the mormnig and another 500 I.U. administered in the afternoon), there was a 4-day period with complete arginine depletion. With single dose of 1500 I.U. administered, there was 6-day arginine depletion. By doubling this dose to 3000 I.U., the duration of complete arginine depletion did not appear to be prolonged to any further extent.

Therefore, 1500 I.U. of pegylated Arginase administered intraperitoneally appears to be the optimal dose for arginine depletion with undetectable arginine level for 6 days.

Example 14

Comparison of Changes in Level of Components in Blood Between Normal Rats and Rats with Zero Arginine Level Induced by Arginase from Day 1 to Day 5

Intracardiac arterial blood samples were taken from a group of 5 rats on day 0 before administering Arginase. The day 0 samples served as the untreated control. The level of total protein, albumin, globulin, SGOT/AST, SGPT/ALT, haemoglobin, fibrinogen A.P.T.T./second, prothrombin/second, number of white blood cells (WBC) and platelets were measured by Pathlab Medical Laboratory. Ltd, $2^{nd}$ Floor Henan Building, 90-92 Jaffe Road, Wanchai, Hong Kong. The rats then were injected with single dose of 1500 I.U. of Arginase intraperitoneally. Zero arginine level were achieved in all rats. From day 1 to day 5, one rat was sacrificed on each day and intracardiac arterial blood sample was taken and measured by PathLab Medical Laboratory. Results show that all proteins were within the normal ranges as cited by PathLab Medical Laboratory.

Example 15

The Response Upon Arginine Depletion in Hep3B Tumour-Bearing Nude Mice

A human hepatoma cell line (Hep3B2.1-7) was inoculated subcutaneously into the right flank of six BALB/c nude mice to induce growth of the tumour. Three randomly picked mice were administered intraperitoneally once a week with 500 I.U. pegylated Arginase obtained from the method described in example 8C while the other three mice were not given any Arginase treatment to serve as the control. The implanted mice were observed once every two days for the growth of the solid tumour in situ by digital calliper measurements to determine tumour size which is calculated according to the formula:

Tumour size (mm)=average of two perpendicular diameters and one diagonal diameter.

The number of mice that died in each group was also recorded on a daily basis.

Figure 24:
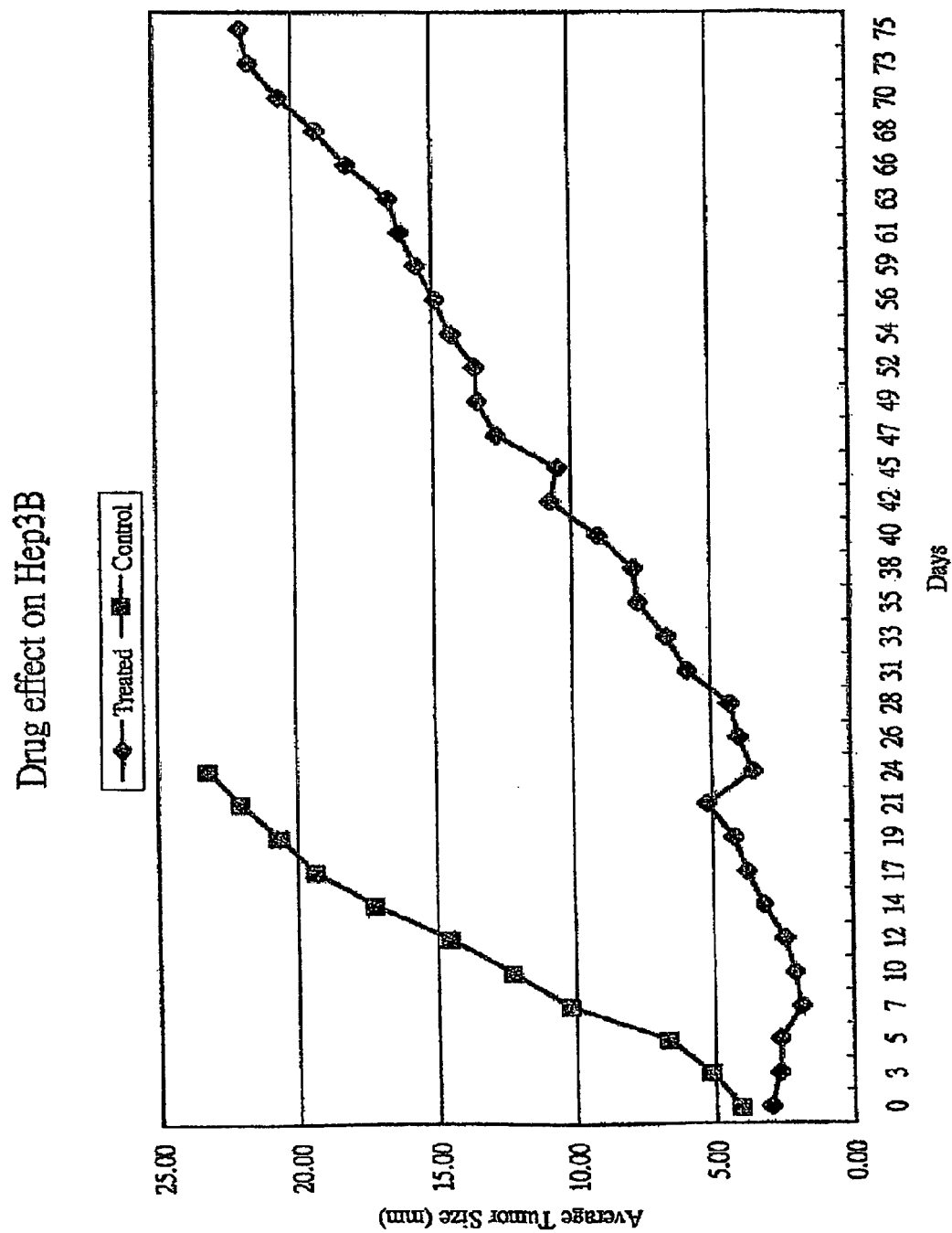
FIG. 24 shows the comparison of survival rate, average tumour size and tumour growth rate of tumours between 2 groups of nude mice which have tumours induced by implantation with Hep3B cells. One group was treated with Arginase with dosage of 500 I.U. intraperitoneally while the other control group was not treated with Arginase.

As shown in FIG. 24, the rate of increase in size of the tumour per day in control group was approximately 6 times the rate increase in group treated with pegylated Arginase for the first 20 days of the experiment. 2 mice in the control group were dead within 24 days while the mice treated with pegylated Arginase can survive for at least 75 days.

Example 16

The Response Upon Arginine Depletion in PLC/PRF/5 Tumour-Bearing Nude Mice

In this example, a solid tumour of human hepatoma (PLC/PRF/5) was implanted subcutaneously into the back of ten BALB/c nude mice to induce growth of tumour. Five randomly picked mice were administered intraperitoneally once a week with 500 I.U. pegylated Arginase obtained from the method described in example 8C while the other five mice were given 200 μl phosphate buffer saline (PBS) intraperitoneally to serve as the control. The implanted mice were observed once every two days for the growth of the solid tumour in situ by digital calliper measurements to determine tumour size and mass.

Tumour size is measured as described in example 15 while tumour mass is calculated according to the formula:

Tumour mass (mg)=length×width$^2$/2 (assuming a specific gravity of 1.0 g/cm$^3$)

(where length is the longest perpendicular diameter and width is the shortest perpendicular diameter)

Figure 25A:
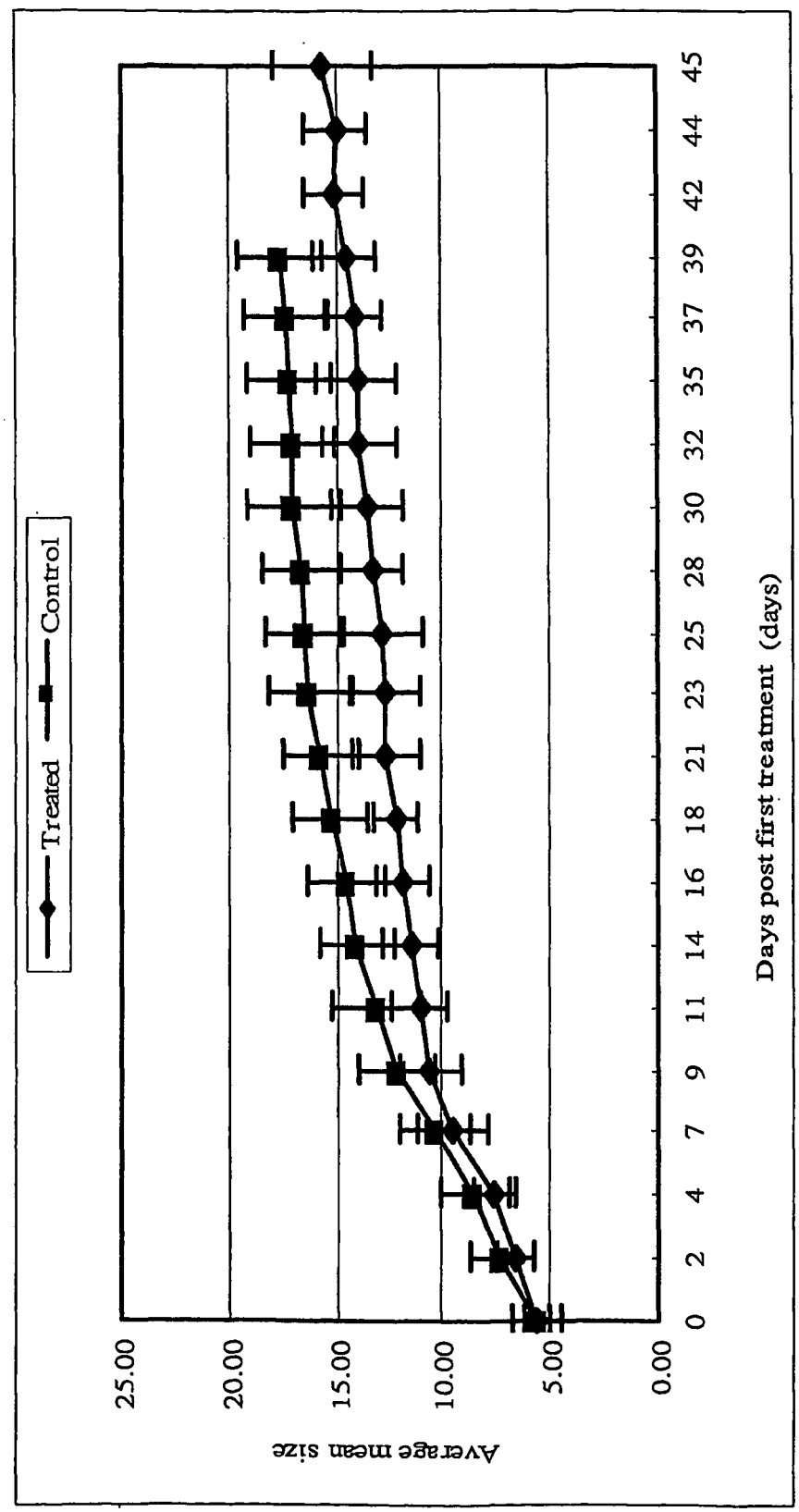
FIGS. 25A and 25B show the comparison of average tumour size and average tumour weight between 2 groups of nude mice which have tumours induced by implantation with PLC/PRF/5 cells. One group was treated with Arginase with dosage of 500 I.U. intraperitoneally while the other control group was not treated with Arginase.
Figure 25B:
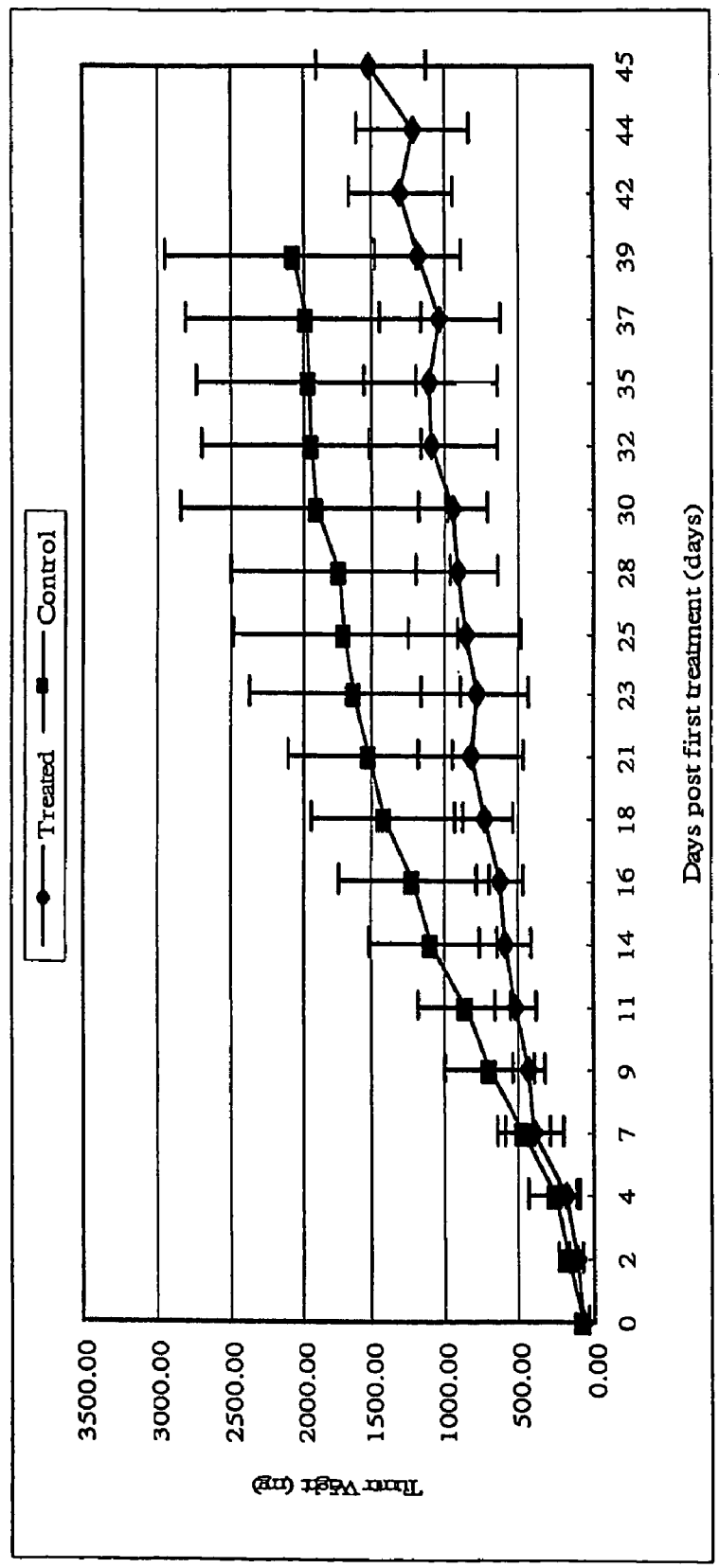

As shown in FIG. 25A, the rate of increase in size of the tumour per day was approximately 6.5 mm/day in the control group and the rate of increase in size of tumour in the group treated with pegylated Arginase is approximately 5.3 mm/day for the first 39 days of the experiment. As shown in FIG. 25B, the rate of increase in mass of the tumour per day was approximately 1.8 times higher in the control group than that of the treated group.

Example 17

The Response Upon Arginine Depletion in HuH-7 Tumour-Bearing Nude Mice

In this example, a solid tumour of human hepatoma (HuH-7) was implanted subcutaneously into the back of ten BALB/c nude mice to induce growth of tumour. Five randomly picked mice were administered intraperitoneally once a week with 500 I.U. pegylated Arginase obtained from the method described in example 8C while the other five mice were given 200 μl phosphate buffer saline (PBS) per week intraperitoneally to serve as the control. The implanted mice were observed once every two days for the growth of the solid tumour in situ by digital calliper measurements to determine tumour size and mass as described in examples 15 and 16.

Figure 26B:
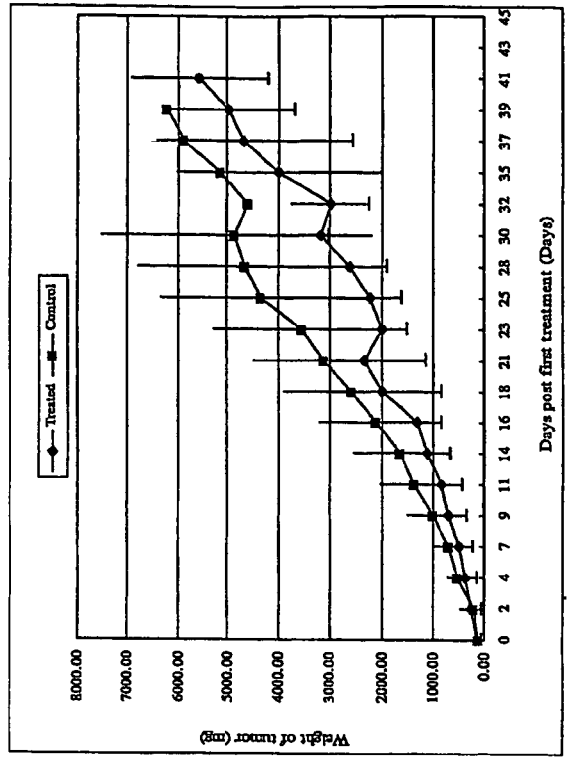
FIGS. 26A and 26B show the comparison of average tumour size and average tumour weight of 2 groups of nude mice which have tumours induced by implantation with HuH-7 cells. One group was treated with Arginase with dosage of 500 I.U. intraperitoneally while the other control group was not treated with Arginase.
Figure 26A:
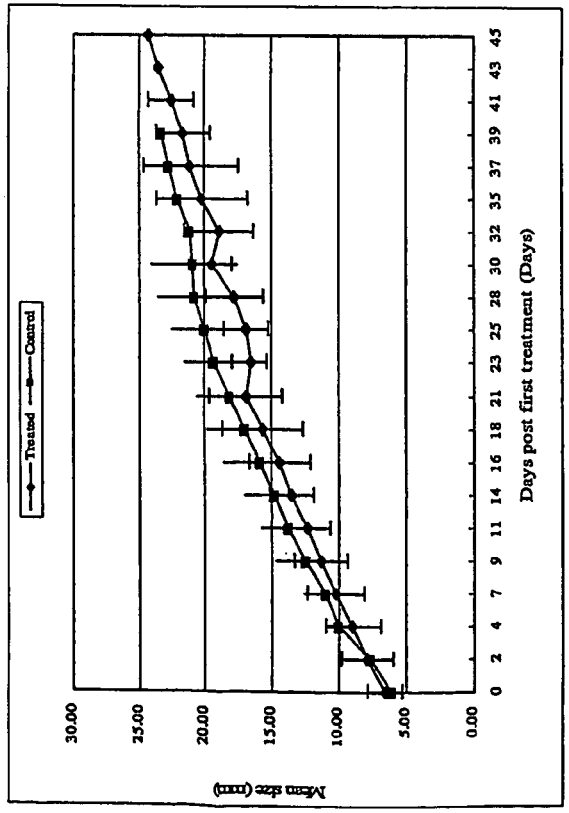

As shown in FIG. 26A, the rate increase in size of the tumour per day was approximately 6.0 mm/day in control group and the rate of increase in size of tumour in the group treated with pegylated Arginase is approximately 5.6 mm/day for the first 18 days of the experiment. As shown in FIG. 26B, the rate of increase in mass of the tumour per day was approximately 1.4 times higher in the control group than that of the treated group.

Example 18

The Response Upon Arginine Depletion in MCF-7 Tumour-Bearing Nude Mice

In this example, a human breast cancer cell line (MCF-7) was inoculated subcutaneously into the right flank of four BALB/c nude mice to induce growth of tumour. Three randomly picked mice were administered intraperitoneally once a week with 500 I.U. pegylated Arginase obtained from the method described in Example 8C while the last one mouse were not given any arginine treatment to serve as the control. The implanted mice were observed once every two days for the growth of the solid tumour in situ by digital calliper measurements to determine tumour size as described in Example 15.

Figure 27:
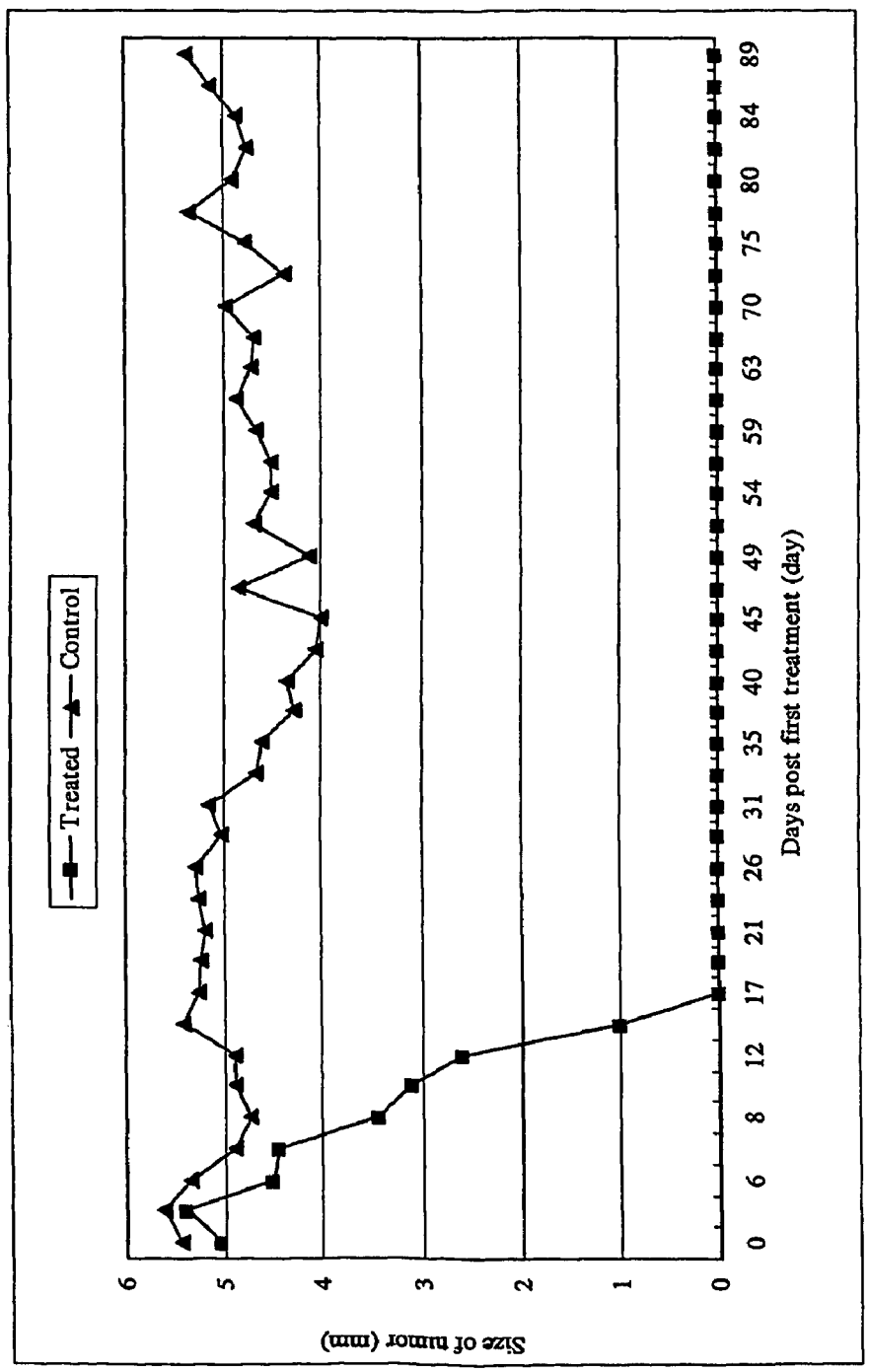
FIG. 27 shows the comparison of average tumour size of 2 groups of nude mice which have tumours induced by implantation with MCF-7 cells. One group was treated with Arginase with dosage of 500 I.U. intraperitoneally while the other control group was not treated with Arginase.

As shown in FIG. 27, the tumour inoculated in the mice treated with pegylated Arginase disappeared within 20 days of the experiment It must be noted that as used herein and in the appended claims, the singular forms "a," "and," and "the" include plural references unless the context clearly dictates otherwise. Thus, for example, reference to "a pharmaceutical preparation" includes mixtures of different preparations and reference to "the method of treatment" includes reference to equivalent steps and methods known to those skilled in the art and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with. The invention having been fully described, modifications within its scope will be apparent to those of ordinary skill in the art. All such modifications are within the scope of the invention.

Formulations of the pharmaceutical composition of the present invention can be used in the form of a solid, a solution, an emulsion, a dispersion, a micelle, a liposome, and the like, wherein the resulting formulation contains one or more of the modified human arginase in the practice of the present invention, as active ingredients, in a mixture with an organic or inorganic carrier or excipient suitable for enteral or parenteral applications. The active ingredients may be the arginase, for example, with the usual non-toxic, pharmaceutically acceptable carriers for tablets, pellets, capsules, suppositories, solutions, emulsions, suspensions, and any other form suitable for use in manufacturing preparations, in solid, semisolid, or liquid form. In addition auxiliary, stabilizing, thickening and coloring agents and perfumes may be used. The active ingredients of one or more arginase are included in the pharmaceutical formulation in an amount sufficient to produce the desired effect upon the target process, condition or disease.

Pharmaceutical formulations containing the active-ingredients contemplated herein may be in a form suitable for oral use, for example, as tablets, troches, lozenges, aqueous or oily suspensions, dispersible powders or granules, emulsions, hard or soft capsules, or syrups or elixirs. Formulations intended for oral use may be prepared according to any method known in the art for the manufacture of pharmaceutical formulations. The tablets may be uncoated or they may be coated by known techniques to delay disintegration and absorption in the gastrointestinal tract, thereby providing sustained action over a longer period. They may also be coated to form osmotic therapeutic tablets for controlled release.

In some cases, formulations for oral use may be in the form of hard gelatin capsules wherein the active ingredients are mixed with an inert solid diluent, for example, calcium carbonate, calcium phosphate, kaolin, or the like. They may also be in the form of soft gelatin capsules wherein the active ingredients are mixed with water or an oil medium, for example, peanut oil, liquid paraffin, or olive oil.

The pharmaceutical formulations may also be in the form of a sterile injectable solution or suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,4-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, or synthetic fatty vehicles, like ethyl oleate, or the like. Buffers, dextrose solutions preservatives, antioxidants, and the like, can be incorporated or used as solute to dissolve the soluble enzyme as required.

The pharmaceutical formulations may also be an adjunct treatment together with other chemotherapeutic agents.

In the claims, an arginase that has an amino acid sequence substantially the same as the sequence shown in SEQ ID No. 9 means that the sequence is at least 30% identical to that shown in SEQ ID No. 9 or that using the Arginase activity assay as described herein, there is no significant difference in the enzymatic activity between the enzyme of SEQ ID No. 9 and the one that is substantially similar. The six histidines are provided for ease of purification, and the additional methionine group provided at the amino terminus thereof is to allow translation to be initiated It is clear to one skilled in the art that other forms of purification may also be used, and therefore a "substantially similar" arginase does not need to have any homology with the MHHHHHH sequence of SEQ ID No. 3. In some bacterial strains there may be at least 40% homology with SEQ. SEQ ID No. 9. Some mammalian arginase may be 70% homology with SEQ ID No. 9.

The invention claimed is:

1. A method of treating human liver, breast, colon or rectal cancer, comprising administering parenterally to a subject in need thereof a modified, full-length recombinant human arginase I polypeptide having an amino acid sequence encoded by a nucleic acid of SEQ ID NO: 8, which wherein said human arginase I is modified by covalent linkage to at least one polyethylene glycol (PEG) molecule, wherein the administration of the modified, full-length recombinant human arginase I polypeptide reduces the physiological arginine level in the subject to below 10 μM for at least 3 days.

2. A method of treatment of human liver, breast, colon or rectal cancer, comprising administering parenterally to a subject in need thereof a modified, full-length recombinant human arginase I polypeptide having the amino acid sequence of SEQ ID NO: 9, wherein said human arginase I modified by covalent linkage to at least one polyethylene glycol (PEG) molecule, wherein the administration of the modified, full-length recombinant human arginase I polypeptide reduces the physiological arginine level in the subject to below 10 μM for at least 3 days.

3. A method of treating human liver, breast, colon or rectal cancer, comprising administering parenterally to a subject in need thereof a modified, full-length recombinant human arginase I polypeptide having an amino acid sequence encoded by a nucleic acid of SEQ ID NO: 2, wherein said human arginase I is modified by covalent linkage to at least one polyethylene glycol (PEG) molecule, wherein the administration of the modified, full-length recombinant human arginase I polypeptide reduces the physiological arginine level in the subject to below 10 μM for at least 3 days.

4. A method of treating human liver, breast, colon or rectal cancer, comprising administering parenterally to a subject in need thereof a modified, full-length recombinant human arginase I polypeptide having the amino acid sequence of SEQ ID NO: 3, wherein said human arginase I is modified by covalent linkage to at least one polyethylene glycol (PEG) molecule, wherein the administration of the modified, full-length recombinant human arginase I polypeptide reduces the physiological arginine level in the subject to below 10 μM for at least 3 days.

5. A method of treating human liver, breast, colon or rectal cancer, comprising administering parenterally to a subject in need thereof a modified, full-length recombinant human arginase I polypeptide of 80-100% purity as determined by gel chromatography and densitometry having an amino acid sequence encoded by a nucleic acid of SEQ ID NO: 8, wherein said human arginase I is modified by covalent linkage to at least one polyethylene glycol (PEG) molecule wherein the administration of the modified, full-length recombinant human arginase I polypeptide reduces the physiological arginine level in the subject to below 10 μM for at least 3 days.

6. A method of treating human liver, breast, colon or rectal cancer, comprising administering parenterally to a subject in need thereof a modified, full-length recombinant human arginase I polypeptide of 80-100% purity as determined by gel chromatography and densitometry, having the amino acid sequence of SEQ ID NO: 9, wherein said human arginase I is modified by covalent linkage to at least one polyethylene glycol (PEG) molecule, wherein the administration of the modified, full-length recombinant human arginase I polypeptide reduces the physiological arginine level in the subject to below 10 μM for at least 3 days.

7. A method of treating human liver, breast, colon or rectal cancer, comprising administering parenterally to a subject in need thereof a modified, full-length recombinant human arginase I polypeptide of 80-100% purity as determined by gel chromatography and densitometry having an amino acid sequence encoded by a nucleic acid of SEQ ID NO: 2, wherein said human arginase I is modified by covalent linkage to at least one polyethylene glycol (PEG) molecule wherein the administration of the modified, full-length recombinant human arginase I polypeptide reduces the physiological arginine level in the subject to below 10 μM for at least 3 days.

8. A method of treating human liver, breast, colon or rectal cancer, comprising administering parenterally to a subject in need thereof a modified, full-length recombinant human arginase I polypeptide of 80-100% purity as determined by gel chromatography and densitometry having the amino acid sequence of SEQ ID NO: 3, wherein said human arginase I is modified by covalent linkage to at least one polyethylene glycol (PEG) molecule wherein the administration of the modified, full-length recombinant human arginase I polypeptide reduces the physiological arginine level in the subject to below 10 μM for at least 3 days.

9. A method of treating human liver, breast, colon or rectal cancer, comprising administering parenterally to a subject in need thereof a modified, full-length recombinant human arginase I polypeptide comprising the amino acid sequence of SEQ ID NO: 3, which is of 80-100% purity, wherein said human arginase I is modified by covalent linkage to at least one polyethylene glycol (PEG) molecule, and has an extended half-life of at least 3 days.

10. The method of claim 9, wherein the administration of the modified, full-length recombinant human arginase I polypeptide reduces the physiological arginine level in the subject to below 10 μM for at least 3 days.

* * * * *

UNITED STATES PATENT AND TRADEMARK OFFICE
CERTIFICATE OF CORRECTION

| | | |
|---|---|---|
| PATENT NO. | : 7,951,366 B2 | Page 1 of 1 |
| APPLICATION NO. | : 10/518223 | |
| DATED | : May 31, 2011 | |
| INVENTOR(S) | : Ning Man Cheng, Yun Chung Leung and Wai Hung Lo | |

It is certified that error appears in the above-identified patent and that said Letters Patent is hereby corrected as shown below:

Please replace col. 39, line 6 with the following corrected version:
-- a nucleic acid of SEQ ID NO: 8, [[which]] wherein said human --

Please replace col. 39, line 13 with the following corrected version:
-- 2. A method of ~~treatment of~~ treating human liver, breast, colon or --

Please replace col. 39, line 16 with the following corrected version:
-- sequence of SEQ ID NO: 9, wherein said human arginase I is --

Signed and Sealed this
Eleventh Day of October, 2011

David J. Kappos
*Director of the United States Patent and Trademark Office*